(12) United States Patent
Davis et al.

(10) Patent No.: US 10,307,337 B2
(45) Date of Patent: Jun. 4, 2019

(54) ORAL ADMINISTRATION COUPLER FOR BACK-OF-MOUTH DELIVERY

(71) Applicant: NEOMED, INC., Woodstock, GA (US)

(72) Inventors: Benjamin Martin Davis, Woodstock, GA (US); Mark M. Costello, County Mayo (IE); Mariann Cary, Canton, GA (US); Adrian McDermott, County Galway (IE)

(73) Assignee: NeoMed, Inc., Woodstock, GA (US)

( * ) Notice: Subject to any disclaimer, the term of this patent is extended or adjusted under 35 U.S.C. 154(b) by 0 days.

(21) Appl. No.: 15/815,713

(22) Filed: Nov. 17, 2017

(65) Prior Publication Data

US 2018/0071169 A1    Mar. 15, 2018

Related U.S. Application Data

(60) Division of application No. 15/652,742, filed on Jul. 18, 2017, which is a continuation-in-part of application No. 15/078,674, filed on Mar. 23, 2016.
(Continued)

(51) Int. Cl.
*A61J 15/00* (2006.01)
*A61J 7/00* (2006.01)
(Continued)

(52) U.S. Cl.
CPC ......... *A61J 7/0053* (2013.01); *A61J 11/0035* (2013.01); *A61J 15/0011* (2013.01);
(Continued)

(58) Field of Classification Search
CPC ........ A61J 7/0053; A61J 7/00; A61J 11/0035; A61J 15/0011; A61M 2039/1033; A61M 2202/0482; A61M 39/10
See application file for complete search history.

(56) References Cited

U.S. PATENT DOCUMENTS 1,393,209 A   10/1921  Evans
1,704,921 A    3/1929  Nicoll
(Continued)

FOREIGN PATENT DOCUMENTS

CA    2548976 A1   12/2007
DE    2108381 A1    8/1972
(Continued)

OTHER PUBLICATIONS

Kasper et al.; "ENFit Enteral Connections: Are You Ready?"; Premier Safety Institute; Mar. 26, 2015; 5 pgs.
(Continued)

*Primary Examiner* — Deanna K Hall
(74) *Attorney, Agent, or Firm* — Gardner Groff Greenwald & Villanueva PC

(57) ABSTRACT

An improved oral administration coupler for delivery of fluids such as medications and nutritional fluids. Example oral administration couplers have a first end with an applicator for oral delivery to an infant, and a second end with a coupling compatible with an enteral fluid delivery syringe. A fluid delivery conduit extends in fluid communication from the first end to the second end, to deliver fluid from the syringe to the infant. In some example embodiments, the coupler is configured for back-of-mouth delivery, and can comprise a generally elongate and at least partially flexible tube or straw.

35 Claims, 41 Drawing Sheets

Related U.S. Application Data

(60) Provisional application No. 62/396,532, filed on Sep. 19, 2016, provisional application No. 62/363,498, filed on Jul. 18, 2016, provisional application No. 62/137,293, filed on Mar. 24, 2015, provisional application No. 62/192,726, filed on Jul. 15, 2015.

(51) Int. Cl.

| | | |
|---|---|---|
| *A61M 39/10* | (2006.01) | |
| *A61L 29/04* | (2006.01) | |
| *A61L 29/06* | (2006.01) | |
| *A61M 5/142* | (2006.01) | |
| *A61J 11/00* | (2006.01) | |
| *A61M 5/31* | (2006.01) | |

(52) U.S. Cl.
CPC ............ *A61L 29/041* (2013.01); *A61L 29/06* (2013.01); *A61M 5/142* (2013.01); *A61M 39/10* (2013.01); *A61J 15/0076* (2015.05); *A61M 2005/3139* (2013.01); *A61M 2039/1033* (2013.01); *A61M 2202/0482* (2013.01)

(56) References Cited

U.S. PATENT DOCUMENTS

| | | |
|---|---|---|
| 2,708,438 A | 5/1955 | Cohen |
| 2,869,543 A | 1/1959 | Ratcliff et al. |
| 2,939,459 A | 6/1960 | Lazarte et al. |
| 3,326,215 A | 6/1967 | Sarnoff et al. |
| 3,370,754 A | 2/1968 | Cook et al. |
| 3,489,147 A | 1/1970 | Shaw |
| 3,557,787 A | 1/1971 | Cohen |
| 3,570,486 A | 3/1971 | Engelsher |
| 3,572,337 A * | 3/1971 | Schunk ................ A61J 7/0053 604/227 |
| 3,659,749 A | 5/1972 | Schwartz |
| 3,678,931 A | 7/1972 | Cohen |
| 3,680,558 A | 8/1972 | Kapelowitz |
| 3,682,174 A | 8/1972 | Cohen |
| 3,684,136 A | 8/1972 | Baumann |
| 3,685,514 A | 8/1972 | Cheney |
| 3,756,390 A | 9/1973 | Abbey et al. |
| 3,885,562 A | 5/1975 | Lampkin |
| 3,885,710 A | 5/1975 | Cohen |
| 3,896,805 A | 7/1975 | Weingarten |
| 3,921,633 A | 11/1975 | Tischlinger |
| 4,127,126 A | 11/1978 | Schunk |
| 4,171,699 A | 10/1979 | Jones et al. |
| 4,237,935 A | 12/1980 | Delmonte et al. |
| 4,254,768 A | 3/1981 | Ty |
| 4,351,334 A | 9/1982 | Inglefield, Jr. |
| D267,536 S | 1/1983 | Findlay |
| 4,416,273 A | 11/1983 | Grimes |
| 4,464,174 A | 8/1984 | Ennis |
| D282,807 S | 3/1986 | Hasse |
| D287,877 S | 1/1987 | Holewinski et al. |
| 4,639,248 A | 1/1987 | Schweblin |
| 4,693,706 A | 9/1987 | Ennis, III |
| 4,702,737 A | 10/1987 | Pizzino |
| 4,904,238 A | 2/1990 | Williams |
| 4,941,873 A | 7/1990 | Fischer |
| 4,994,068 A | 2/1991 | Hufnagle |
| D320,084 S | 9/1991 | Stewart et al. |
| D323,031 S | 1/1992 | Ahlstrand et al. |
| 5,092,854 A | 3/1992 | Black |
| 5,115,816 A | 5/1992 | Lee |
| 5,147,324 A | 9/1992 | Skakoon et al. |
| D330,862 S | 11/1992 | Shibley et al. |
| 5,176,415 A | 1/1993 | Choksi |
| 5,188,599 A | 2/1993 | Botich et al. |
| 5,244,122 A | 9/1993 | Botts |
| 5,279,566 A | 1/1994 | Kline, Jr. et al. |
| 5,286,067 A | 2/1994 | Choksi |
| 5,372,586 A | 12/1994 | Haber et al. |
| 5,385,372 A | 1/1995 | Utterberg |
| 5,395,345 A | 3/1995 | Gross |
| 5,401,255 A | 3/1995 | Sutherland |
| D369,214 S | 4/1996 | Nason |
| 5,533,973 A | 7/1996 | Piontek et al. |
| 5,569,193 A | 10/1996 | Hofstetter et al. |
| 5,591,344 A | 1/1997 | Kenley et al. |
| D383,205 S | 9/1997 | Pagay et al. |
| 5,704,918 A | 1/1998 | Higashikawa |
| 5,779,668 A | 7/1998 | Grabenkort |
| 5,785,682 A | 7/1998 | Grabenkort |
| 5,824,012 A | 10/1998 | Burchett et al. |
| 5,836,919 A | 11/1998 | Skurka et al. |
| 5,843,042 A | 12/1998 | Ren |
| 5,876,379 A | 3/1999 | Beauvais et al. |
| 5,881,774 A | 3/1999 | Utterberg |
| 5,891,165 A * | 4/1999 | Buckner ............... A61J 7/0053 604/194 |
| 5,951,519 A | 9/1999 | Utterberg |
| 6,010,481 A | 1/2000 | Lee |
| D420,129 S | 2/2000 | McMahon |
| 6,071,261 A | 6/2000 | Augusto |
| 6,126,644 A | 10/2000 | Naganuma et al. |
| 6,126,679 A | 10/2000 | Botts |
| 6,164,044 A | 12/2000 | Porfano et al. |
| 6,165,153 A | 12/2000 | Kashmer |
| D436,661 S | 1/2001 | Berry |
| 6,200,295 B1 | 3/2001 | Burchett et al. |
| D445,176 S | 7/2001 | Landers |
| 6,270,519 B1 | 8/2001 | Botts |
| D447,797 S | 9/2001 | Odell et al. |
| 6,391,008 B1 | 5/2002 | Tsai |
| D460,820 S | 7/2002 | Niedospial, Jr. |
| D461,243 S | 8/2002 | Niedospial, Jr. |
| 6,432,087 B1 | 8/2002 | Hoeck et al. |
| D462,761 S | 9/2002 | Swenson |
| D463,025 S | 9/2002 | Swenson |
| D463,546 S | 9/2002 | Jansen et al. |
| 6,447,480 B1 | 9/2002 | Brunel |
| D473,646 S | 4/2003 | Baillargeon et al. |
| 6,544,233 B1 | 4/2003 | Fukui et al. |
| 6,684,918 B1 | 2/2004 | Thilly et al. |
| 6,689,106 B2 | 2/2004 | Bush, Jr. et al. |
| 6,752,782 B2 | 6/2004 | Liao |
| D504,512 S | 4/2005 | Fournier |
| 6,883,778 B1 | 4/2005 | Newton |
| D505,200 S | 5/2005 | Simpson et al. |
| 6,972,004 B2 | 12/2005 | La |
| 6,991,618 B2 | 1/2006 | Lau et al. |
| 7,018,089 B2 | 3/2006 | Wenz et al. |
| 7,032,764 B2 | 4/2006 | Viggiano |
| 7,077,829 B2 | 7/2006 | McGuckin, Jr. et al. |
| 7,127,085 B2 | 10/2006 | Kim et al. |
| 7,172,085 B2 * | 2/2007 | Beaudette ............ A61J 9/00 215/11.1 |
| D542,406 S | 5/2007 | Knight et al. |
| D552,773 S | 10/2007 | Greenberg |
| 7,320,678 B2 | 1/2008 | Ruth et al. |
| 7,322,941 B2 | 1/2008 | Henshaw |
| D578,210 S | 10/2008 | Muta et al. |
| D581,048 S | 11/2008 | Kawamura |
| 7,455,661 B2 | 11/2008 | Barrelle et al. |
| D593,801 S | 6/2009 | Wilson et al. |
| 7,628,782 B2 | 12/2009 | Adair et al. |
| 7,658,734 B2 | 2/2010 | Adair et al. |
| 7,686,823 B2 | 3/2010 | Pingleton et al. |
| 7,713,245 B2 | 5/2010 | Cipoletti et al. |
| D618,347 S | 6/2010 | Bradshaw |
| 7,842,217 B2 | 11/2010 | Enns et al. |
| D632,144 S | 2/2011 | Weisenbach |
| 7,879,002 B2 | 2/2011 | Jessop |
| D635,249 S | 3/2011 | Becker |
| 7,951,108 B2 | 5/2011 | Harper et al. |
| 7,955,317 B2 | 6/2011 | Fournie |
| 7,988,683 B2 | 8/2011 | Adair et al. |
| 8,016,795 B2 | 9/2011 | Barrelle et al. |
| D646,531 S | 10/2011 | Murphy |
| D649,242 S | 11/2011 | Kosinski et al. |
| 8,066,670 B2 | 11/2011 | Cluff |

(56) References Cited

U.S. PATENT DOCUMENTS

| | | |
|---|---|---|
| D650,903 S | 12/2011 | Kosinski et al. |
| 8,070,721 B2 | 12/2011 | Kakish et al. |
| 8,075,523 B2 | 12/2011 | Wayman et al. |
| D665,497 S | 8/2012 | Marshall et al. |
| 8,333,693 B2 | 12/2012 | Hamazaki |
| D675,540 S | 2/2013 | Montminy |
| 8,376,988 B2 | 2/2013 | Perovitch |
| 8,398,601 B2 | 3/2013 | Smith et al. |
| 8,465,461 B2 | 6/2013 | Wu et al. |
| 8,491,535 B2 | 7/2013 | Limaye |
| 8,506,549 B2 | 8/2013 | Breuer-Thal et al. |
| D690,417 S | 9/2013 | Solomon |
| 8,540,683 B2 | 9/2013 | Williams, Jr. et al. |
| 8,568,365 B2 | 10/2013 | Reid |
| 8,740,858 B2 | 6/2014 | Kawamura |
| 8,784,377 B2 | 7/2014 | Ranalletta et al. |
| D713,028 S | 9/2014 | Yevmenenko |
| D715,428 S | 10/2014 | Baid |
| 8,870,833 B2 | 10/2014 | Lloyd et al. |
| 8,882,725 B2 | 11/2014 | Davis |
| 8,920,364 B2 | 12/2014 | Berman et al. |
| D721,803 S | 1/2015 | Dubach |
| 8,932,264 B2 | 1/2015 | DeSalvo |
| 8,936,577 B2 | 1/2015 | Lee et al. |
| 8,985,357 B1 | 3/2015 | Strayer et al. |
| 8,992,505 B2 | 3/2015 | Thorne, Jr. et al. |
| D726,305 S | 4/2015 | Furukawa |
| D736,906 S | 8/2015 | Schultz |
| D737,436 S | 8/2015 | Lev et al. |
| D739,524 S | 9/2015 | Zemel et al. |
| 9,149,622 B2 | 10/2015 | Bonnet et al. |
| D743,025 S | 11/2015 | Berler |
| 9,265,898 B2 | 2/2016 | Rajan et al. |
| 9,272,099 B2 | 3/2016 | Limaye et al. |
| 9,308,362 B2 | 4/2016 | Mansour et al. |
| 9,345,638 B2 | 5/2016 | Ferrara |
| 9,408,971 B2 | 8/2016 | Carlyon |
| 9,408,981 B2 | 8/2016 | Cowan |
| 9,433,562 B2 | 9/2016 | Ingram et al. |
| D773,042 S | 11/2016 | Hwang et al. |
| 9,522,237 B2 | 12/2016 | Alheidt et al. |
| D785,162 S | 4/2017 | Swisher et al. |
| 9,656,022 B1 | 5/2017 | Russo |
| D792,969 S | 7/2017 | Taylor |
| 9,814,870 B2 | 11/2017 | Jin et al. |
| 9,814,871 B2 | 11/2017 | Wlodarczyk et al. |
| 9,839,750 B2 | 12/2017 | Limaye et al. |
| 2002/0151851 A1 | 10/2002 | Fu |
| 2002/0173748 A1 | 11/2002 | McConnell et al. |
| 2003/0034264 A1 | 2/2003 | Hamai et al. |
| 2003/0199816 A1 | 10/2003 | Ramming |
| 2004/0238776 A1 | 12/2004 | Peters et al. |
| 2005/0038395 A1 | 2/2005 | Shih |
| 2005/0124935 A1 | 6/2005 | McMichael |
| 2005/0177100 A1 | 8/2005 | Harper et al. |
| 2005/0251096 A1 | 11/2005 | Armstrong et al. |
| 2006/0161106 A1 | 7/2006 | Wu |
| 2006/0189932 A1 | 8/2006 | Yang et al. |
| 2006/0264824 A1 | 11/2006 | Swisher, III |
| 2007/0005014 A1 | 1/2007 | Lin et al. |
| 2007/0123822 A1 | 5/2007 | Wang et al. |
| 2008/0021414 A1 | 1/2008 | Alheidt |
| 2008/0045929 A1 | 2/2008 | Birnbach |
| 2008/0114307 A1 | 5/2008 | Smith et al. |
| 2008/0128646 A1 | 6/2008 | Clawson |
| 2008/0140020 A1 | 6/2008 | Shirley |
| 2008/0183153 A1 | 7/2008 | Enns |
| 2008/0223807 A1 | 9/2008 | Botts |
| 2010/0292673 A1 | 11/2010 | Korogi et al. |
| 2011/0240162 A1 | 10/2011 | Zeyfang |
| 2012/0022457 A1 | 1/2012 | Silver |
| 2012/0029471 A1 | 2/2012 | Lee et al. |
| 2012/0029481 A1 | 2/2012 | Pech |
| 2012/0265150 A1 | 10/2012 | Frey et al. |
| 2012/0323221 A1 | 12/2012 | Gallo et al. |
| 2013/0030379 A1 | 1/2013 | Ingram et al. |
| 2013/0079730 A1 | 3/2013 | Mosler et al. |
| 2013/0090606 A1 | 4/2013 | Shams |
| 2013/0098861 A1 | 4/2013 | Lair et al. |
| 2013/0103002 A1 | 4/2013 | Fruenlund et al. |
| 2013/0144255 A1 | 6/2013 | Cohn |
| 2013/0150797 A1 | 6/2013 | Lesch, Jr. |
| 2014/0207063 A1 | 7/2014 | Hyun et al. |
| 2014/0276442 A1 | 9/2014 | Haughey |
| 2014/0276458 A1 | 9/2014 | Mansour et al. |
| 2015/0005716 A1 | 1/2015 | Adair et al. |
| 2015/0073356 A1 | 3/2015 | Sasayama et al. |
| 2015/0164744 A1 | 6/2015 | Ingram et al. |
| 2015/0224031 A1 | 8/2015 | Methner |
| 2015/0231038 A1 | 8/2015 | Oates, II et al. |
| 2016/0030293 A1 | 2/2016 | Dorsey et al. |
| 2016/0067422 A1 | 3/2016 | Davis et al. |
| 2016/0106928 A1 | 4/2016 | Davis et al. |
| 2016/0159635 A1 | 6/2016 | Davis et al. |
| 2016/0175201 A1* | 6/2016 | Schuessler .......... A61J 15/0092 604/516 |
| 2016/0199591 A1 | 7/2016 | Matsui |
| 2016/0250415 A1 | 9/2016 | Yagi et al. |
| 2016/0279032 A1 | 9/2016 | Davis et al. |
| 2016/0317393 A1 | 11/2016 | Davis et al. |
| 2017/0203045 A1 | 7/2017 | Ivosevic et al. |
| 2017/0312181 A1 | 11/2017 | Davis et al. |

FOREIGN PATENT DOCUMENTS

| | | |
|---|---|---|
| EP | 0148715 A1 | 7/1985 |
| EP | 1110568 A2 | 6/2001 |
| EP | 1447072 A1 | 8/2004 |
| EP | 1980282 A1 | 10/2008 |
| EP | 2269685 A2 | 1/2011 |
| EP | 2583715 A1 | 4/2013 |
| FR | 1126718 A | 11/1956 |
| FR | 2720279 A1 | 12/1995 |
| FR | 2929854 A1 | 10/2009 |
| FR | 2930428 A1 | 10/2009 |
| GB | 2453361 A | 4/2009 |
| WO | 9200717 A1 | 1/1992 |
| WO | 9803210 A2 | 1/1998 |
| WO | 9831410 A1 | 7/1998 |
| WO | 0130415 A2 | 5/2001 |
| WO | 03072162 A2 | 9/2003 |
| WO | 2006052655 A2 | 5/2006 |
| WO | 2011026156 A1 | 3/2011 |
| WO | 2013081699 A2 | 6/2013 |
| WO | 2016116693 A1 | 7/2016 |
| WO | 2016154304 A1 | 9/2016 |
| WO | 2016205626 A1 | 12/2016 |
| WO | 2017011754 A1 | 1/2017 |

OTHER PUBLICATIONS

Carrera, Amy Long, MS, RD, CNSC, CWCMS; Enfit: How to Transition to the New Feeding Tube Connectors; Shield Healthcare, Inc.; Feb. 4, 2015; 5 pgs.

"Enfit Update"; Feeding Tube Awareness Foundation; Feb. 2015; 5 pgs.

"Enteral Connectors: New Standards and Designs"; Pash, Elizabeth MS, RD, LDN; DNS Symposium; Baltimore, Maryland; Jun. 2015; 32 pgs.

Guide to New Enteral Feeding Connections; Covidien; Dec. 31, 2015; 4 pgs.

International Search Report & Written Opinion for PCT/US2011/051338; dated Dec. 14, 2011; 20 pgs.

International Search Report & Written Opinion for PCT/US2016/023771; 17 pgs; dated Jun. 27, 2016.

International Search Report & Written Opinion for PCT/US2016/042248; dated Sep. 21, 2016; 10 pgs.

International Search Report & Written Opinion for PCT/US2017/042559; dated Dec. 7, 2017; 21 pgs.

International Search Report & Written Opinion for PCT/US2017/043747; dated Nov. 2, 2017; 14 pgs.

(56) References Cited

OTHER PUBLICATIONS

Invitation to Pay Additional Fees for PCT/US2017/042559; dated Oct. 16, 2017; 15 pgs.
10 ml Liquid Medicine Dispenser / Oral Syringe with Filler Tube; 1 pg; date unknown.
Alternative Syringes Low Displacement Option PowerPoint Presention; Presented by Rork Swisher of Covidien; ISO 80369 Series Meeting; Berlin Germany; 11 pgs; Mar. 19, 2014.
Bostik Evo-Stik Adhesive Express Syringe; www.amazon.co.uk/Bostik-808546-Evo-Stik-Adhesive-Express/dp/8006O6DMFO; 1 pg; date unknown.
Brazilian Peel Syringe Applicator; www.amazon.com/Brazilian-Peel-Applications/dp/B003IIUN6W/ref=cm_cr_pr_product_top?ie=UTF8; 1 pg; date unknown.
Slap-Shot Flexible Oral Doser; 1 pg; date unknown.
Sulzer Dosing Syringe with Piston; www.directindustry.com/prod/sulzer-chemtech/product-28889-903259.html; 1 pg; date unknown.
Vygon Sales Sheet; 2014 (2 pgs).
Written Opinion for PCT/US2016/042248; dated Jul. 11, 2017; 8 pgs.
Invitation to Pay Additional Fees for PCT/US2017/052321; Dec. 4, 2017; 10 pgs.
J-B Weld Epoxy Springe; www.lowes.com/pd_556898-81288-50112_0_?productID=50149636; 1 pg. date unknown.
Contentions of Medela LLC in letter [redacted] dated Sep. 18, 2017; 3 pgs.
Medi-Pals Oral Medication Dispenser; 1 pg; Jun. 19, 2012.
MediPop 3 in 1 Pacifier; 1 pg; date unknown.
NeoMed Enteral Syringe; 2007 (8 pgs).
Premier Safety Institute; New Enteral Feeding Products with ENFit Connectors: Implementation Timeline Delayed; SafetyShare; Jun. 18, 2015; 2 pgs.
Oral Medication Dispenser; 1 pg; Jun. 19, 2012.
Oral Medication Nurser; 1 pg; Oct. 6, 2006.
ISO 80369-3, Small Bore Enteral Connector Standards; 3 pgs; Jul. 21, 2014.
ENFit Female Connector; 1 pg; date unknown.
ENFit Male Connector; 1 pg; date unknown.
International Search Report & Written Opinion for PCT/US2015/048382; dated Nov. 5, 2015; 11 pgs.
New ISO Tubing Connector Standards: A Follow-Up to the Sentinel Event Alert Webinar PowerPoint Presention; www.jointcommission.org; 50 pgs; Dec. 3, 2014.
New Tube Feeding Connectors Webinar PowerPoint Presention; www.oley.org; 24 pgs; Jun. 24, 2014.
StayConnected2014 Informational Bracelet; 1 pg; date unknown.
http://www.stayconnected2014.org/get-ready.html; 1 pg; date unknown.

* cited by examiner

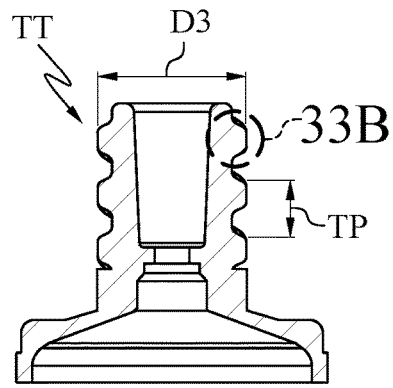 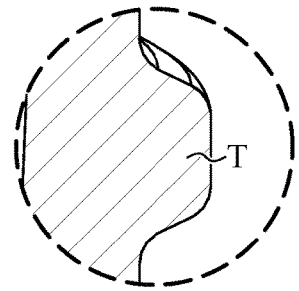
FIG. 33A          FIG. 33B
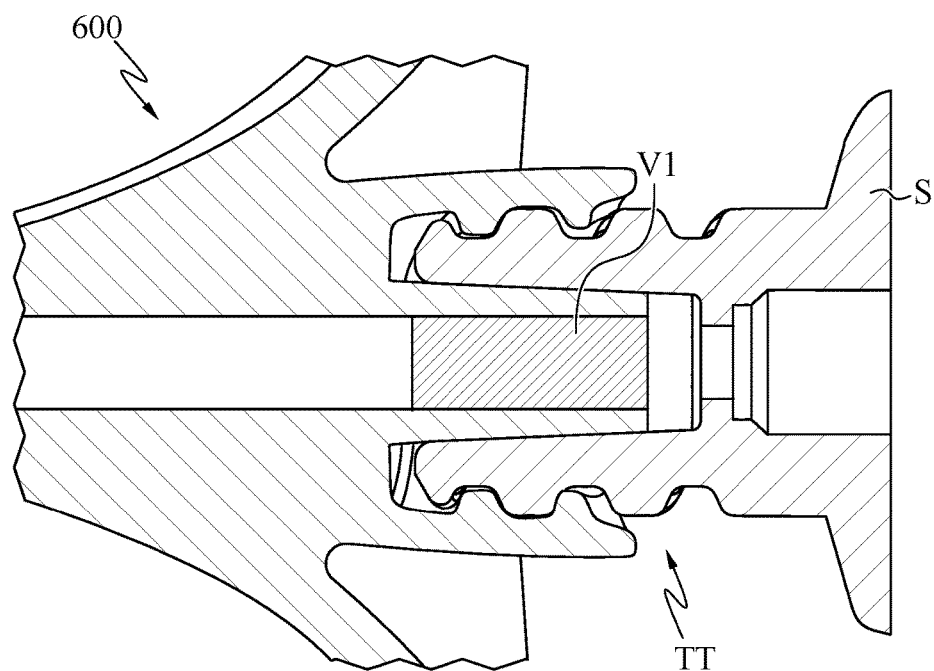
FIG. 34

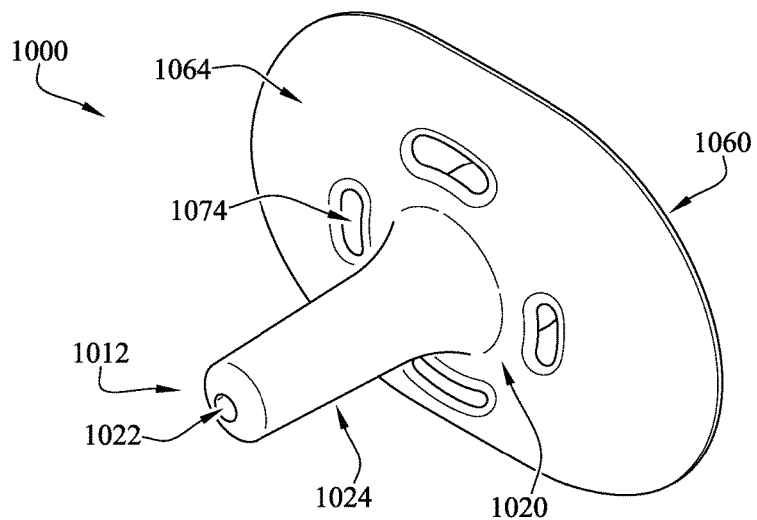
FIG. 40
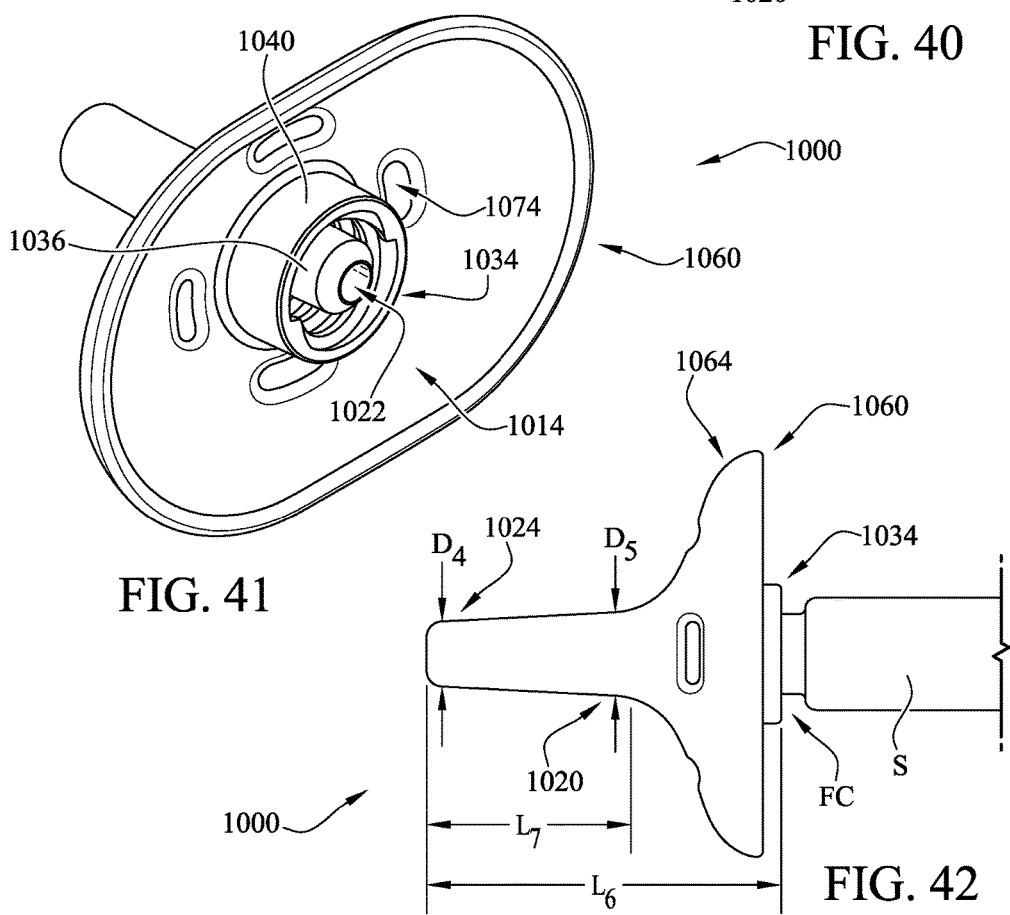
FIG. 41
FIG. 42

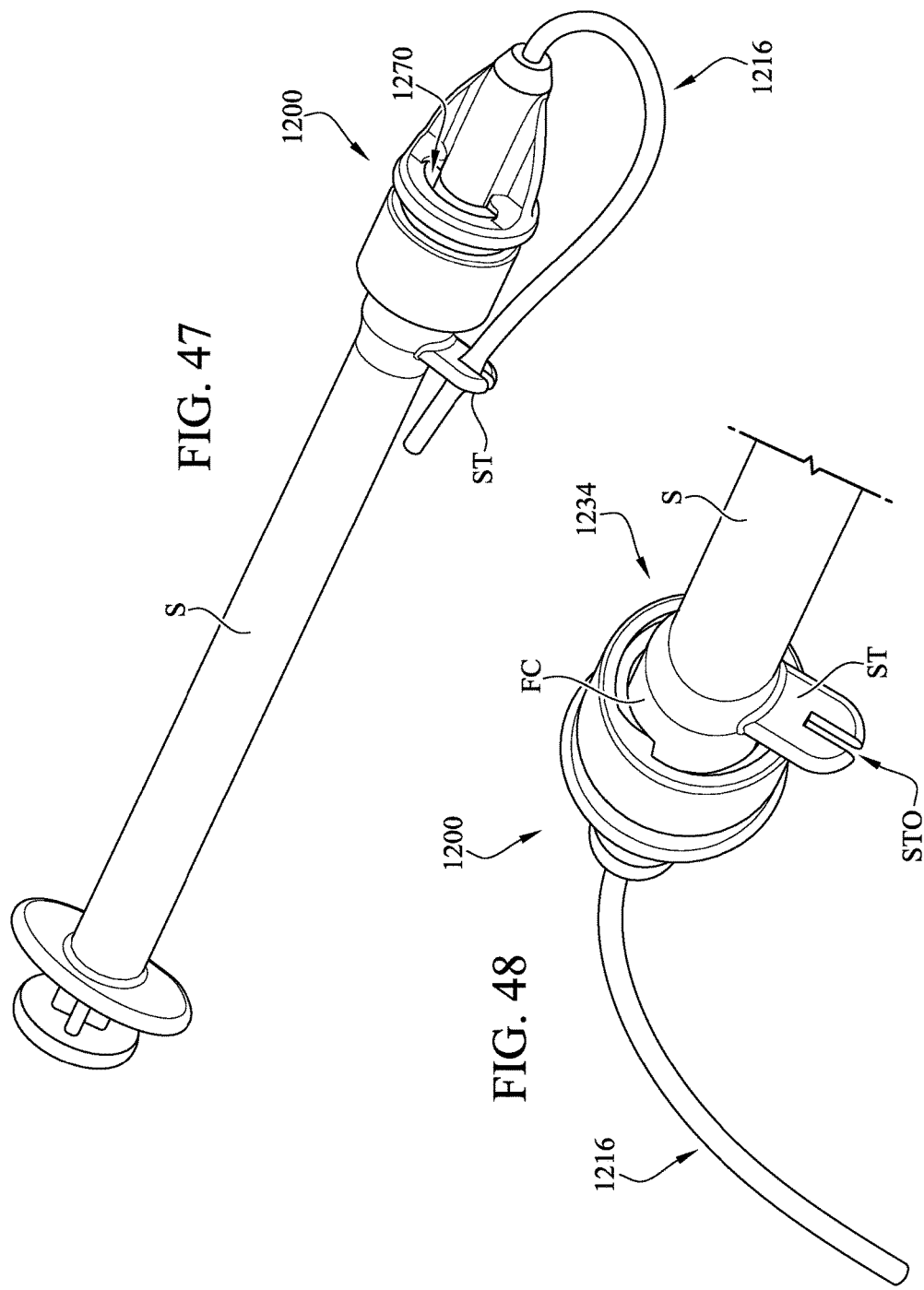

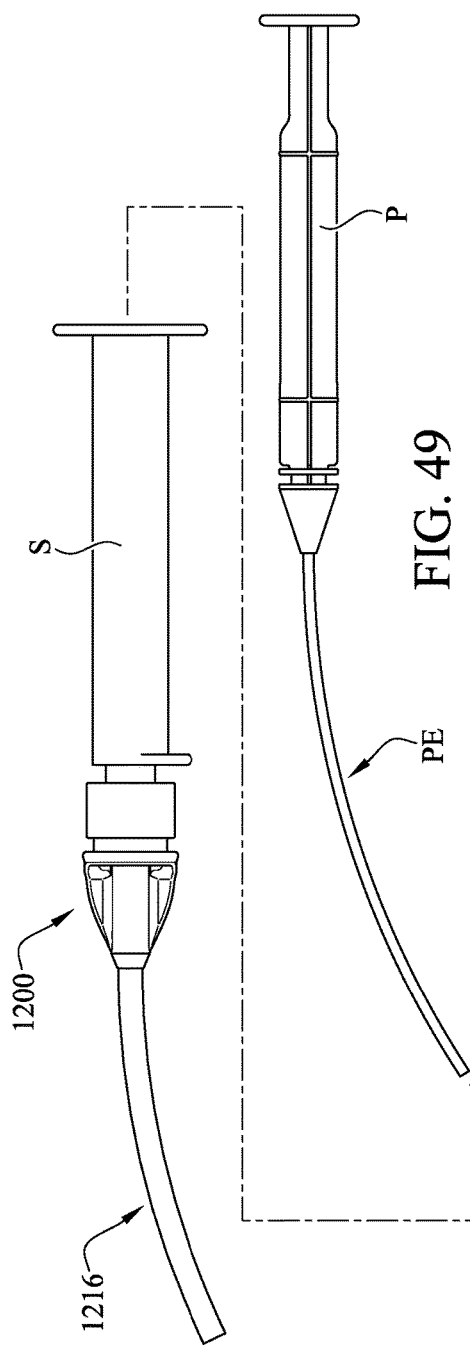
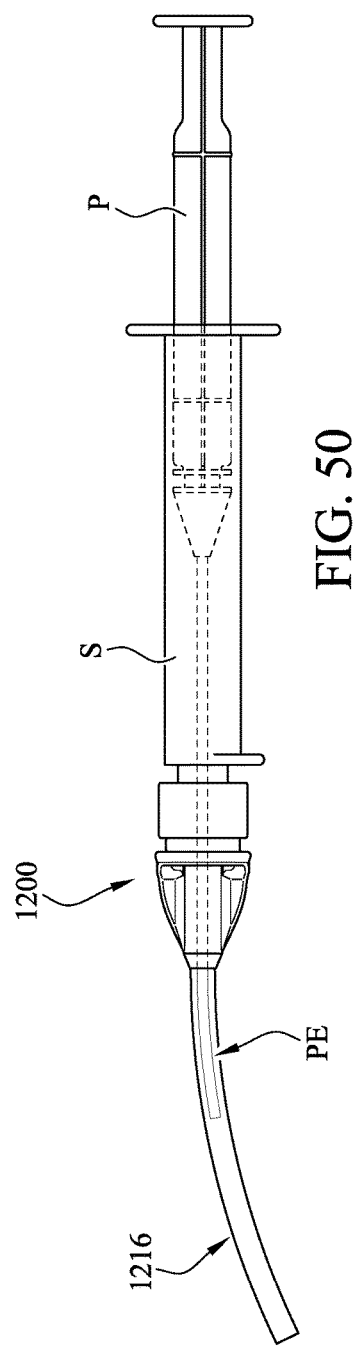

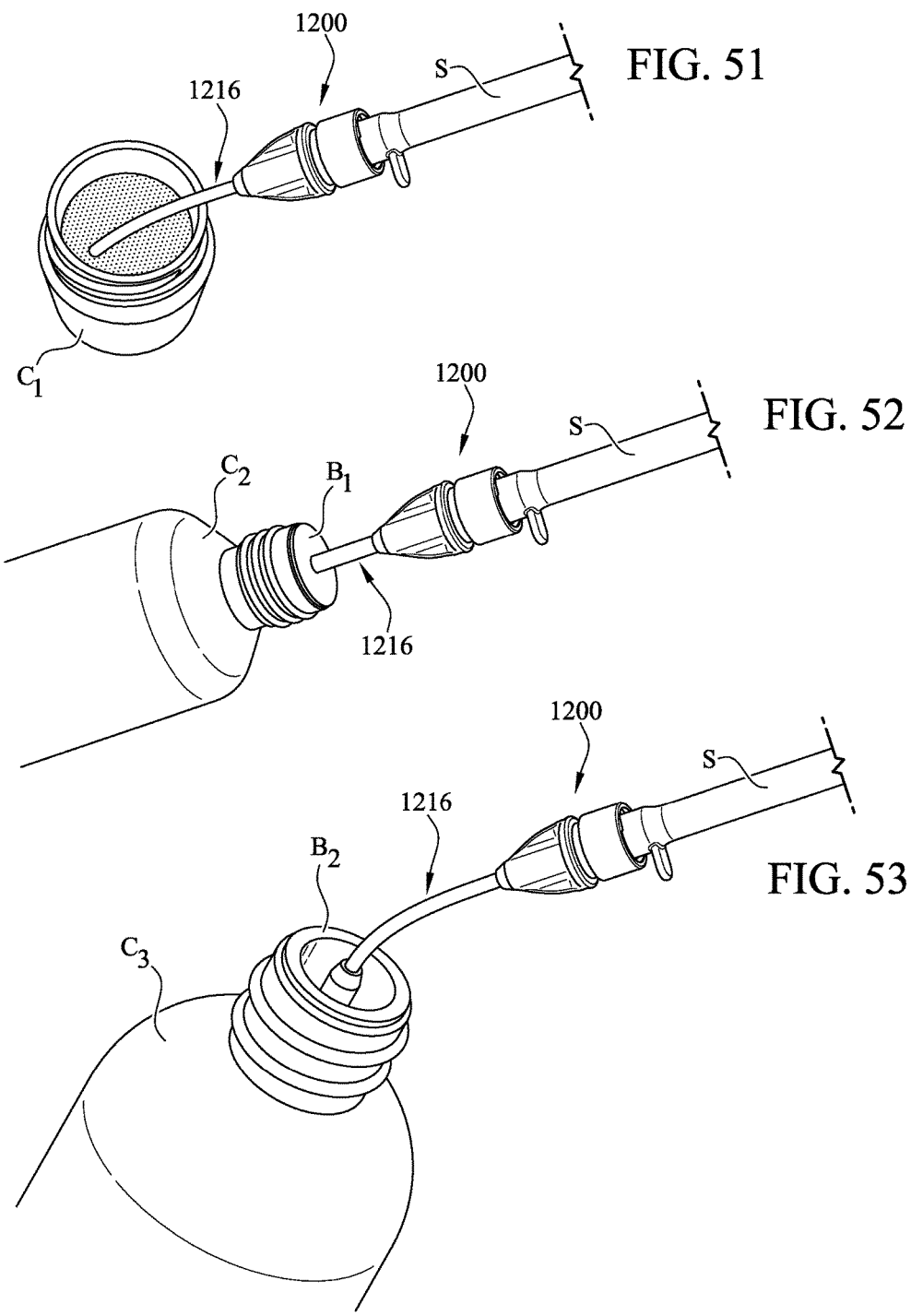

| | | PRIMING VOLUME (mL) | |
|---|---|---|---|
| | TUBE LENGTH | CUBIC mm | CUBIC ml |
| 4Fr ID (1.35mm) | 30mm | 43 | 0.043 |
| | 40mm | 57 | 0.057 |
| | 60mm | 86 | 0.086 |
| | 100mm | 143 | 0.143 |

| | | | |
|---|---|---|---|
| 4Fr FEEDING TUBE ID (0.6mm) | 30mm | 8.5 | 0.008 |
| | 40mm | 11.3 | 0.011 |
| | 60mm | 17.0 | 0.017 |
| | 100mm | 28.3 | 0.028 |

| | | | |
|---|---|---|---|
| MAX ID TO MAINTAIN 0.1mL PV | 30mm | 1.03 | |
| | 40mm | 0.89 | |
| | 60mm | 0.73 | |
| | 100mm | 0.56 | |

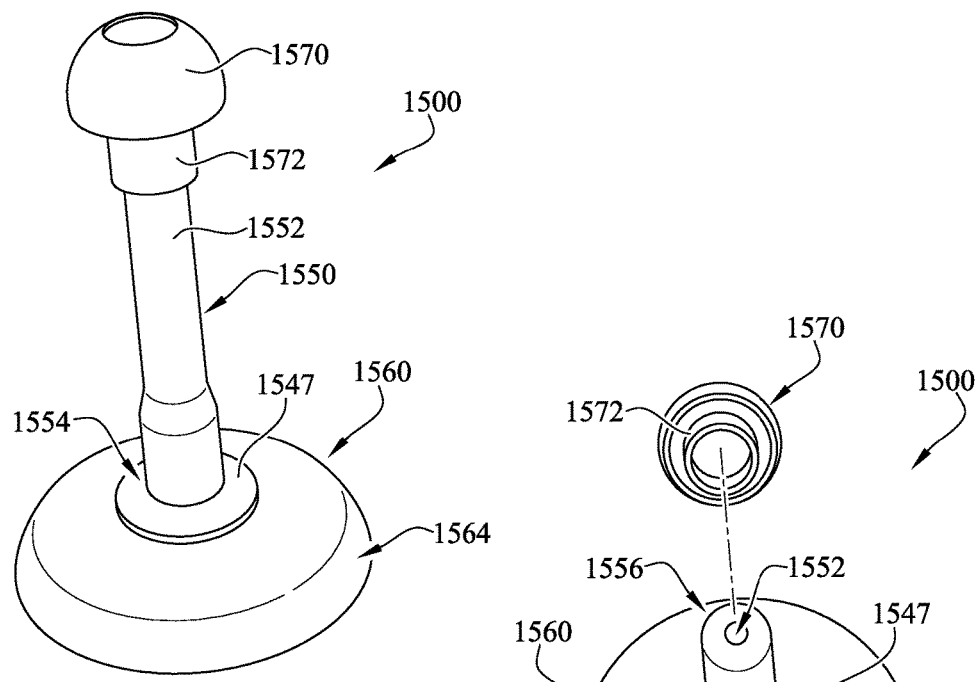
FIG. 61
FIG. 62
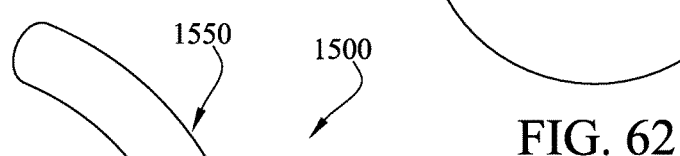
FIG. 63

ORAL ADMINISTRATION COUPLER FOR BACK-OF-MOUTH DELIVERY

CROSS-REFERENCE TO RELATED APPLICATIONS

This application is a divisional of U.S. Non-Provisional patent application Ser. No. 15/652,742 filed Jul. 18, 2017, which claims the priority benefit of U.S. Provisional Patent Application Ser. No. 62/396,532 filed Sep. 19, 2016 and U.S. Provisional Patent Application Ser. No. 62/363,498 filed Jul. 18, 2016; U.S. Non-Provisional patent application Ser. No. 15/652,742 filed Jul. 18, 2017 is also a continuation-in-part of U.S. Non-Provisional patent application Ser. No. 15/078,674 filed Mar. 23, 2016, which claims the priority benefit of U.S. Provisional Patent Application Ser. No. 62/137,293 filed Mar. 24, 2015 and U.S. Provisional Patent Application Ser. No. 62/192,726 filed Jul. 15, 2015, all of which are hereby incorporated herein by reference for all purposes.

TECHNICAL FIELD

The present invention relates generally to the field of containment, storage, and delivery of fluids, particularly in the medical and pharmaceutical fields, and more particularly to a coupler for devices used in oral administration of medical or nutritional fluids.

BACKGROUND

Various fluids such as medications and nutritional fluids are delivered to human or animal patients by dispensing from a syringe. Syringes conforming to the new ENFit® enteral design standard (ISO 80369-3) may include nipple or tip couplings of larger dimension and volume or displacement than previous syringes. Volumetric differences in fluid delivery resulting from these changes may adversely affect accuracy of dosing in the oral administration of fluids. Furthermore, the ISO 80369-3 standard represents a greater risk of mouth trauma given the larger dimension syringe tips and threaded connectors.

Thus it can be seen that needs exist for improvements to oral administration couplers for fluid delivery and for providing a means to orally dose or dispense from the syringes conforming to the ISO 80369-3 enteral design standard, and to mitigate trauma to the mouth and provide accurate means of delivering an oral dose from an ISO 80369-3 formatted syringe. It is to the provision of improved oral administration couplers meeting these and other needs that the present invention is primarily directed.

SUMMARY

In example embodiments, the present invention provides an improved oral administration coupler for delivery of fluids such as medications and nutritional fluids. The invention further includes improved methods of design and manufacture of fluid delivery devices, including determining and controlling lumen size(s) and fluid flow path volume(s) so that the devices deliver accurate and consistent doses or quantities of fluid. Devices and methods according to the invention provide fluid volume paths or segments having the same or closely similar fluid delivery volume across a plurality of fluid delivery devices or accessories, for accurate and consistent dosing or fluid delivery quantities. For example, the fluid volume path of an oral administration coupler according to example forms of the invention has the same volume in the coupler as a male ENFit connector, at its nominal engagement depth.

In one aspect, the present invention relates to an oral administration coupler for delivering fluids from a syringe having a female connector to a cheek area of a child or infant. The oral administration coupler includes a conduit and a generally circumferential flange extending outwardly from the conduit. The conduit generally extends from a first end to a second end. The first end includes a generally elongate member for oral insertion to deliver fluids to the cheek area of the child or infant, and the second end includes an ENFit compatible fitting for removable engagement with the female connector of the syringe. The flange extending outwardly from the conduit is generally positioned between the first and second ends of the conduit.

In another aspect, the invention relates to an oral administration coupler including a central fluid transfer member, a lumen defined within the fluid transfer member, and a flange. The fluid transfer member generally includes a first end, a generally opposite second end, and an outer periphery. The lumen is defined within the central fluid transfer member and extends from the first end to the second end. The flange is generally positioned between the first and second ends of the fluid transfer member, and wherein the flange generally extends outwardly from an outer periphery of the central fluid transfer member.

In example embodiments, the first end of the central fluid transfer member includes a generally elongate stem having a substantially oval cross sectional shape. In one form, the generally elongate stem is generally duckbilled in shape. According to one form, the second end of the central fluid transfer member comprises an ENFit compatible coupling having a centrally-positioned transfer port and an outer collar comprising an internally threaded portion. Preferably, the ENFit compatible coupling is configured for removable engagement with a female connector of a syringe.

Optionally, the second end of the central fluid transfer member comprises a coupling having a centrally-positioned transfer port and an outer collar comprising an internally threaded portion. Preferably, the coupling is configured for removable engagement with a syringe having a threaded tip. In example forms, the threaded tip generally has an outer diameter and a thread pitch, the outer diameter being between about 4 to about 9 millimeters and the thread pitch being between about 1 millimeter to about 5 millimeters. In some example forms, the outer diameter is about 6.675 millimeters and the thread pitch is about 2.450 millimeters.

In still another aspect, the invention relates to an oral administration coupler for delivering fluids from a syringe to a cheek area of a child or infant. In example forms, the syringe has a threaded tip having an outer diameter of between about 4 millimeters to about 9 millimeters and a thread pitch of between about 1 millimeter to about 5 millimeters. The oral administration coupler generally includes a conduit and a flange. The conduit generally extending from a first end to a second end, wherein the first end includes a generally elongate oral delivery applicator for oral insertion to deliver fluids to the cheek area of the child or infant, and wherein the second end includes a coupling for removable engagement with the threaded tip of the syringe. The flange generally extends outwardly from the conduit and is generally positioned between the first and second ends of the conduit.

In yet another aspect, the invention relates to a method of designing a fluid delivery device including calculating a volume of at least a portion of a fluid delivery path of a first fluid delivery device; and designing a fluid delivery path of a second fluid delivery device to substantially match the fluid delivery path volume of the first fluid delivery device. In example forms, the first fluid delivery device includes a pharmacy coupler for transferring fluids from a container to a syringe. According to one example form, the second fluid delivery device includes an oral administration coupler for delivering fluids from a syringe to a cheek area of a child or infant.

In another aspect the invention relates to an oral administration coupler for delivering fluids from a syringe to a child or infant. The oral administration coupler includes a coupling having an ENFit compatible coupling end and an applicator coupling end, and a conduit extending therebetween. An elongate tube is provided and includes a first end coupled to the applicator coupling end and a second end generally oppositely extending therefrom. In example embodiments, the syringe includes a female coupler. According to one example embodiment, the female connector of the syringe further includes a lumen extension tip axially extending therein.

In yet another aspect, the invention relates to an oral administration coupler for back-of-mouth delivery including a central fluid transfer member having a first end, a generally opposite second end, an outer periphery, and lumen defined within the central fluid transfer member and extending from the first end to the second end. In example embodiments, the central fluid transfer member defines a length between the first and second ends sufficient to deliver fluid from the central fluid transfer member to a back of a child's mouth from a fluid delivery device at least partially external of the child's mouth.

In yet another aspect, the invention relates to an oral administration coupler for delivering fluids from a syringe to a child or infant. The syringe includes a female connector having a lumen extension tip extending in a coaxial and concentric relationship with respect to the female connector of the syringe. The oral administration coupler includes a conduit and a flange. The conduit extends from a first end to a second end, wherein the first end includes an applicator for oral insertion to deliver fluids to the child or infant, and the second end includes an ISO 80369-3 formatted coupling for removable engagement with the female connector of the syringe, and wherein the lumen extension tip is received within the conduit of the ISO 80369-3 formatted coupling when the female coupling is connected therewith. The flange extends outwardly from the conduit and is positioned between the first and second ends of the conduit. According to one example embodiment, the flange is generally non-circular in shape and includes a plurality of openings.

BRIEF DESCRIPTION OF THE DRAWINGS

FIG. 33A is a cross-sectional view of a portion of one of the syringes taken along line 33A-33A of FIG. 32.

FIG. 33B is a detailed view of a thread portion of the syringe portion of FIG. 31A.

FIG. 34 is a cross-sectional view of the oral administration coupler removably engaged with the syringe as shown in FIG. 31.

FIG. 40 shows a front perspective view of an oral administration coupler according to another example embodiment of the present invention.

FIG. 41 shows a rear perspective view of the oral administration coupler of FIG. 40.

FIG. 42 shows a side view of the oral administration coupler of FIG. 40 coupled with a syringe according to an example embodiment of the present invention.

FIG. 47 is a side perspective view of the oral administration coupler of FIG. 45 coupled to a syringe according to another example embodiment of the present invention, and showing a portion of the syringe providing an attachment for receiving at least a portion of the feeding tube extending from the oral administration coupler.

FIG. 48 is a rear perspective view of the oral administration coupler and coupled syringe of FIG. 47.

FIGS. 49-50 show the oral administration coupler of FIG. 45 coupled with a syringe and movable plunger according to another example embodiment of the present invention.

FIG. 51 shows an oral administration coupler and syringe assembly being used to draw fluids into the syringe body from an open vessel according to an example embodiment of the present invention.

FIG. 52 shows an oral administration coupler and syringe assembly being used to draw fluids into the syringe body from a pharmacy bottle and through an enteral-only bottle adapter according to an example embodiment of the present invention.

FIG. 53 shows an oral administration coupler and syringe assembly being used to draw fluids into the syringe body from a pharmacy bottle and through an ENFit compatible bottle adapter according to an example embodiment of the present invention.

FIG. 61 shows a perspective view of an oral administration coupler according to another example embodiment of the present invention, and showing a cap secured to a tip of a tube or applicator extending therefrom.

FIG. 62 shows a top perspective view of the oral administration coupler of FIG. 61, and showing the cap removed from the applicator.

FIG. 63 shows a perspective view of the oral administration coupler of FIG. 61, and showing the flexibility of the applicator.

DETAILED DESCRIPTION OF EXAMPLE EMBODIMENTS

Figure 1:
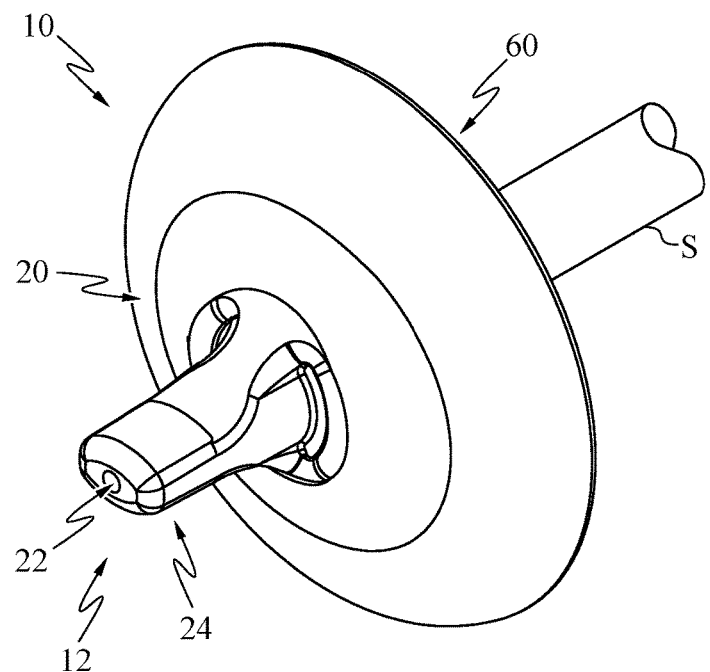
FIG. 1 shows a front perspective view of an oral administration coupler according to an example embodiment of the present invention, and further shows a syringe removably coupled thereto for dispensing contents from the syringe and through the oral administration coupler.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, the present invention relates generally to an oral administration coupling for attachment to a connector of a syringe. In some example forms, the connector of the syringe comprises an ENFit connector, for example, a female connector FC in the form of an ENFit female connector according to the global design standard ISO 80369-3. In other example embodiments, the connector of the syringe comprises a threaded tip.

Figure 2:
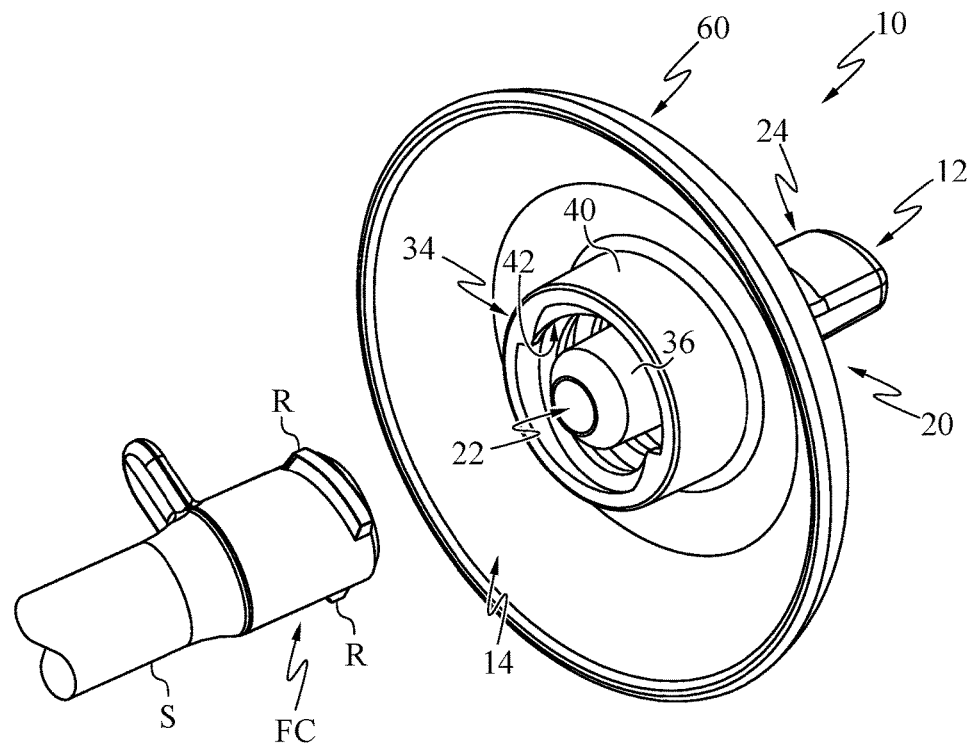
FIG. 2 shows a rear perspective view of the oral administration coupler of FIG. 1, and showing the syringe removably disengaged therefrom.

With respect to the ENFit connector, the female connector FC comprises a pair of thread lugs or ribs R extending along a portion of the periphery of the connector (see FIG. 2). Preferably, the oral administration coupling (as several embodiments will be described below) provides for removable engagement with the female connector FC. Typically, as will be described below, the coupling comprises a collar having a threaded internal portion for removable engagement with the ribs R of the female connector FC. Optionally, in other example embodiments, the coupling can be in the form of a non-threaded, slip-fit connection.

FIGS. 1-7 show an oral administration coupler 10 according to an example embodiment of the present invention. As depicted, the oral administration coupler 10 generally comprises a central fluid transfer member 20 extending from a first end 12 to a second end 14, and an outer flange 60 generally positioned between the first and second ends 12, 14 of the central fluid transfer member 20 and extending outwardly therefrom.

Figure 7:
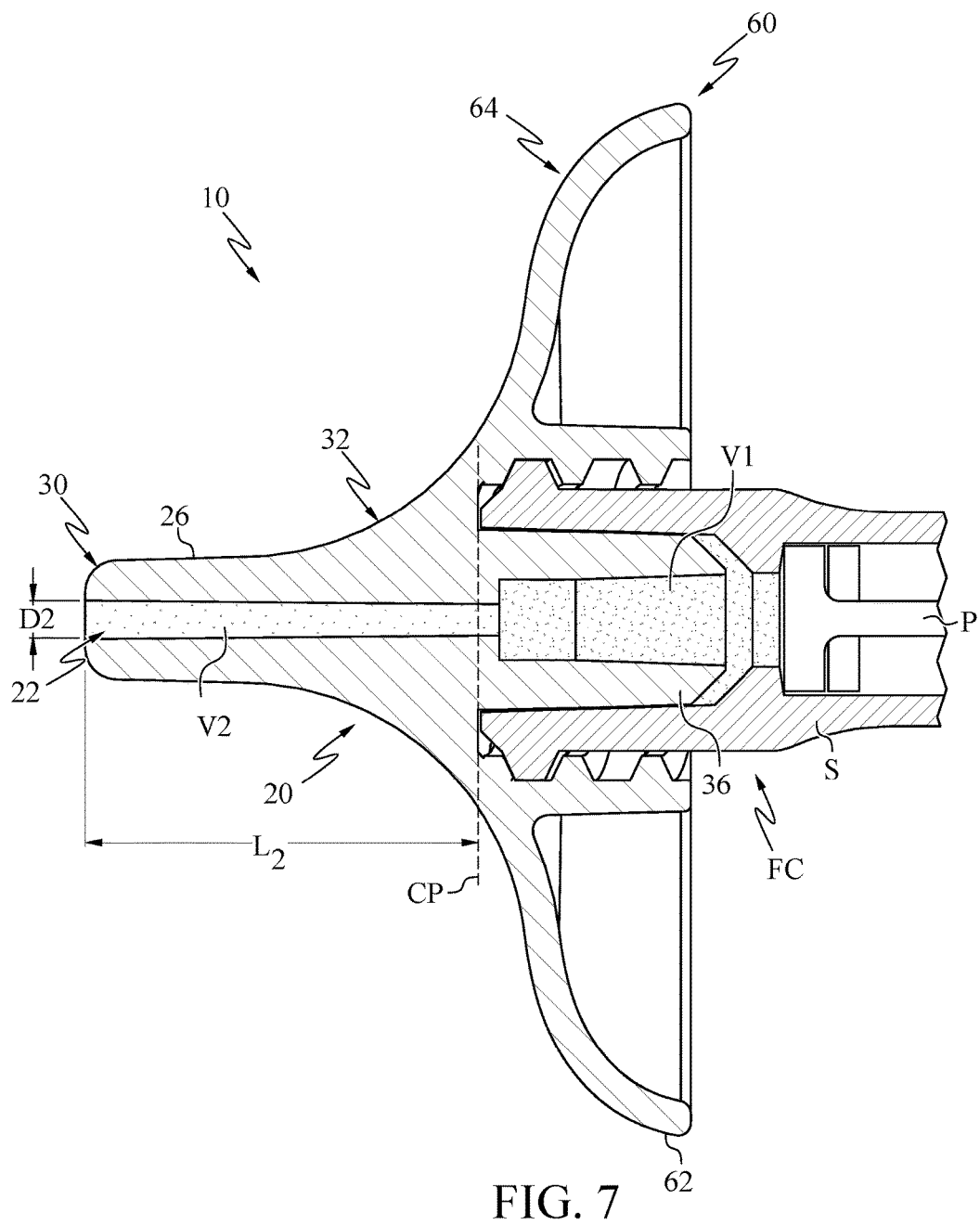
FIG. 7 shows a cross-sectional view of the oral administration coupler removably coupled with the syringe of FIG. 1.

The central fluid transfer member 20 generally comprises an elongate stem or oral delivery applicator 24 at the first end 12 of the fluid transfer member 20 and an ENFit compatible coupling or connector 34 positioned at the second end 14 of the fluid transfer member 20. In example forms, the oral delivery applicator 24 generally extends in a direction that is substantially opposite to the direction of the extension of the connector 34. The flange 60 is generally integrally formed with the fluid transfer member 20 between the first and second ends 12, 14 of the fluid transfer member 20. As shown in FIGS. 2 and 7, the female connector FC of the syringe S is preferably configured for removable coupling and sealing engagement with the coupling 34, for example, so that fluids within the syringe S can be transferred through the coupling 10 and orally administered to a human or animal patient by actuation of a plunger P movably mounted within the syringe S. Preferably, a lumen 22 is provided within the fluid transfer member 20 and extends between the first and second ends 12, 14, for example, through the entirety of both the oral delivery applicator 24 and the ENFit compatible coupling 34, providing fluid communication from the inlet end 14 of the coupler 10 at the syringe S, to the outlet end 12 of the coupler at the delivery applicator 24.

Figure 3:
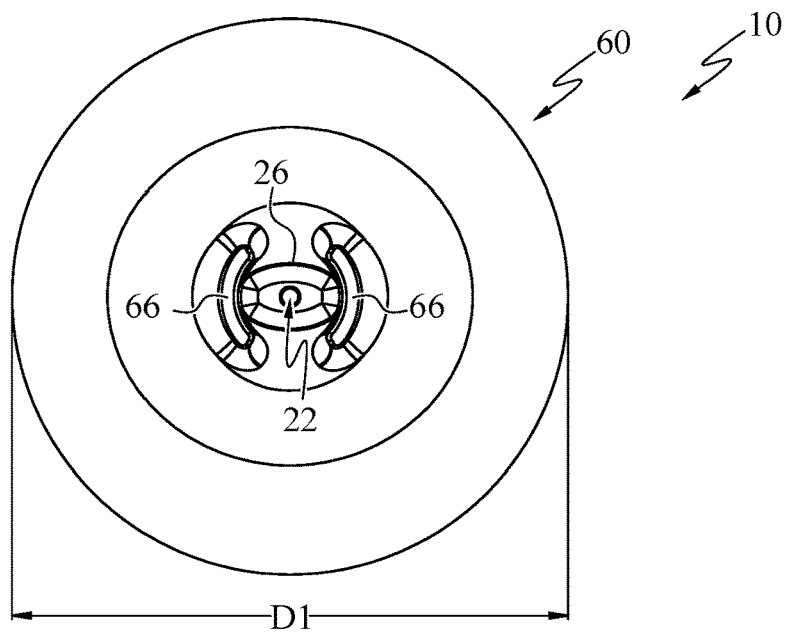
FIGS. 3-6 show several views of the oral administration coupler of FIG. 1.
Figure 4:
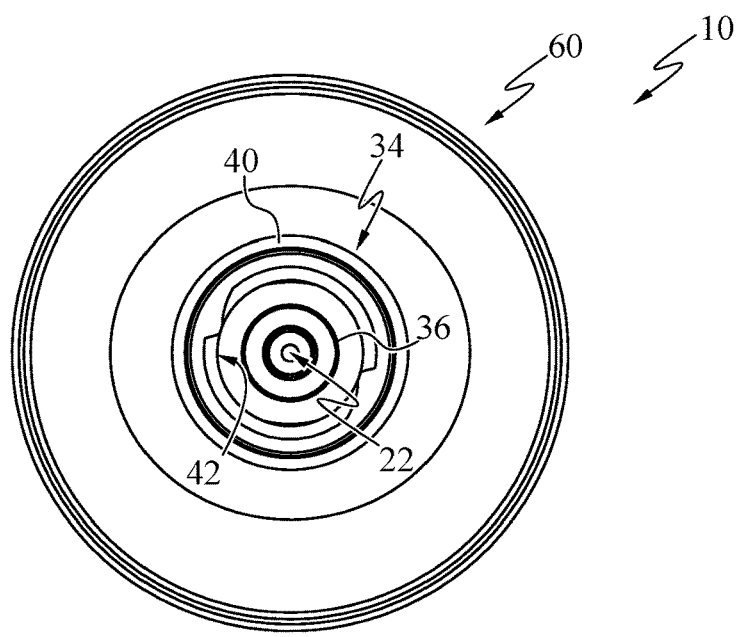
Figure 5:
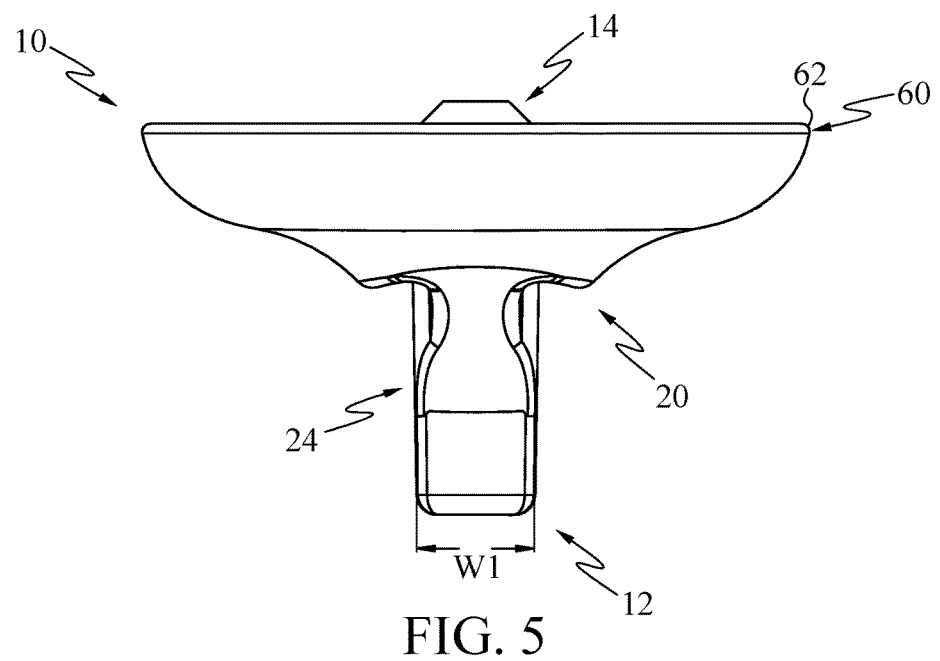

In example embodiments, the oral delivery applicator 24 is generally in the form of an irregular or asymmetric nipple, which is generally duckbilled in shape and has a generally non-circular or oval cross-section (see FIG. 3). For example, in example forms, the applicator 24 generally comprises a width $W_1$ that is generally greater than its height or thickness $T_1$ (see FIGS. 5-6). In some example forms, the width $W_1$ is generally between about 3.5 millimeters to about 6.5 millimeters, more preferably about 5.814 millimeters, and the thickness $T_1$ is generally between about 2 millimeters to about 5 millimeters, more preferably about 3.814 millimeters. Optionally, the applicator 24 can be shaped as desired, for example, extending generally linearly, curved, arcuate, hooked or otherwise extending as desired, having the shape of a rounded cylinder or flattened cylinder, and can be symmetric or asymmetric. Furthermore, the cross-sectional shape can be generally oval, ellipse, generally circular, or otherwise shaped as desired. According to some example forms, the applicator 24 comprises a substantially smooth outer periphery 26 having a generally radiused end 30 defined at the first end 12 of the fluid transfer member 20 and a generally radiused transition 32 defined between the applicator 24 and the flange 60 (see FIG. 6).

Referring back to FIG. 2, the ENFit compatible coupling 34 generally comprises a central transfer port 36 that is generally centrally positioned within an outer collar member 40. In example forms, the outer collar member 40 comprises an internally threaded portion 42 for providing removable engagement with the ribs R of the female coupling FC (see FIGS. 2 and 7). The lumen 22 is generally axially positioned with the transfer port 36, which extends from the second end 14 near the port 36 to the first end 12 near the end of the oral delivery applicator 24. Optionally, in some example forms, the coupling 34 only comprises the central transfer port, for example, such that the coupling 34 is in the form of a non-threaded, slip-fit connector. In example forms, the coupling 34 of the oral administration coupler 10 forms a fluid-tight, leak-proof seal with the female coupling FC of the syringe S, for fluid delivery from the syringe through the oral administration coupler.

In example embodiments, the oral administration coupler 10 is preferably sized and shaped to provide for oral insertion and dispensing of fluids near the cheek area of a child or infant. Furthermore, the flange 60 of the oral administration coupler 10 is generally sized to be substantially large for preventing a child or infant from choking on the coupling. According to one example form, the oral delivery applicator 24 defines a length $L_1$ extending between the first and second ends 12, 14 thereof, and the flange 60 defines an outer periphery 62 defining a diameter $D_1$ (see FIGS. 3 and 6). According to example forms, the length $L_1$ is generally between about 15 to about 35 millimeters, more preferably about 25 millimeters, and about 20.350 millimeters according to one example embodiment. The diameter $D_1$ of the flange 60 is generally between about 20 millimeters to about 40 millimeters, more preferably about 30 millimeters, and about 32.835 millimeters according to one example embodiment. Optionally, according to additional example embodiments of the present invention, the length $L_1$ and the diameter $D_1$ can be chosen as desired.

Figure 6:
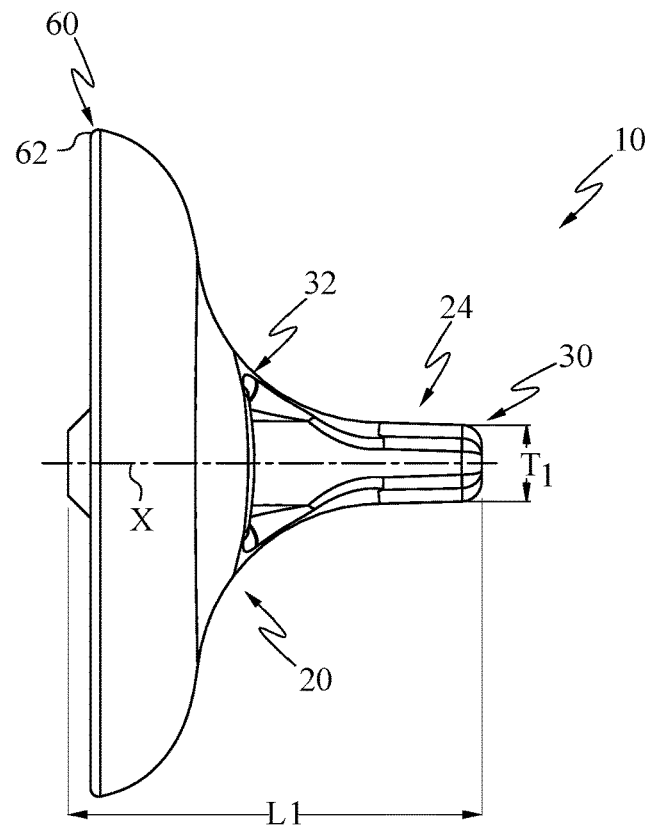

As depicted in FIG. 6, the central transfer port 36 generally extends beyond the flange 60. However, according to other example embodiments of the present invention, the central transfer port 36 can be shortened (or the flange 60 can be extended) such that the central transfer port 36 is generally recessed within the flange 60.

In the depicted embodiment, the flange 60 is generally circular in shape and projects generally outwardly and radially from the central fluid transfer member 20, for example, so as to form a generally circular skirt-like flange extending from the fluid transfer member 20. As described above and shown in FIG. 7, the flange 60 comprises the radiused transition 32 formed with the oral delivery applicator 24, and an outer portion of the flange 60 generally comprises a radiused surface profile 64 that extends to the outer periphery 62. Preferably, the transitions, contours or other geometrical shapes of the flange 60 can be chosen as desired. In some example forms, the flange 60 generally comprises an undulating profile having one or more peaks and valleys, or a portion of one or both. Preferably, the flange 60 substantially shields the connection of the coupler 10 with the syringe S, for example, so as to substantially prevent the connection from being exposed to the human or animal patient receiving the fluids from the syringe. Preferably, the radiused surface profile (including the radiused transition 32) provides for a comfortable contact surface with the patient, for example, when the applicator 24 is inserted to deliver the fluids.

In some example forms, one or more insets, indents or recesses 66 can be formed with the flange 60. For example, as shown in FIGS. 1, 3, 5 and 6, the a pair of generally radially-shaped recesses 66 are formed within a portion of the flange 60 generally near the radiused transition 32, for example, generally positioned between the oral delivery applicator 24 and the flange 60. In some forms, the recesses 66 act as mold reliefs such that the oral administration coupler 10 can be appropriately molded, for example, by plastic injection molding. Alternatively the recesses 66 can serve as vents or suction relief ports.

In example forms, the ENFit female coupling FC is substantially large (size and volume-wise) relative to known couplings, and thus, when withdrawing and dispensing a liquid medication or nutrients to/from the syringe, it is highly probable that a substantially large discrepancy lies between the amount of liquid filled into the syringe relative to the amount of liquid dispensed therefrom, thereby altering the accuracy of the dosage. In some forms, for example when dealing with small doses, a small volume difference may result in 15% or more in the dose difference.

In some example forms, a pharmacy coupler is used to fill the syringe, which has a male tip that displaces the volume of the syringe tip. Preferably, the volume of the oral administration coupling generally matches the volume displaced by the pharmacy coupler, thereby ensuring that the volume of the dose delivered from the oral administration coupling is the volume of the dose filled within the syringe. Thus, according to one form, the lumen size is controlled such that the administered dose is accurate. In example forms, the invention optionally includes a multi-component enteral fluid dispensing and delivery system, for example comprising any two or more of a pharmacy coupler, a syringe, a closure cap, and/or an oral administration coupler, for example according to any of the forms disclosed herein.

In preferred forms, the fluid volume path is substantially the same volume in the female coupling FC as the male ENFit connector or male coupling portion extending from within a portion of the presently claimed coupling. For example, as depicted in FIG. 7, a volume $V_1$ is defined within the female coupling FC and within a portion of the lumen 22 of the coupling, which is generally about 60 mm$^3$. Optionally, the volume defined therein can be between about 40 mm$^3$ to about 70 mm$^3$, more preferably about 50 mm$^3$. As such, a volume $V_2$ is defined within the lumen 22 generally extending through the delivery applicator 24, which comprises a length $L_2$ and a diameter $D_2$. Preferably, the volume $V_1$ is substantially similar to the volume $V_2$, for example, which is generally between about ±1 mm$^3$. For example, the length $L_2$ is defined between the first end 12 and the end of the female connector FC or a cut-off plane CP. In some example forms, the lumen 22 adjacent the applicator 24 comprises a substantially uniform diameter $D_2$, which defines the volume $V_2$. Optionally, the lumen can comprise some taper or draft such that the diameter of the lumen 22 varies along the length $L_2$.

According to example forms, the length $L_2$ of the lumen 22 within the applicator 24 can be chosen as desired, for example, which will affect the diameter $D_2$ (and length $L_1$) to ensure the volume $V_2$ is substantially similar to the volume $V_1$. According to example forms, the length $L_2$ can generally be between about 20 millimeters to about 50 millimeters and generally comprise the volume $V_2$ of about 60 mm$^3$. For example, according to example forms, when the length $L_2$ is about 20 millimeters, the diameter $D_2$ is about 1.95 millimeters and the volume $V_2$ is about 59.7 mm$^3$; when the length $L_2$ is about 25 millimeters, the diameter $D_2$ is about 1.75 millimeters and the volume $V_2$ is about 60.13 mm$^3$; when the length $L_2$ is about 30 millimeters, the diameter $D_2$ is about 1.60 millimeters and the volume $V_2$ is about 60.32 mm$^3$; when the length $L_2$ is about 35 millimeters, the diameter $D_2$ is about 1.47 millimeters and the volume $V_2$ is about 59.4 mm$^3$; when the length $L_2$ is about 40 millimeters, the diameter $D_2$ is about 1.38 millimeters and the volume $V_2$ is about 59.83 mm$^3$; and when the length $L_2$ is about 50 millimeters, the diameter $D_2$ is about 1.25 millimeters and the volume $V_2$ is about 61.4 mm$^3$. Optionally, other lengths and diameters can be chosen as desired, for example, to ensure the volume $V_2$ is substantially similar to the volume $V_1$.

Figure 8:
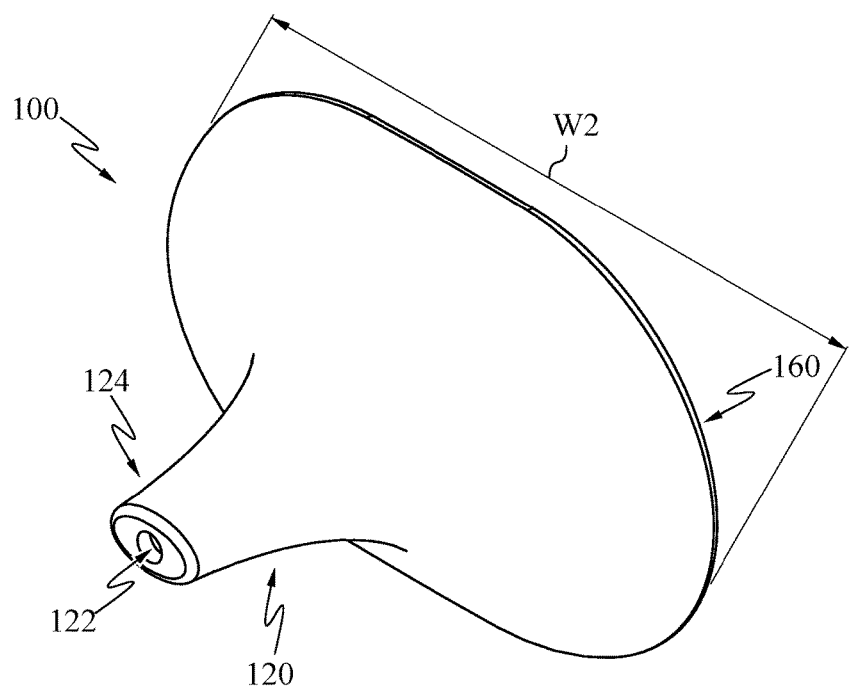
FIG. 8 shows a front perspective view of an oral administration coupler according to another example embodiment of the present invention.
Figure 9:
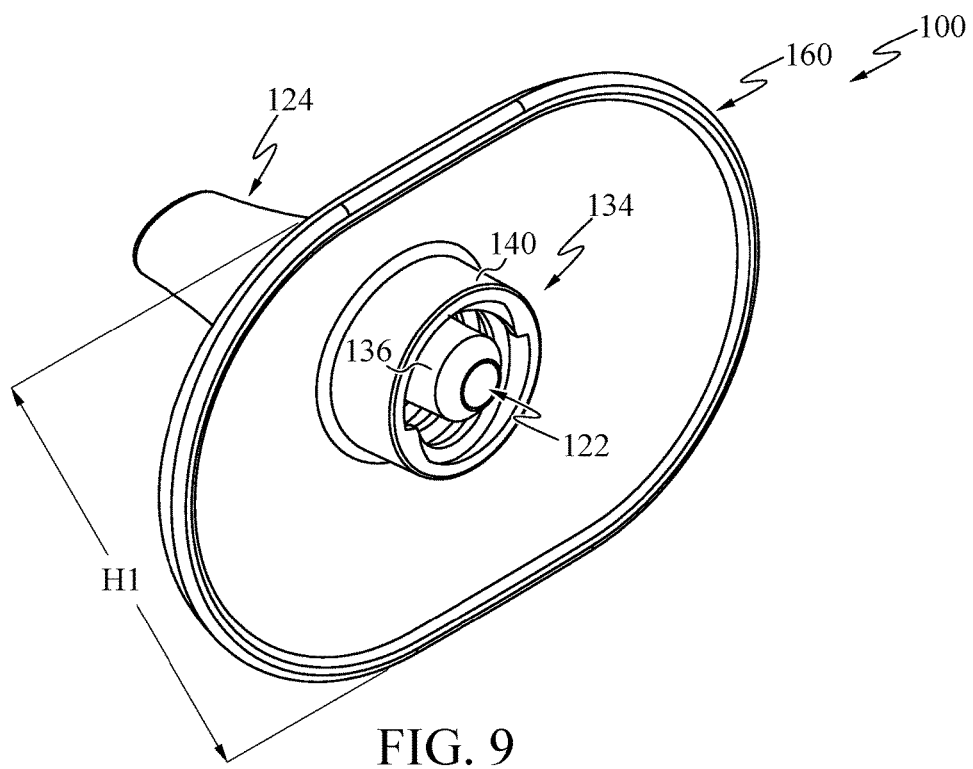
FIG. 9 shows a rear perspective view of the oral administration coupler of FIG. 8.

FIGS. 8-9 show an oral administration coupler 100 according to another example embodiment of the present invention. As depicted, the coupler 100 comprises a central fluid transfer member 120 having an oral administration applicator 124 and an ENFit compatible coupling 134, and whereby a lumen 122 is generally defined therein and extends between the ends thereof. A flange 160 generally extends outwardly from the central fluid transfer member and generally between the oral administration applicator 124 and the coupling 134. In example embodiments, the outer periphery 162 of the flange 160 is generally non-circular, for example, having two generally opposing radiused ends defining a width W2 and a height $H_1$. In example forms, the width W2 is at least partially larger than the height $H_1$. In example forms, the oral administration applicator 124 is generally similar to the applicator 24 as described above.

Figure 10:
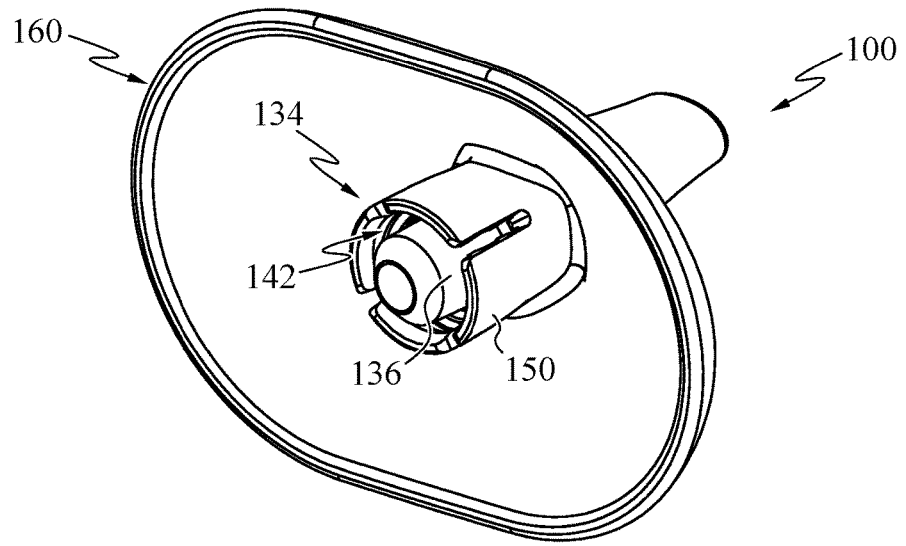
FIG. 10 shows a rear perspective view of an oral administration coupler according to another example embodiment of the present invention.
Figure 11:
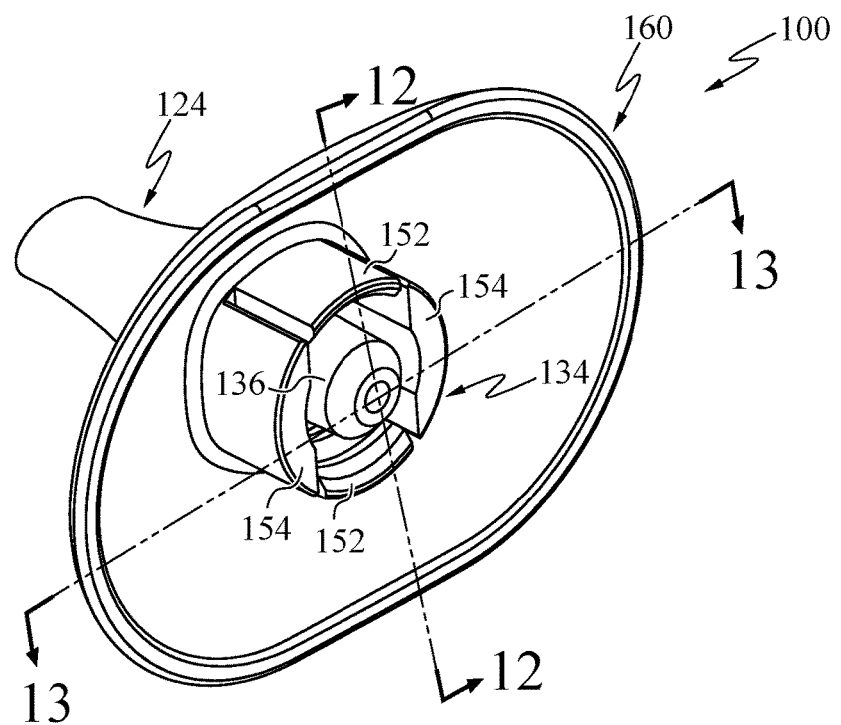
FIG. 11 shows a rear perspective view of an oral administration coupler according to another example embodiment of the present invention.

According to example form, the collar 140 of ENFit compatible coupling 134 can be configured to have one or more resilient and partially flexible clips or fingers 150, for example about four fingers 150 generally spaced radially around the port 136, for providing a push-on or snap-fit coupling engagement with the female connector FC of the syringe S (see FIG. 10). Thus, optionally, instead of screwing or rotating one of the oral administration coupler 100 or female connector FC relative to the other to provide engagement therebetween, the female connector FC can optionally be generally axially advanced relative to the coupling 134 so that the coupler 100 becomes removably engaged with the syringe S. In example forms, the flexible fingers 150 generally flex outwardly such that the female connector FC can become engaged with the connector 134, for example, thereby causing the ribs R to become engaged with the internal threaded portion 142. In example forms, the female connector FC and the ribs R thereof being generally axially advanced relative to the fingers 150 causes the ribs R to become engaged with the threaded portion 142 of the fingers 150, and wherein further axial advancement of the female connector FC enables the ribs R to cause outward flexure of the fingers 150, and then back to a neutral state, for example, wherein the ribs are generally removably engaged with the threaded portion 142. In example forms, to remove the coupler 100 from the female connector FC of the syringe S, one of the coupler 100 or the female connector FC is generally rotated relative to the other of the coupler 100 or female connector FC.

Figure 12:
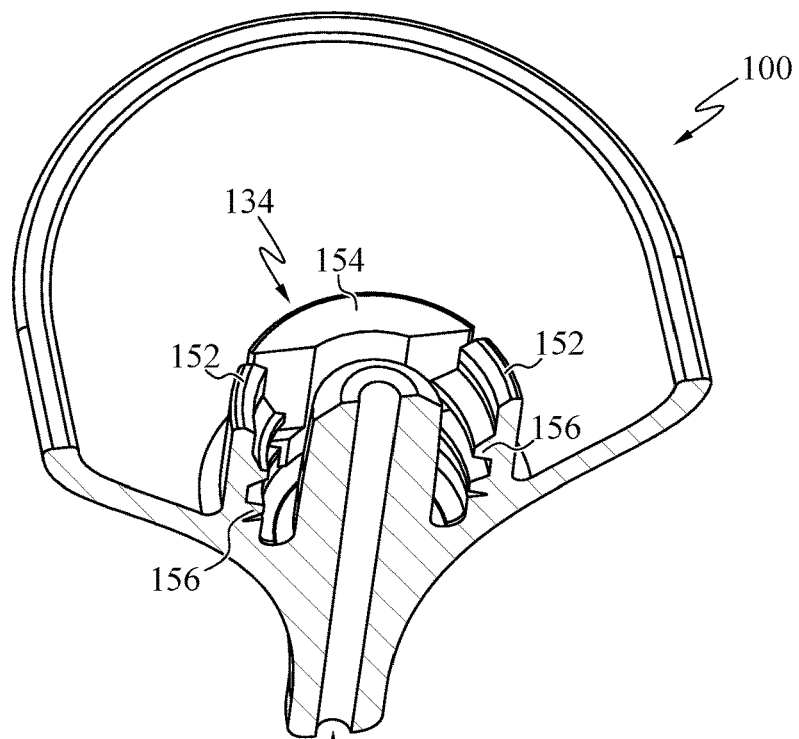
FIG. 12 shows a cross-sectional view of the oral administration coupler of FIG. 11 taken along line 12-12.
Figure 13:
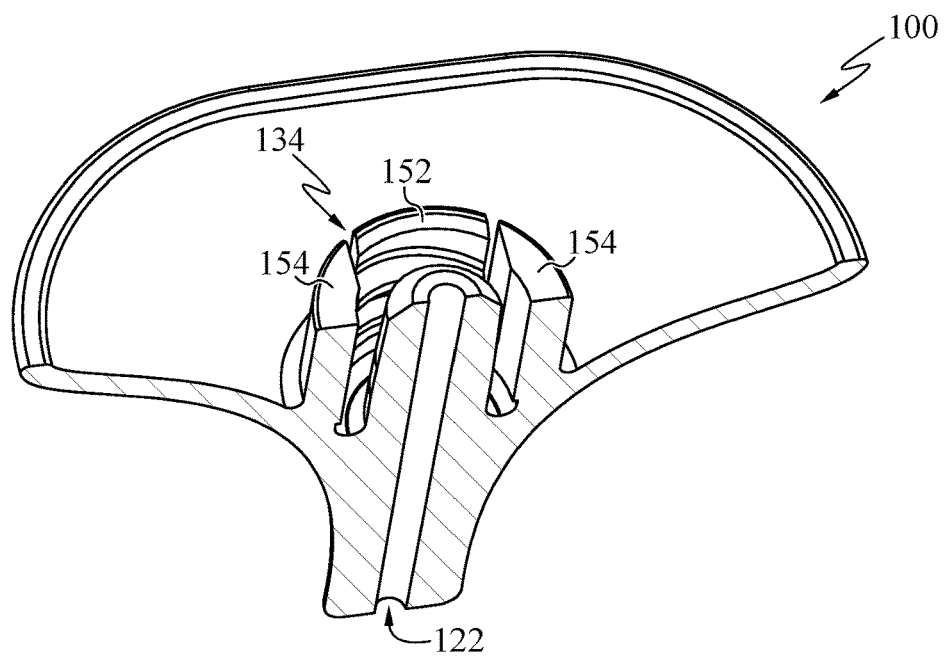
FIG. 13 shows a cross-sectional view of the oral administration coupler of FIG. 11 taken along line 13-13.

FIGS. 11-15 show the oral administration coupler 100 having yet another modified ENFit compatible coupling. As depicted, the coupling 134 comprises a locking hub connection whereby the female connector FC is substantially permanently connected once coupled therewith. For example, the coupling preferably comprises a pair of clips 152 extending outwardly on opposite sides of each other, and the sides generally adjacent the clips comprise substantially rigid supports or guide tabs 154. As shown in FIG. 12, the clips generally comprise at least one or more ribs or threads 156 on an internal portion thereof, which preferably provide for interengagement with the ribs R of the female coupling FC. However, as shown in FIG. 13, the guide tabs 154 do not comprise any threads and are substantially thicker than the clips. Thus, during engagement of the female coupling FC with the coupler 100, the ribs R are generally oriented to interengage with the threads of the clips. Preferably, the clips are at least partially flexible such that the ribs R of the female coupling FC pass by the threads of the clips when the clips are forced to flex outwardly. Once the coupling is coupled to the female coupling FC, the coupling is prevented from rotating due to the guide tabs interfering with the ribs R of the female coupling FC. Furthermore, the clips are at least partially rigid such that the female connector is generally prevented from being pulled apart from the female coupling FC.

Figure 14:
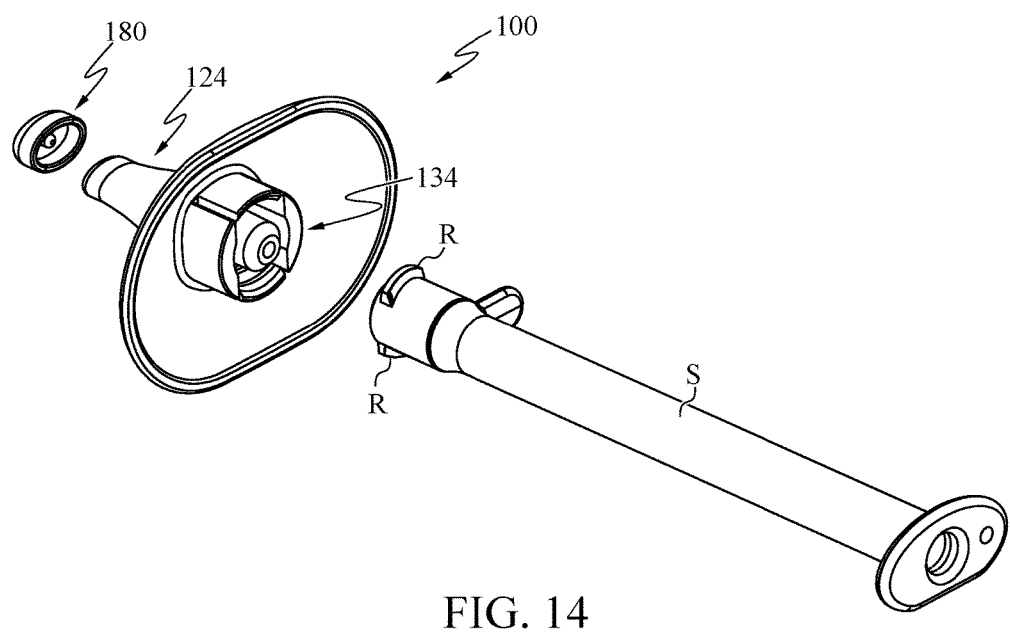
FIG. 14 shows a rear perspective assembly view of the oral administration coupler of FIG. 11 positioned between a syringe and a cap, the syringe being permanently engageable with the oral administration coupler and the cap being removably engageable with the oral administration coupler.
Figure 15:
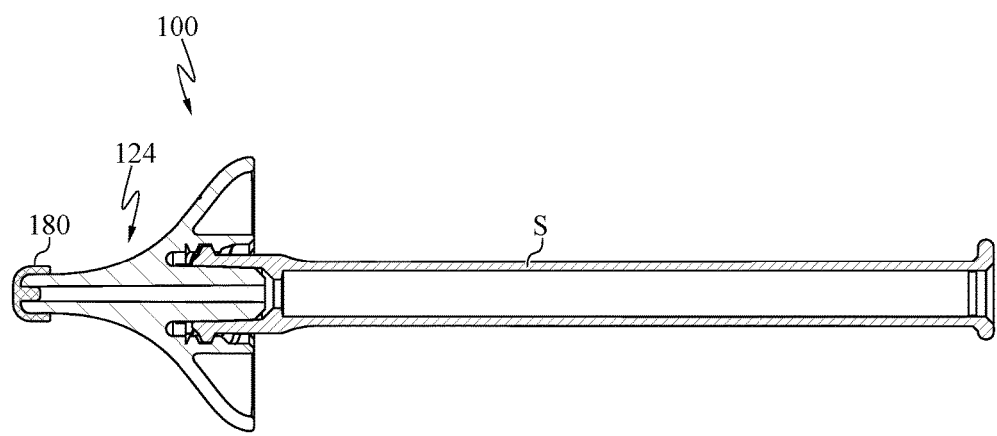
FIG. 15 shows a cross-sectional view of the oral administration coupler assembled with the syringe and cap as shown in FIG. 14.
Figure 16:
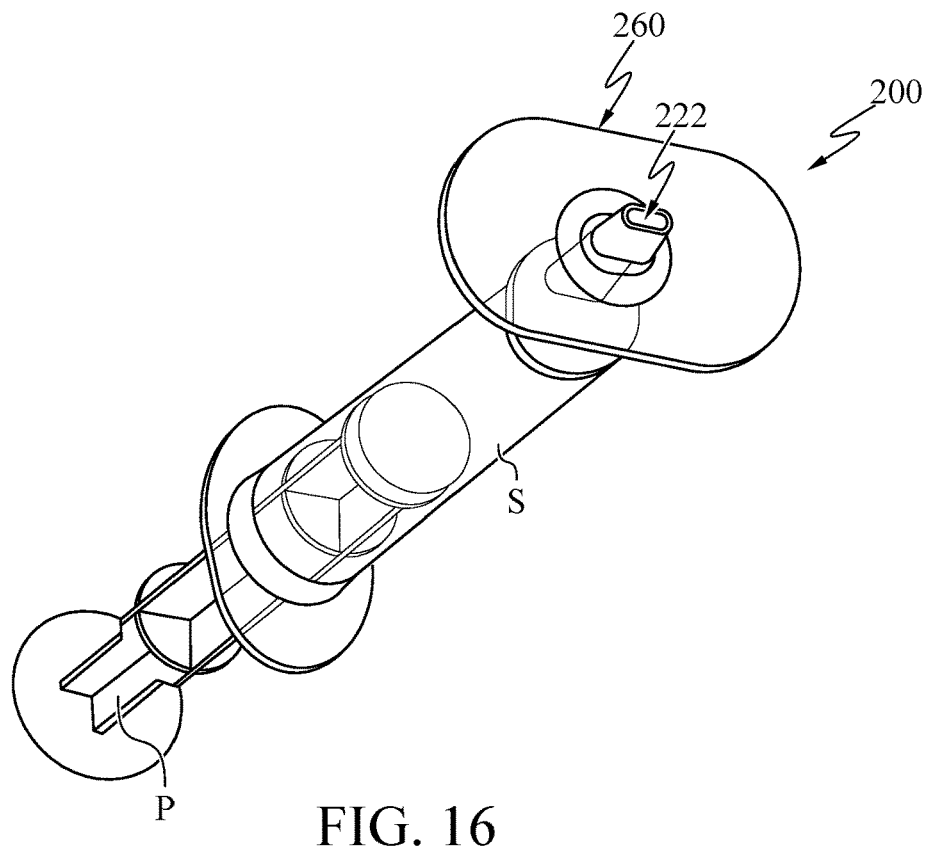
FIG. 16 shows an oral administration coupler assembled with a syringe according to another example embodiment of the present invention.
Figure 17:
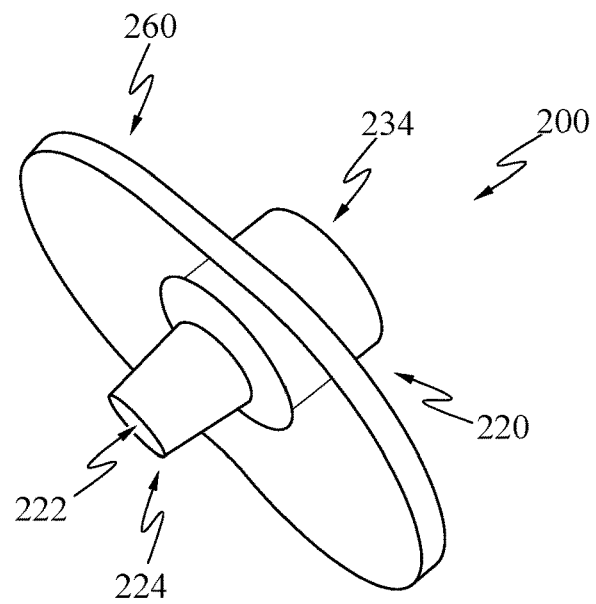
FIG. 17 shows a top perspective view of the oral administration coupler shown in FIG. 16.
Figure 18:
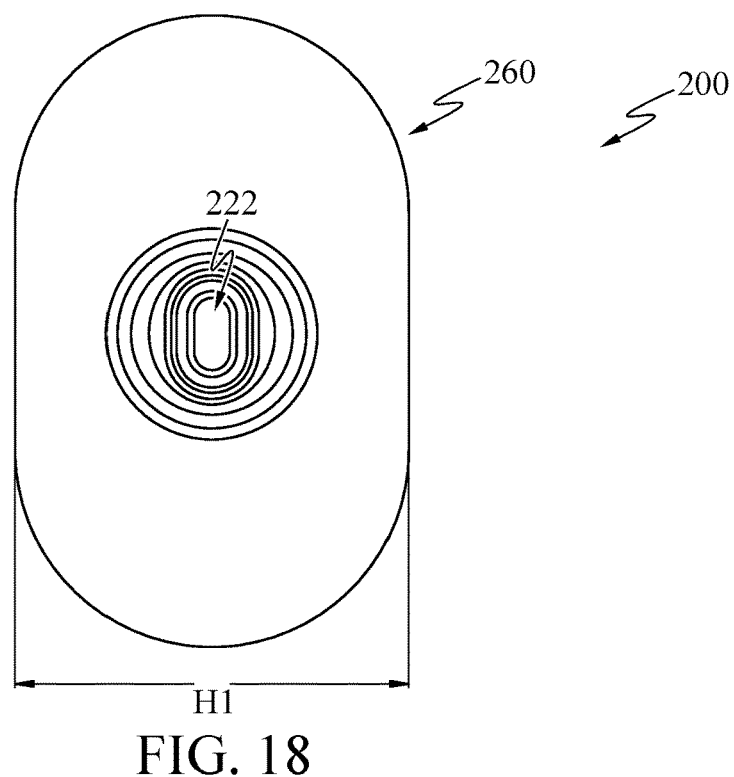
FIG. 18 shows a top plan view of the oral administration coupler of FIG. 16.

Optionally, as depicted in FIGS. 14-15, the distal end of the coupling may be provided with a cap or closure 180. In example forms, the closure 180 is generally shaped similarly to the distal end of the coupling and comprises a nipple therein for extending within the lumen 122 of the coupling. Preferably, the closure 180 may be shaped and sized as desired. Typically, the closure 180 will generally be shaped and sized to provide a generally tight yet removable fit with the distal end of the coupling, for example, which may be in the form a friction fit connection, a twist-on and/or snap-on, or other connections as desired. According to some example forms, the closure 180 may be permanently coupled with the distal end of the coupling once coupled thereto. In some example forms, the closure 180 is tethered with the coupling but without interfering with the administration of fluids from the distal end thereof. As depicted, the closure 180 is a separate piece. Preferably, the closure prevents fluids that may be within the lumen of the coupling from exiting therefrom.

In further example embodiments, the ENFit compatible coupling 134 that is configured for the push-on or snap-fit coupling engagement (e.g., having the fingers 150) or the locking hub connection (e.g., having the clips 152 and the tabs 154) can be used with a variety of other enteral delivery couplers or other enteral connectors or couplings as desired. For example, according to some example forms, the coupling 134 configured for push-on coupling engagement or the locking hub connection (as shown in FIGS. 10-15) can be configured for use with enteral couplings, connectors or other devices or members configured for engagement with an ENFit female connector FC. Thus, alternative aspects of the invention include the coupling itself, apart from the oral administration coupler, according to any of the disclosed example embodiments, which coupling is adaptable for use in connection with various other forms of fluid delivery devices, in addition to an oral administration coupler as depicted.

Figure 19:
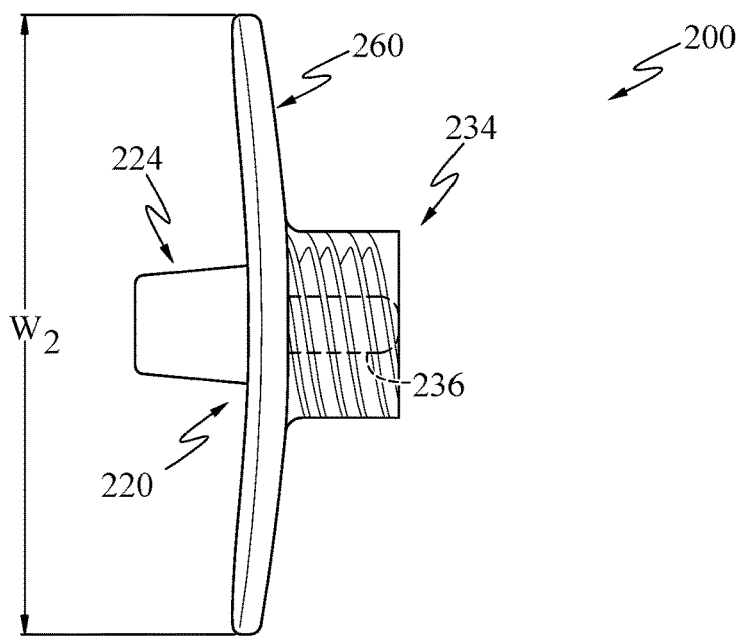
FIG. 19 shows a side plan view of the oral administration coupler of FIG. 16.

FIGS. 16-19 show an oral administration coupler according to another example embodiment of the present invention. As depicted, the oral administration coupler 200 generally comprises a central fluid transfer member 220 having an oral administration applicator 224 and an ENFit compatible coupling 234, and whereby a lumen 222 is generally defined therein and extends between the ends thereof. A flange 260 generally extends outwardly from the central fluid transfer member and generally between the oral administration applicator 224 and the coupling 234. In example embodiments, the outer periphery 262 of the flange 260 is generally non-circular, for example, having two generally opposite radiused ends defining a width $W_2$ and a height $H_1$. In example forms, the width $W_2$ is at least slightly larger than the height $H_1$. According to one form as depicted in FIG. 19, the flange 260 is generally at least partially curved towards the end of the central fluid transfer member 220 having the oral administration applicator 224. Optionally, the flange 260 can be shaped as desired.

Figure 20:
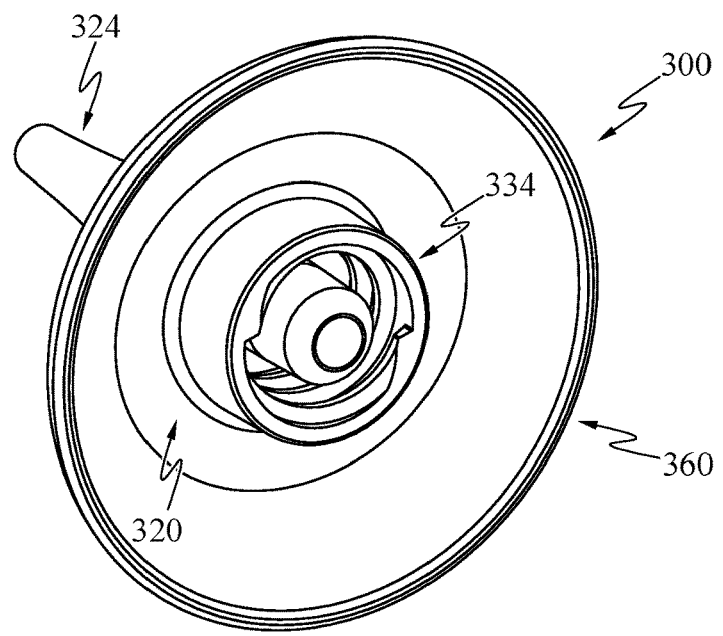
FIG. 20 shows a rear perspective view of an oral administration coupler according to another example embodiment of the present invention.
Figure 21:
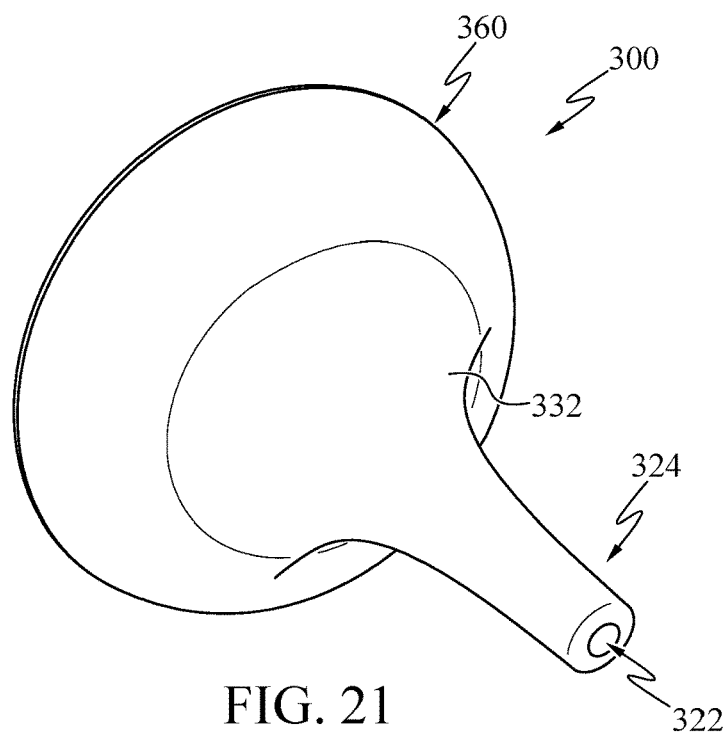
FIG. 21 shows a front perspective view of the oral administration coupler of FIG. 20.
Figure 22:
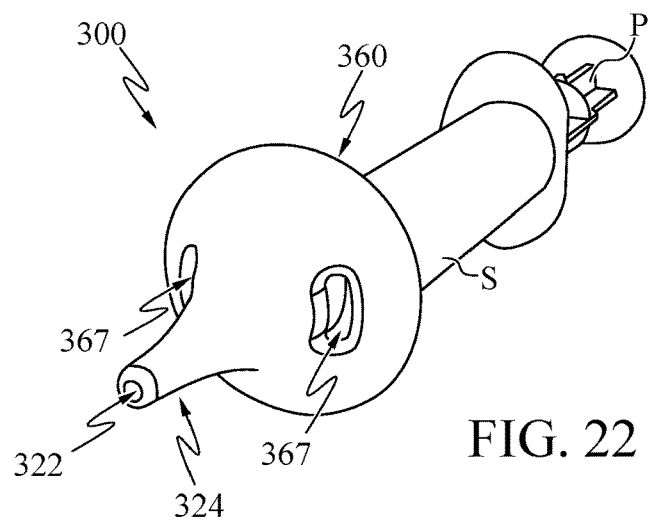
FIG. 22 shows a front perspective view of an oral administration coupler according to another example embodiment of the present invention, and showing the coupler removably mounted to a syringe and having one or more openings provided in a flange thereof.
Figure 23:
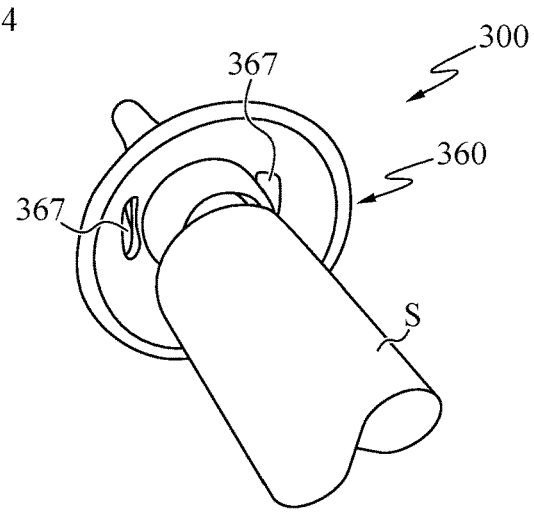
FIG. 23 shows a rear perspective view of the oral administration coupler and syringe of FIG. 22.
Figure 24:
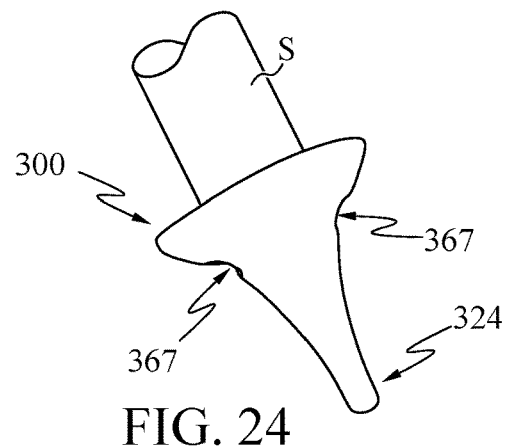
FIG. 24 shows a top perspective view of the oral administration coupler and syringe of FIG. 22.

FIGS. 20-21 show an oral administration coupler 300 according to another example embodiment of the present invention. As depicted, the oral administration coupler 300 generally comprises a central fluid transfer member 320 having an oral administration applicator 324 and an ENFit compatible coupling 334. A lumen 322 is formed within the central fluid transfer member and extends entirely through the applicator 324 and the coupling 334. A flange 360 generally extends outwardly from the central fluid transfer member and generally between the oral administration applicator 224 and the coupling 234. In example embodiments, the outer periphery 262 of the flange 260 is generally circular in shape. Similarly, the oral administration applicator 324 is generally cylindrical in shape and comprises a generally circular cross-section. In example forms, a radiused transition 332 is provided for defining a smooth transition between the oral administration applicator 324 and the outer surface of the flange 260. Optionally, as shown in FIGS. 22-24, the oral administration coupler 300 can comprise one or more vents 367 to mitigate potential choking hazards and to act as a channel for permitting fluids to flow therethrough, for example, which may be otherwise contained within the coupler 300. In example forms, two vents 367 are generally positioned on opposite sides of the central fluid transfer member and generally extend entirely through the flange 360.

FIGS. 25-28 shows an oral administration coupler 400 according to another example embodiment of the present invention. As depicted, the oral administration coupler 400 is generally elongate and extends generally linearly from a first end to a second end. For example, as similarly described above, the coupler 400 comprises an oral administration applicator 424 for orally administering the fluids and an ENFit compatible coupling 434 for coupling with the female connector FC of the syringe S. A lumen (unshown) extends entirely through the coupler 400, for example, to allow fluids from the syringe S to be delivered to the human or animal patient. In example forms, the applicator 424 is generally elongate and has a substantially circular cross-sectional shape.

Figure 25:
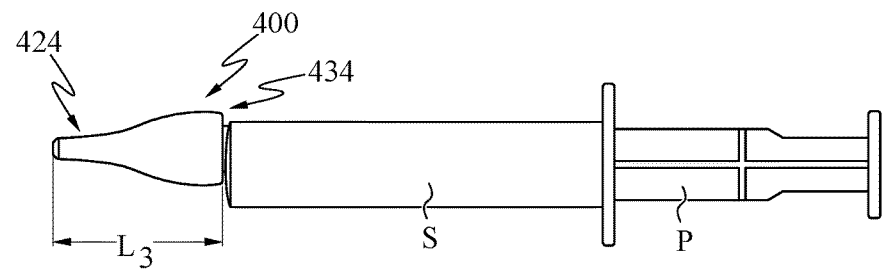
FIG. 25 shows a side view of an oral administration coupler according to another example embodiment of the present invention, and showing the coupler removably mounted to a syringe.
Figure 26:
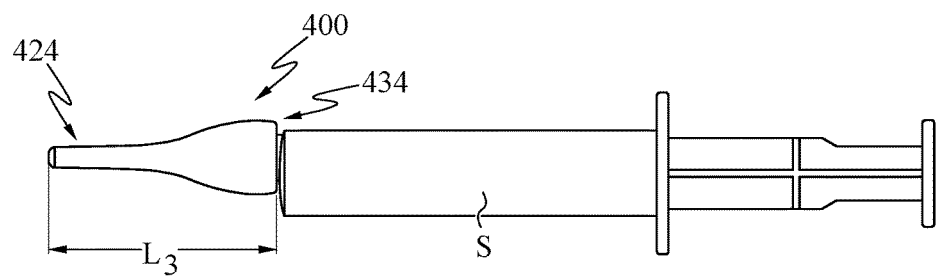
FIG. 26 shows a side view of an oral administration coupler according to another example embodiment of the present invention, and showing the coupler removably mounted to a syringe.
Figure 27:
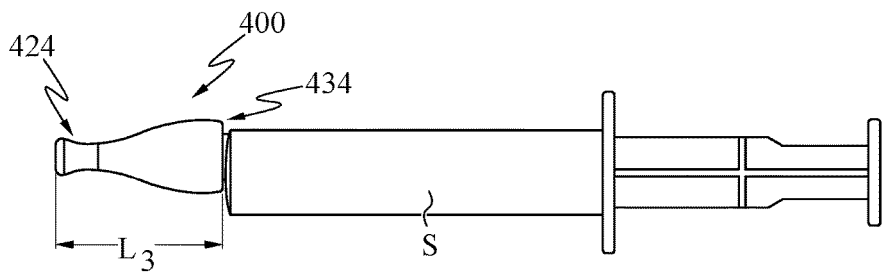
FIG. 27 shows a side view of an oral administration coupler according to another example embodiment of the present invention, and showing the coupler removably mounted to a syringe.
Figure 28:
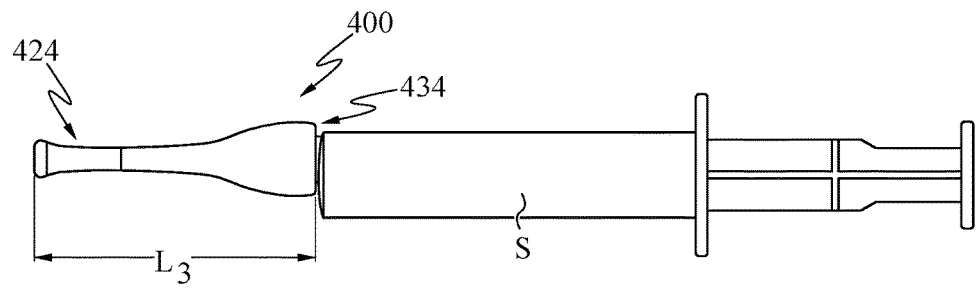
FIG. 28 shows a side view of an oral administration coupler according to another example embodiment of the present invention, and showing the coupler removably mounted to a syringe.

In example forms, the coupler 400 defines a length $L_3$, which can preferably be sized accordingly. For example, the length $L_3$ of the coupler 400 shown in FIG. 25 is about 30 millimeters, the length $L_3$ of the coupler 400 shown in FIG. 26 is about 45 millimeters, the length $L_3$ of the coupler 400 shown in FIG. 27 is about 30 millimeters, and the length $L_3$ of the coupler 400 shown in FIG. 28 is about 50 millimeters. Optionally, the length $L_3$ can be chosen as desired, for example, which is generally between about 15 millimeters to about 60 millimeters, more preferably between about 30 millimeters to about 50 millimeters. In example embodiments, the length $L_3$ is generally at least about 1.25-1.75 times larger than the width or diameter of the coupling 434. In some example forms, the length $L_3$ is generally 2-3 times larger than the diameter of the coupling 434.

As depicted in FIGS. 25-26, the applicator 424 comprises a generally elongate post-like nozzle, which generally comprises a substantially similar cross-section until transitioning to the coupling 424, for example, where the diameter of the cross-section substantially increases. However, as depicted in FIGS. 27-28, the applicator 424 generally comprises a horn-shaped tip wherein the diameter of the cross-section at the end of the applicator 424 (e.g., first end) is generally larger than the diameter of the cross-section at a middle portion or midsection of the applicator 424. Optionally, the applicator 424 can be shaped and sized as desired.

According to one example embodiment, the applicators 324, 424 as described here can preferably be compatible for engagement with legacy enteral/oral connectors. For example, in some example embodiments, the applicators 324, 424 are preferably sized for engagement with a legacy style connector to draw fluids from a container or pharmacy bottle. In another embodiment, the applicators 324, 424 (and/or lumens extending therethrough) can be configured for coupling engagement with one or more components of a legacy style system or other legacy components, for example, such as a legacy style feeding tube.

Figure 29:
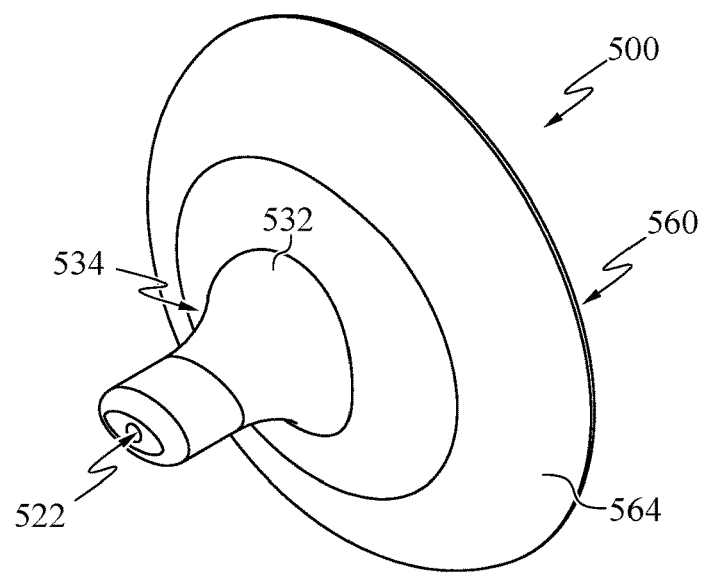
FIG. 29 shows a front perspective view of an oral administration coupler according to another example embodiment of the present invention.
Figure 30:
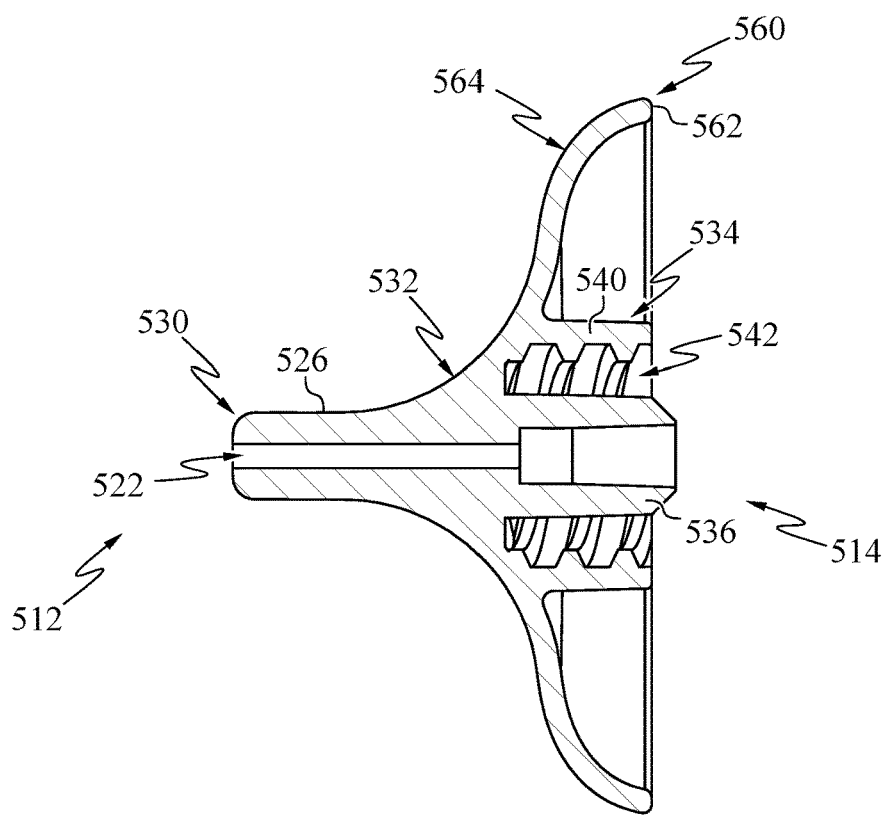
FIG. 30 shows a cross-sectional view of the oral administration coupler of FIG. 29.
Figure 31:
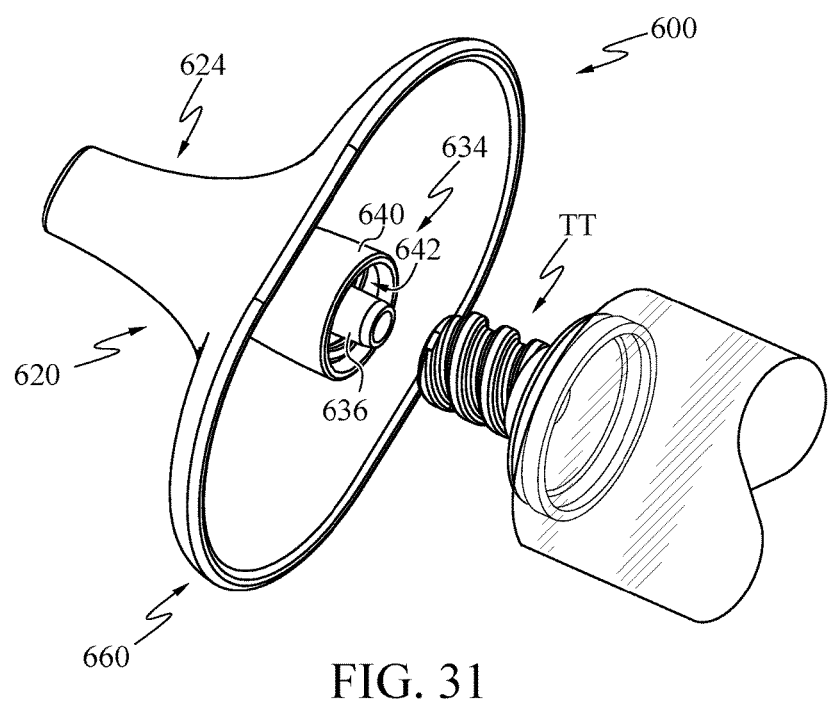
FIG. 31 shows a rear perspective assembly view of an oral administration coupler and a syringe according to another example embodiment of the present invention.
Figure 32:
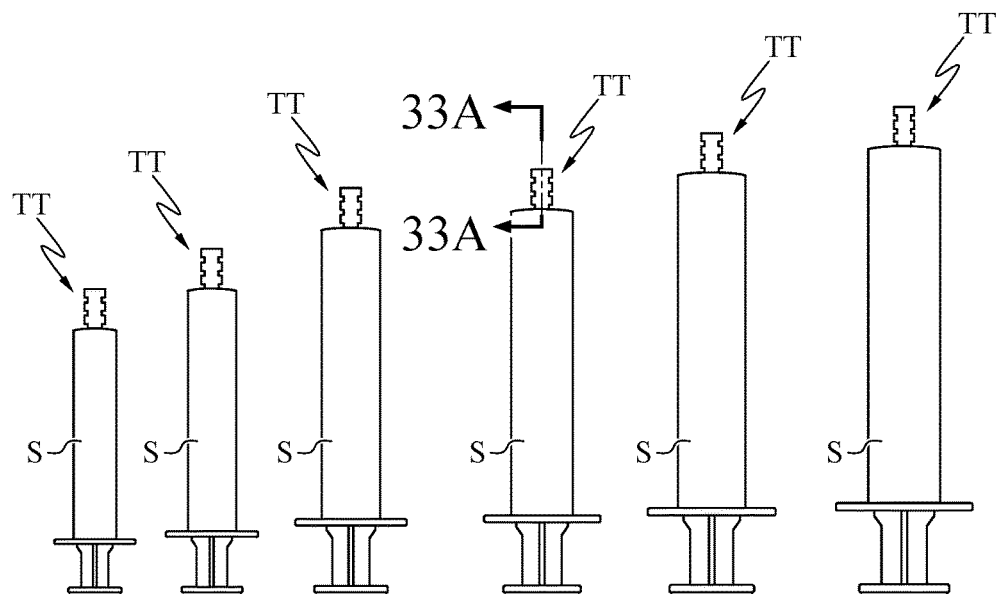
FIG. 32 shows a plurality of syringes for use with the oral administration coupler shown in FIG. 31.

FIGS. 29-30 show an oral administration coupler 500 according to another example embodiment of the present invention. As depicted, the coupler 500 is generally similar to the coupler 10 as described above. In example forms, the coupler 500 generally comprises a central fluid transfer member 520 having an oral administration applicator 524 and an ENFit compatible coupling 534. Preferably, a lumen 522 is generally defined within the applicator 534 and the coupling 534, and extends entirely between the ends thereof. A flange 560 generally extends outwardly from the central fluid transfer member and generally between the oral administration applicator 524 and the coupling 534. In example embodiments, the outer periphery 562 of the flange 560 is generally circular, for example, which is substantially similar to the flange 60 of the coupler 10 (see FIGS. 1-7). Furthermore, as similarly described above, the applicator 524 is generally in the form of an irregular or asymmetric nipple, which is generally duckbilled in shape and having a generally non-circular or oval cross-section. Optionally, the applicator can be shaped as desired. Similarly to the flange 60, the flange 560 comprises a radiused transition 532 formed with the oral delivery applicator 524, and an outer portion of the flange 560 generally comprises a radiused surface profile 564 that extends to the outer periphery 562. Preferably, the flange 560 is generally substantially symmetrical and comprises a substantially smooth and radiused outer surface.

According to additional example embodiments, the oral administration coupler can be formed such that a threaded syringe tip is capable of interengagement therewith. According to one example embodiment, the threaded syringe tip and couplers for compatible engagement with the threaded syringe tip are generally not formatted according to the ISO 80369-3 standard. However, according to other example embodiments, the threaded syringe tip and compatible couplers are generally at least compatible with the ISO 80369-3 standard. For example, FIGS. 31-34 show an oral administration coupler 600 that is generally similar to the couplers as described above, for example, which generally comprises a central fluid transfer member 620 comprising an oral administration applicator 624, a coupling 634, and a flange 660 generally outwardly extending from the central fluid transfer member 620. Preferably, the coupling 634 comprises a central port 636 defining a lumen 622 extending through the central fluid transfer member 620, and a collar 640 is generally positioned to substantially surround the central port 636. Preferably, the collar 640 comprises a threaded internal portion 642 for providing removable engagement with helical threads T of a threaded tip TT of a syringe (see also FIGS. 31-34). According to some example forms, the threads T of the threaded tip TT comprise a thread pitch TP of about 2.45 millimeters and an outer diameter $D_3$ of about 6.657 millimeters (see FIG. 33A), and the threaded internal portion of the coupling preferably has dimensions to provide a complementary fit therewith. Optionally, other dimensions may be provided as desired. As depicted in FIG. 34, the volume path $V_1$ defined between the coupling and the threaded tip TT is generally between about 0.005-0.10 ml, more preferably about 0.02 ml.

Figure 35:
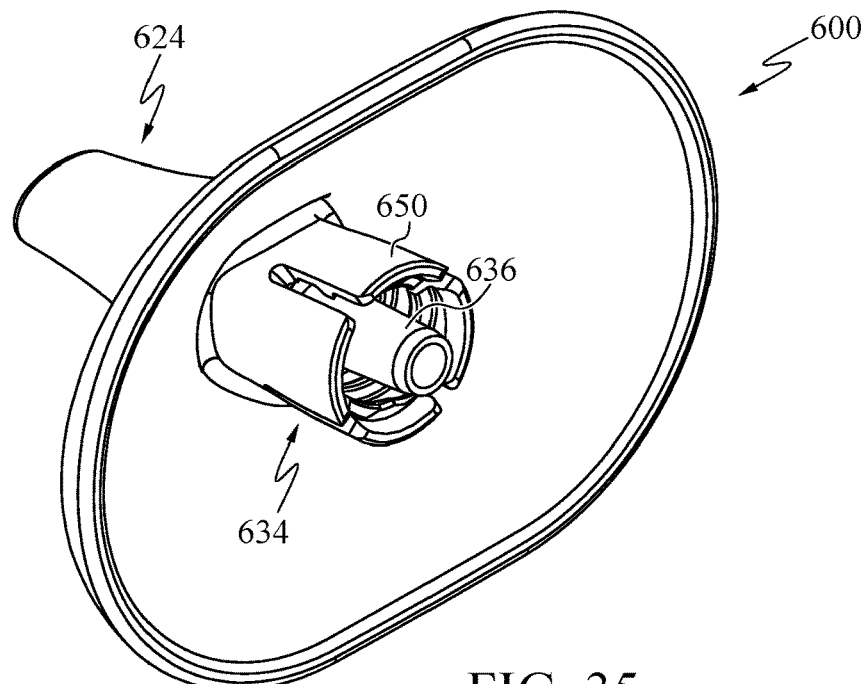
FIG. 35 is a rear perspective view of an oral administration coupler according to another example embodiment of the present invention.

FIG. 35 shows a coupler 600 according to another example embodiment of the present invention. As depicted, the coupler 600 preferably comprises about four clips 650 and wherein the internal portions thereof comprises a threaded portion for interengagement with the threads T of the threaded tip TT. According to some example forms, the coupler 600 is configured to be coupled to the threaded tip TT by generally axially moving one of the coupling or threaded tip TT towards the other. During movement therebetween, the clips 650 are capable of generally flexing outwardly to allow for the threaded internal portion of the coupling to pass over the threads T of the threaded tip. To disengage the coupling from the threaded tip TT, the coupling 600 is generally unscrewed from the threaded tip.

Figure 36:
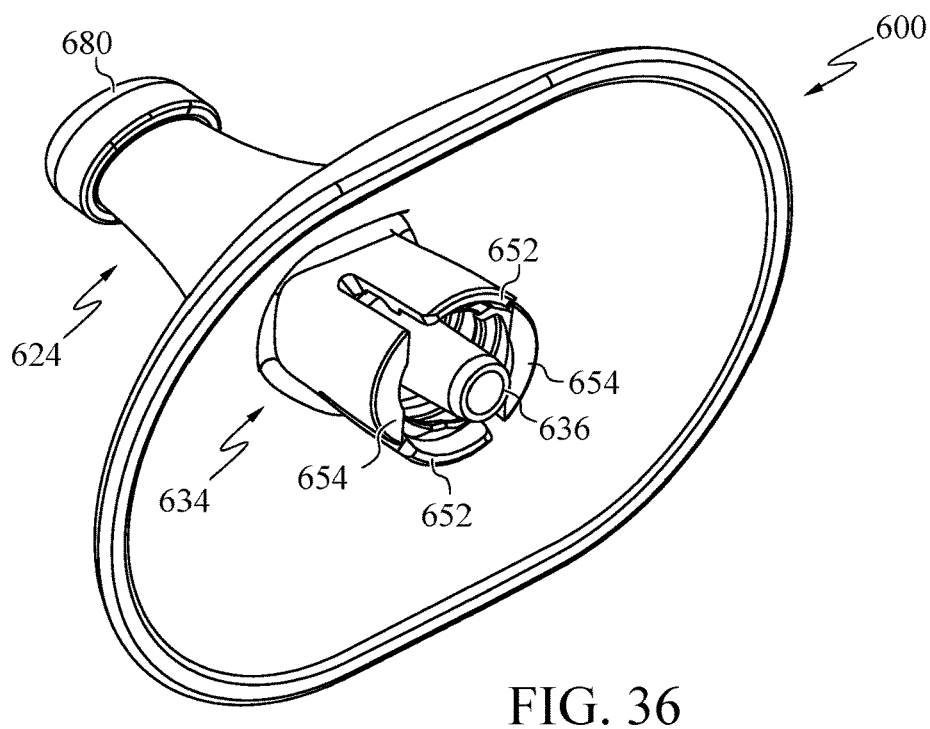
FIG. 36 is a rear perspective view of an oral administration coupler according to another example embodiment of the present invention, and showing a cap removably attached to a portion thereof.

FIG. 36 shows a coupler 600 according to another example embodiment of the present invention. As shown, the coupler 600 comprises locking clips 652 formed near the threaded internal portion of the coupling such that the coupling is incapable of being removed from the threaded tip TT of the syringe. For example, once the threaded tip TT is inserted within the coupling 634 and the threads or interengagement features therein interengage with the threads T of the threaded tip TT, the coupling is substantially permanently engaged with the threaded tip TT. As similarly described above, the clips 652 are generally at least partially flexible and the guide tabs 654 are generally rigid and comprise a greater thickness than the clips. Optionally, as depicted in FIG. 36, a cap or closure 680 may be provided with the coupling such that fluids a prevented from flowing from the end of the coupling. Furthermore, as recited above, the cap 680 may be in a variety of shapes and forms to removably or permanently couple with the distal end of the coupling. According to some example forms, the cap is generally a separate piece which may be separable from the coupler. According to other example forms, the closure 680 is tethered to the coupler 600. According to some example forms, the tether does not inhibit the administration of fluids orally.

In example forms, the oral administration coupling is generally formed from a rigid material (>700 MPA as per the ISO standard). Optionally, the coupling may be formed from a flexible, elastomeric material. Further optional, the oral administration coupling can be formed from two or more materials, for example, at least one rigid material and at least one flexible, elastomeric material. In some example forms, the coupling can be formed from materials of one or more colors and/or may be at least partially translucent or clear, for example, such that the fluid or nutrients flowing therethrough are visible to the human eye. Optionally, the coupling can be in the formed from light protecting materials, for example, reflecting or blocking UV or other wavelengths to reduce or eliminate damage to contents by light. As depicted in the figures, the coupling is generally linear (e.g., straight). Optionally, the coupling can be curved, angled, or otherwise shaped as desired. Optionally, an end portion of the coupling (e.g., applicator) may be shaped to be generally round, oval, crescent, rectangular, flat, radiused, other otherwise shaped as desired. Optionally, the end portion of the coupling may be shaped similarly to an enteral only syringe tip.

According to additional example embodiments of the present invention, the coupling may be provided as an accessory to a bottle or variable-volume container, for example, as disclosed in U.S. patent application Ser. No. 13/191,721, the entirety of which is incorporated herein by reference. Optionally, according to additional example embodiments of the present invention, the oral administration coupling as shown throughout the figures can be provided as an accessory to a variable-volume syringe comprising a modified ENFit coupling comprising a dosing control coupling, for example, as disclosed in U.S. Non-Provisional patent application Ser. No. 15/210,282, the entirety of which is incorporated herein by reference. According to example forms, the dosing control coupling preferably provides for a more accurate output of fluids from the syringe relative to the volume of fluids filled within the syringe, for example, so that the administered dose delivered to the patient is substantially accurate.

Figure 37:
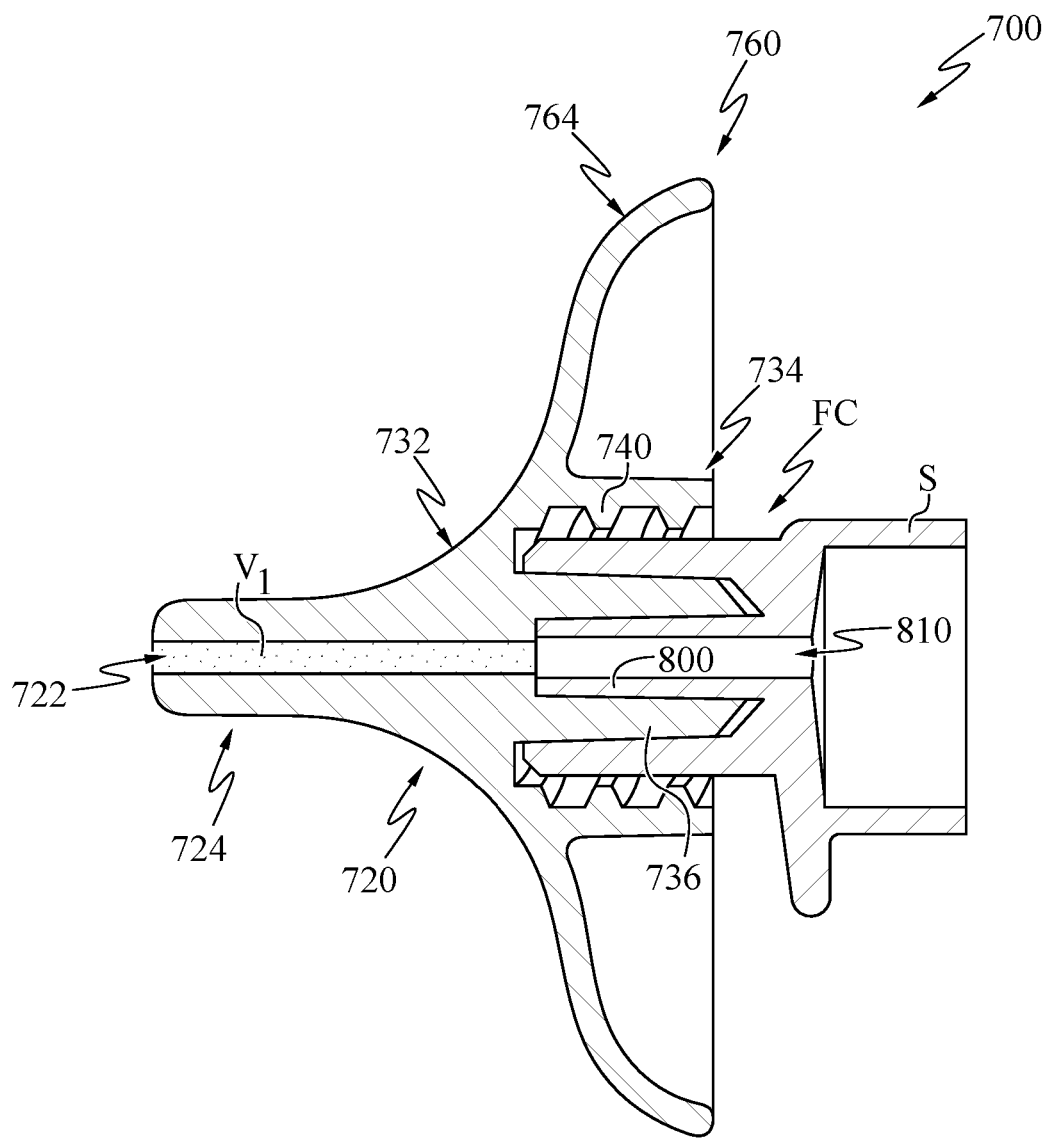
FIG. 37 is a cross-sectional view of an oral administration coupler removably coupled to a syringe having a lumen extension tip within the female connector thereof according to another example embodiment of the present invention.

For example, as depicted in FIG. 37, the syringe S comprises a female connector FC, which further comprises a lumen extension tip 800 that is generally axially aligned (and coaxial and concentric) with the female connector FC and comprising a lumen 810 therein for communicating with the internal cavity or chamber of the variable volume container or syringe S. As such, the female connector FC is generally removably coupled to an ENFit compatible coupling 734 of an oral administration coupler 700. As depicted, the oral administration coupler 700 is generally substantially similar to the oral administration coupler 10 as described above, for example, and comprising a fluid transfer member 720 extending between a first end and a second end, and wherein the first end comprises an oral administration applicator 734 and the second end comprises the ENFit compatible coupling 734 for providing engagement with the female connector FC of the syringe (and the lumen extension tip 800) axially extending therein. Furthermore, a flange 760 generally extends outwardly in a circumferential manner to define a generally cylindrical shape.

In example forms, the lumen extension tip 800 preferably generally extends entirely within the lumen of the port 736, and comprises the lumen 810 therein for generally communicating with the lumen 722 that is generally axially centered within the generally linear extension of the applicator 734. Preferably, with the lumen extension tip 800 provided within the female connector FC, the volume equivalence (see FIG. 7) generally becomes less important, for example, since the volume of the lumen 722 is substantially decreased by introduction of the lumen extension tip 800 within the lumen of the port 736. Thus, according to example forms, the size of the lumen 722 that is not occupied by the lumen extension tip 800 (e.g., $V_1$) can be varied, for example, between about 0.0005 mL to about 0.02 mL, more preferably between about 0.0015 mL to about 0.015 mL, for example about no more than 0.01 mL according to one example embodiment.

As similarly described with respect to FIG. 7 and the coupler 10, preferably one or more dimensions of the coupler 700 can be configured as desired, for example, the diameter $D_1$, the length $L_1$, the width $W_1$, the thickness $T_1$, the length $L_2$ and the diameter $D_2$.

According to another example embodiment, the present invention relates to a method of designing a fluid delivery device comprising calculating a volume of at least a portion of a fluid delivery path of a first fluid delivery device; and designing a fluid delivery path of a second fluid delivery device to substantially match the fluid delivery path volume of the first fluid delivery device. In example forms, the first fluid delivery device comprises a pharmacy coupler for transferring fluids from a container to a syringe. Generally, the second fluid delivery device comprises an oral administration coupler for delivering fluids from a syringe to a cheek area of a child or infant.

According to additional example embodiments of the present invention, oral delivery of fluids and/or medication can be configured for back-of-mouth delivery, for example, such that the output of fluids from the coupler, syringe or other accessory is such that the tongue of the patient receiving the fluids is bypassed. In some example forms, for example, when medications are to be delivered orally, it may be advantageous to deliver the medications beyond the tongue of the patient, thereby substantially eliminating the patient's tongue (and taste buds thereof) from coming into contact with the medicine, which can be substantially distasteful. Thus, when medications or other fluids are delivered beyond the tongue of the patient, the patient is less likely to taste the medications, and therefore reduces the likelihood of the patient gagging or spitting out the medication or fluids to be delivered. Moreover, delivering the medications or fluids to the back of the mouth of the patient further ensures that the proper dose is delivered and ingested by the patient.

Figure 38:
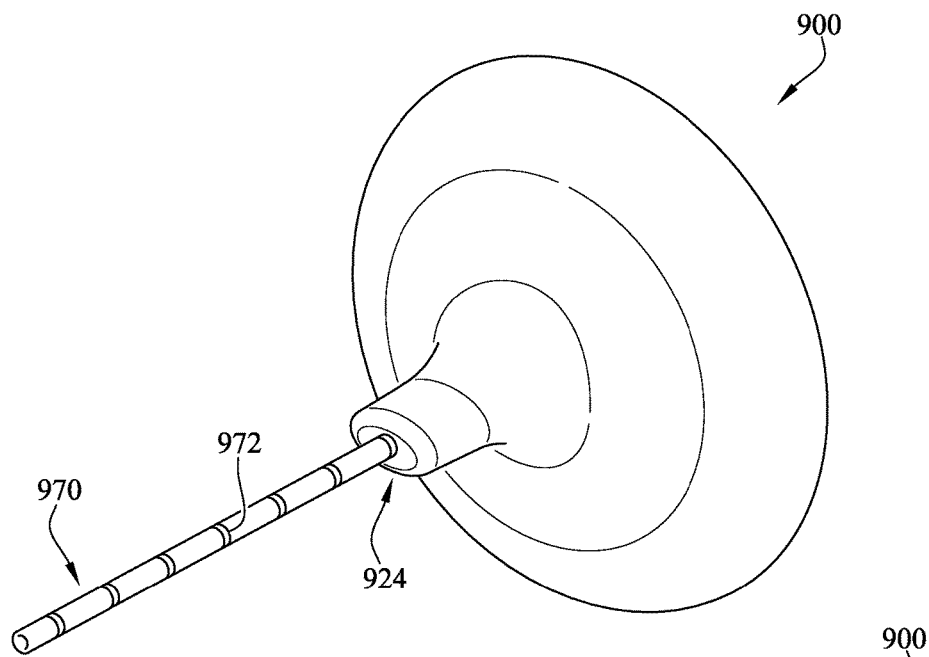
FIG. 38 shows an oral administration coupler according to another example embodiment of the present invention.
Figure 39:
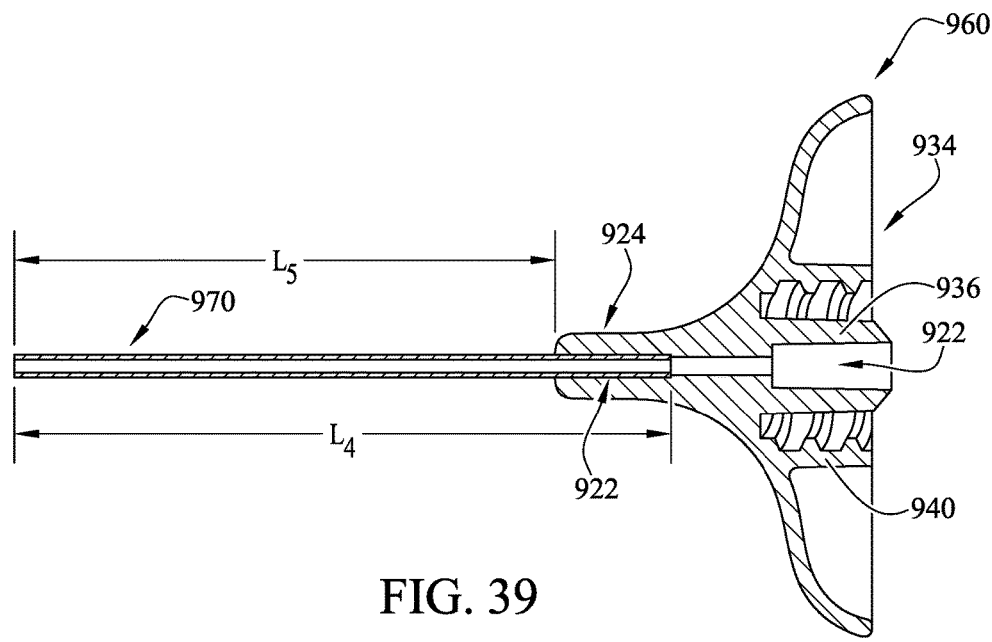
FIG. 39 shows a cross-sectional view of the oral administration coupler of FIG. 38.

FIGS. 38-39 show an oral administration coupler 900 according to another example embodiment of the present invention. In example embodiments, the coupler 900 is substantially similar to the couplers 10, 700 as described above. As depicted in FIG. 38, a generally elongate straw or flexible conduit or tube 970 couples with the coupler 900, for example, wherein at least a portion of the tube 970 is engaged within the lumen 922 of the oral delivery applicator. Thus, the tube 970 extends from the oral delivery applicator 924 in a direction generally opposite the second end. In example embodiments, the tube 970 comprises a length of between about 30-120 millimeters and can be formed from any available French gauge (Fr) tube as desired. According to one example embodiment, the tube 970 is substantially flexible, comprises a length $L_4$ of about 40 millimeters and is sized to be a 4 Fr tube. Optionally, other size tubes can be chosen as desired. In some example embodiments, the tube 970 comprises one or more graduations or markings 972 thereon, for example, to assist in the measurement of the dosage quantity. Optionally, the tube 970 can be substantially clear and free from any marking or graduations. According to one example embodiment, the tube 970 is generally frictionally engaged with the lumen 922 of the coupler 900. Optionally, the tube 970 can be integrally formed with the lumen or otherwise be permanently secured therewith. As depicted in FIG. 39, a portion of the lumen 922 near the end of the oral delivery applicator can be generally bored or comprise a greater diameter to allow for proper fitting engagement with the tube 970. Optionally, as depicted with respect to the couplers 10, 700, the lumen can be substantially uniform throughout the entirety of the central fluid transfer member.

FIGS. 40-42 show an oral administration coupler 1000 according to another example embodiment of the present invention. As depicted, the oral administration coupler 1000 is generally similar to the couplers as described above, for example, comprising a central fluid transfer member 1020 extending from a first end 1012 to a second end 1014, and an outer flange 1060 generally positioned between the first and second ends of the central fluid transfer member 1020 and extending generally outwardly therefrom. In example embodiments, the central fluid transfer member 1020 comprises an elongate stem or oral delivery applicator 1024 at the first end 1012 of the fluid transfer member 1020 and an ENFit compatible coupling or connector 1034 positioned at the second end 1014 of the fluid transfer member 1020. In example forms, the oral delivery applicator 1024 generally extends in a direction that is substantially opposite to the direction of the extension of the connector 1034. The flange 1060 is generally integrally formed with the fluid transfer member 1020 between the first and second ends 1012, 1014 of the fluid transfer member 1020. Optionally, the flange 1060 can be a separate piece for permanent or removable coupling engagement with the central fluid transfer member 1020.

As described above, the connector 1034 is generally configured for removable coupling and sealing engagement with the female connector FC of the syringe S (see FIG. 42) so that fluids can be transferred through the coupling and orally administered to a human or animal patient by actuation of a plunger movably mounted within the syringe S. Preferably, a lumen 1022 is provided within the fluid transfer member 1020 and extends between the first and second ends 1012, 1014, for example, through the entirety of both the oral delivery applicator 1024 and the ENFit compatible coupling 1034, providing fluid communication from the inlet end 1014 of the coupler 1000 at the syringe S, to the outlet end 1012 of the coupler at the delivery applicator 1024. In example embodiments, the oral administration coupler 1000 defines a length $L_6$ of between about 15 millimeters to about 60 millimeters, for example about 30 millimeters according to one example embodiment. Optionally, the length $L_6$ can be less than about 15 millimeters or greater than about 60 millimeters.

In example embodiments, the oral delivery applicator 1024 is generally substantially cylindrical or generally uniformly rounded or circular and has a generally circular cross-section. As depicted in FIG. 42, the delivery applicator comprises a length $L_7$ of between about 5 millimeters to about 50 millimeters, for example about 18 millimeters to about 20 millimeters according to one example embodiment. In example embodiments, the oral delivery applicator 1024 comprises a diameter $D_4$ proximal the first end 1012 and a diameter $D_5$ generally near the applicator's 1024 engagement with the flange 1060. In example embodiments, the diameter $D_4$ is generally between about 3 millimeters to about 6.5 millimeters and the diameter $D_5$ is generally between about 3.5 millimeters to about 8 millimeters. Optionally, according to additional example embodiments, the oral delivery applicator 1024 can be sized and shaped as desired, and for example, extend a desired length. According to one example embodiment, a generally radiused transition is provided between the oral delivery applicator 1024 and the flange 1060, for example, as similarly described and shown in FIG. 7. However, according to some example embodiments, a less radiused transition, or generally no transition at all need be provided between the oral delivery applicator 1024 and the flange 1060, for example, wherein an included angle of between about 75 to about 135 degrees is defined between the extension of the oral delivery applicator 1024 and the flange 1060.

According to one example embodiment, the applicators 1024 can preferably be compatible for engagement with legacy enteral/oral connectors. For example, in some example embodiments, the applicator 1024 is preferably sized for engagement with a legacy style connector to draw fluids from a container or pharmacy bottle (e.g., with the legacy style connector fitted with the bottle). In another embodiment, the applicator 1024 (and/or lumen 1022 extending therethrough) can be configured for coupling engagement with one or more components of a legacy style system or other legacy components, for example, such as a legacy style feeding tube.

In example embodiments, the flange 1060 is generally non-circular in shape and comprises a radiused surface profile 1064, for example, such that the flange is generally transitioning or substantially extending generally outwardly and towards the second end 1014. Optionally, the flange can have a generally circular or rounded shape as desired. In example embodiments, at least one opening, vent or hole 1074 can be formed through one or more portions of the flange 1060 as desired. In example embodiments, about four openings are formed in the syringe. In additional example embodiments, a plurality of openings can be formed in the syringe as desired, for example, of a desirable size, shape and position. Optionally, the quantity, size, shape, etc. of the openings 1074 can be chosen as desired. In example embodiments, the size or volume of the lumen 1022 of the oral administration coupler 1000 that is not occupied by the female coupler FC of the syringe S (when attached thereto) is between about 0.0005 mL to about 0.1 mL. According to one example embodiment, the female coupler FC of the syringe can comprise a lumen extension tip to further improve dosing accuracies (see also FIG. 37). For example, the female coupler FC of the syringe S can comprise a lumen extension tip generally positioned coaxially and concentrically within the female coupler FC, for example such that the lumen extension tip can be fitted within the lumen 1022 of the transfer port 1036 of the ENFit compatible coupling 1034 when the female coupler FC is coupled with the ENFit compatible coupling 1034.

Figure 43:
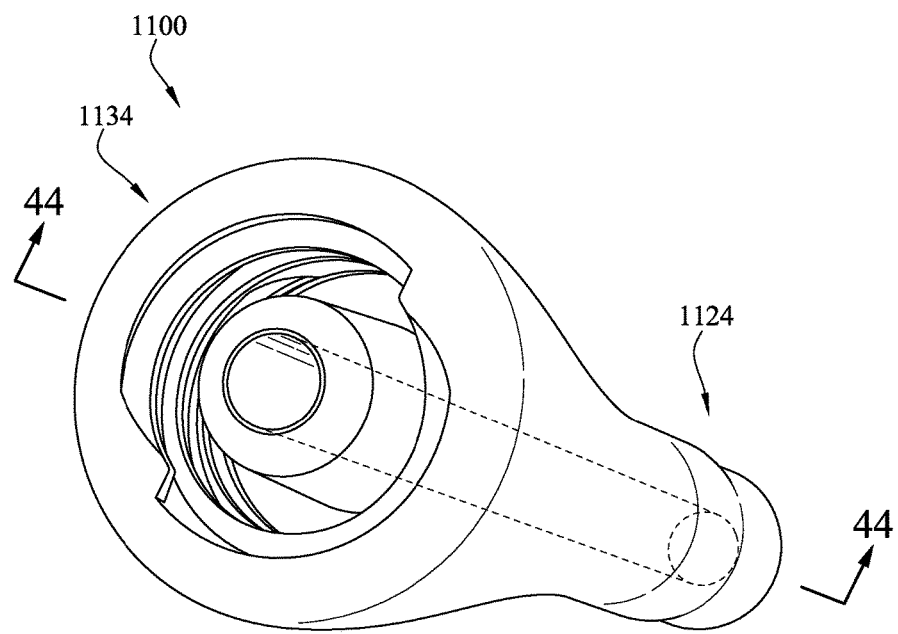
FIG. 43 shows a rear perspective view of an oral administration coupler according to another example embodiment of the present invention.
Figure 44:
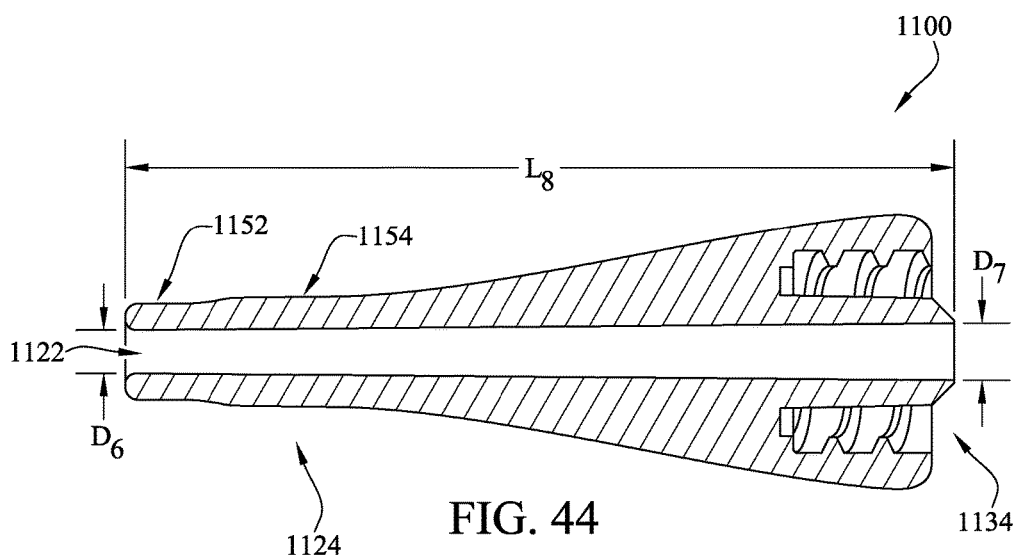
FIG. 44 shows a side view of the oral administration coupler of FIG. 43.

FIGS. 43-44 show an oral administration coupler according to another example embodiment of the present invention. As depicted, the oral administration coupler 1100 is generally similar to the oral administration coupler 400 as described above. In example embodiments, the coupler 1100 comprises an oral administration applicator 1124 for orally administering fluids and an ENFit compatible coupling 1134 for coupling with the female connector FC of the syringe S. A lumen 1122 extends entirely through the coupler 1100, for example, to allow fluids from the syringe S to be delivered to the human or animal patient. In some example embodiments, the lumen 1122 defines an internal diameter $D_6$ of about 2.18 millimeters at an end proximal the applicator 1124 and an internal diameter $D_7$ is defined proximal the coupling 1134. In example embodiments, the diameter $D_6$ is between about 1 millimeter to about 3 millimeters, for example about 2.18 millimeters, and the diameter $D_7$ is between about 1.5 millimeters to about 4.5 millimeters, for example about 2.9 millimeters. In example forms, the applicator 1124 is generally elongate and has a substantially circular cross-sectional shape. According to example embodiments, the oral administration coupler 1100 comprises a length $L_8$ that is generally between about 15 millimeters to about 60 millimeters. According to one example embodiment, the length $L_8$ is about 40 millimeters. According to example embodiments, the applicator 1124 is preferably configured to be sized and shaped to comprise compatible fittings for engagement with enteral couplings, connectors, adapters, etc.

For example, the applicator 1124 comprises a first coupling portion 1152 and a second coupling portion 1154, both of which are generally adjacent each other and generally proximal the end of the applicator of the coupler 1100. In example embodiments, the first portion 1152 is preferably sized and shaped for compatible interengagement with enteral-only (EO) formatted couplings and the second portion 1154 is preferably sized and shaped for compatible interengagement with ISO 80369-3 formatted couplings (e.g., dimensionally generally similar to ISO 80369-3 formatted male transfer port). Thereafter the second portion 1154, an outer periphery portion of the coupler 1100 generally tapers to a generally larger diameter towards the coupling 1134. In example embodiments, the coupler 1100 can be optionally engaged with either of enteral-only (EO) or ISO 80369-3 ENFit formatted couplings to withdraw fluids from a bottle or other vessel containing fluids, and/or the coupler 1100 can engage either of the enteral-only (EO) or ISO 80369-3 ENFit formatted couplings for outputting fluids from the syringe and within a bottle, reservoir, etc. For example, the first portion 1152 can be compatible for engagement with a female enteral-only (EO) coupling or fitting and the second portion can be compatible for engagement with an ISO 80369-3 ENFit female connector or fitting. Furthermore, the coupler 1100 can be inserted within a patient's mouth for the oral administration of fluids. Preferably, a substantially smooth and radiused transition is provided between the first and second portions 1152, 1154, for example, such that insertion within a patient's mouth to deliver fluids does not present any harm or injury to the patient. Thus, according to one example embodiment the applicator 1124 comprises a stepped end with a generally rounded profile to mitigate trauma.

FIGS. 45-59 show example embodiments of an oral administration coupler comprising an ENFit compatible coupling (or ISO 80369-3 formatted coupling) and a generally elongate straw or flexible conduit or tube extending therefrom, for example, which is preferably beneficial when delivering medicine or fluids to the back of the human or animal patient's mouth. In example forms, the tube is generally between about 30-120 millimeters in length, and can be formed from any available French gauge (Fr) as desired. In some example embodiments, the tube 1216 comprises one or more graduations or markings 1217 thereon, for example, to assist in the measurement of the dosage quantity. Optionally, the tube 1216 can be substantially clear and free from any marking or graduations.

Figure 45:
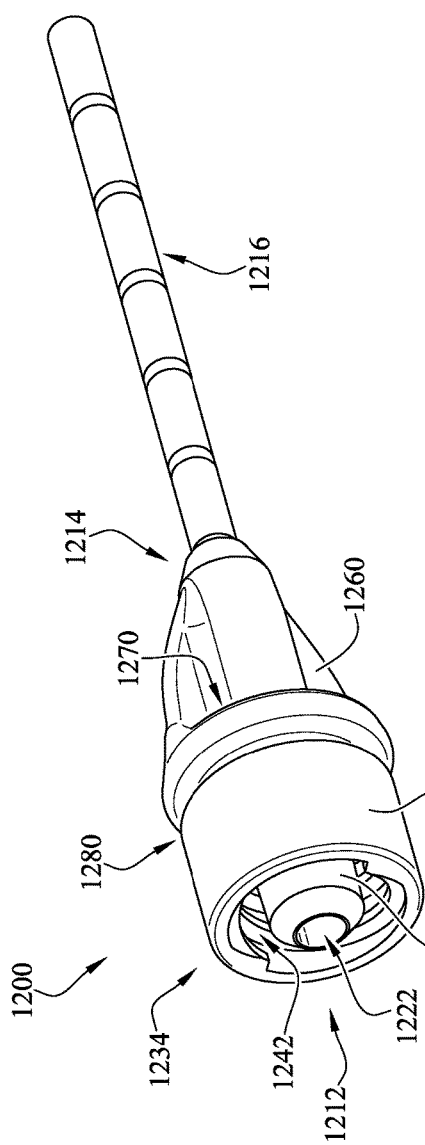
FIG. 45 shows a perspective view of an oral administration coupler according to another example embodiment of the present invention.
Figure 46:
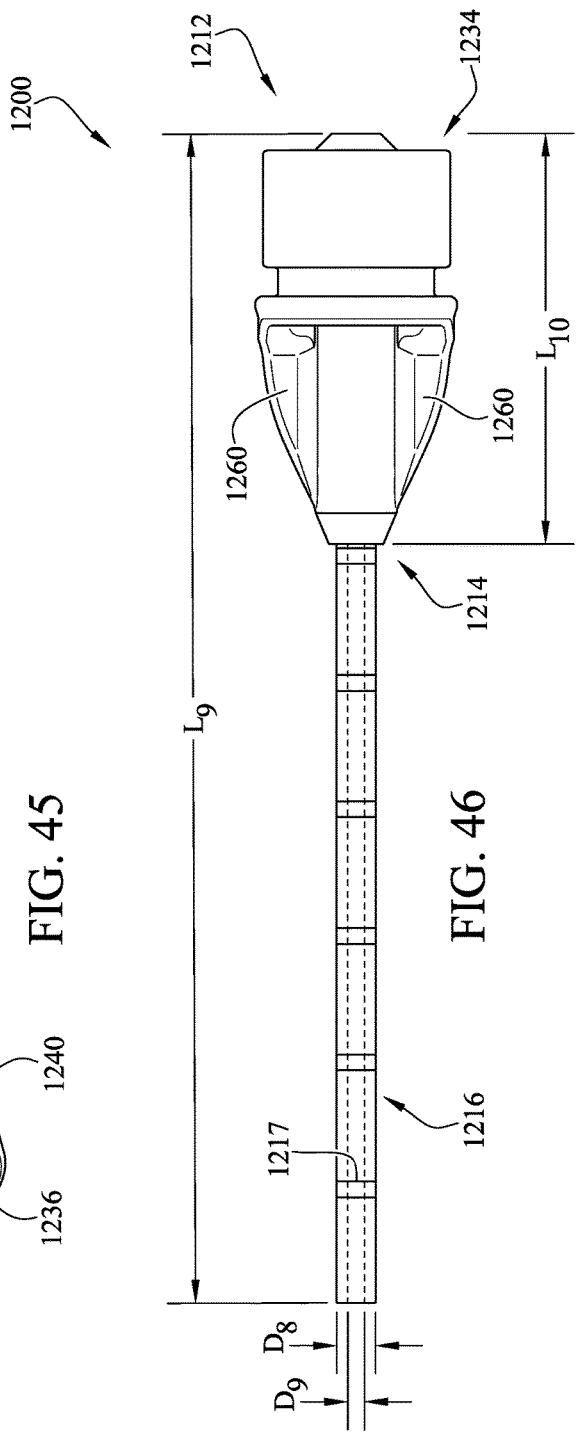
FIG. 46 shows a side view of the oral administration coupler of FIG. 45.

FIGS. 45-46 show an oral administration coupler 1200 comprising a hub comprising a syringe coupling end 1212 and an applicator coupling end 1214, and a generally elongate straw or flexible conduit or tube 1216 extending from the applicator coupling end 1214 such that an entire length $L_9$ of the coupler 1200 (defined between the end of the tube 1216 and the generally opposite syringe coupling end 1212) is generally between about 40 millimeters to about 60 millimeters. The length $L10$ of the hub (e.g., extending between syringe coupling end 1212 and applicator coupling end 1214) is generally between about 20 millimeters to about 30 millimeters, for example about 27 millimeters according to one example embodiment. According to one example embodiment, the length $L9$ is sufficient to deliver fluid from the conduit (e.g., central fluid transfer member) to a back of a child's mouth from a fluid delivery device at least partially external of the child's mouth. In example embodiments, the syringe coupling end 1212 is generally configured to be substantially similar to the ENFit compatible couplings as described above (e.g., 34), for example, comprising a transfer port 1236 and an outer collar member 1240 for providing sealing engagement with the female coupling FC of the syringe S. In example embodiments, the outer collar member 1240 comprises threads 1242 defined on an internal portion thereof, and the transfer port 1236 generally axially extends relative to the collar and comprises a conduit 1222 extending therethrough.

In example embodiments, at least one connecting portion or wing 1260 extends generally proximal the applicator coupling end 1214 to a portion of the outer collar member 1240, for example, to fix the outer collar member 1240 relative to the transfer port 1236. As such, at least one vent opening 1270 provided therebetween provides fluid drainage and airflow ventilation within an annular space defined between the outer collar member 1240 and the transfer port 1236 (see FIG. 47). U.S. Non-provisional patent application Ser. No. 14/844,956 shows a vented connector for medical fluid vessels including at least one connecting portion, an outer collar member, transfer port, and at least one vent opening, the entirety of which is incorporated herein by reference. According to example embodiments, the at least one connecting portion 1260 preferably can be useful for gripping by a user's fingers during attachment/detachment of the syringe coupling end 1212 with the female coupler of the syringe S. For example, preferably the at least one connecting portion 1260 comprises an outer periphery portion 1261 tapering from a portion proximal the syringe coupling end 1212 to a portion generally adjacent the applicator coupling end 1214. In example embodiments, the tapering transition of the at least one connecting portion 1260 preferably provides a smooth transition to mitigate trauma.

According to the embodiment depicted in FIGS. 45-46, the tube 1216 is substantially straw-like and is generally semi-rigid, for example, such that in a relaxed state the tube 1216 generally extends substantially linearly without maintaining a bend or curve-like shape. According to one example embodiment, the tube 1216 is formed from a 4 Fr gauge polyurethane straw comprising an outer diameter $D_8$ of between about 1.25 millimeters to about 1.45 millimeters and an inner diameter $D_9$ of between about 0.6 millimeters to about 1.35 millimeters (see also FIG. 60).

In other example embodiments, as will be described in greater detail below, the straw or tube of the oral administration coupler can be formed from one or more materials, for example, which can be flexible, partially flexible, substantially flexible, partially rigid, substantially rigid, or otherwise provide sufficient flexibility and rigidity as desired. In some example embodiments, the straw or tube comprises a feeding tube, conduit or vessel. Preferably, the one or more materials forming the tubes, straws, etc. can be polyvinyl chloride (PVC), silicon, polyurethane (PU), polypropylene (PP), or other materials as desired. In some example embodiments, the components of the coupler are integrally connected together as one piece. In other example embodiments, at least one component of the coupler is a separate piece and the components are assembled after the manufacture thereof. In yet another example embodiment, one or more components of the coupler can be manufactured by over-molding one or more components atop one or more separate components of the coupler. Preferably, in the case where the coupler comprises two or more separate pieces, one or more interengagement features, couplings, receivers, etc. can be provided to provide a coupled and substantially permanent connection between the two pieces. In example embodiments, the tube 1216 is attached and secured in place with a good seal with one or more portions of the coupler (e.g., applicator coupling end), for example, by conventional structures such as crimps, adhesives, or other attachment couplings (e.g., a barbed end and/or collar), etc.

FIGS. 47-48 show the oral administration coupler 1200 removably coupled with the female coupler FC of the syringe S. In example embodiments, a clamp can be provided for temporarily closing or sealing the tube 1216 when not in use (e.g., generally for purposes of storing or transporting). In some example forms, a tab ST can be provided on the syringe, for example, which comprises a slit or clamp-like feature STO (or slide lock) such that the tube can be temporarily clamped (see FIG. 47) or can generally extend longitudinally from the applicator coupling end 1214 (see FIG. 48) when it is desired to administer medicine or fluids to the back of the mouth of a human or animal patient. According to one example embodiment, the tab clamp feature STO comprises a generally rectangular channel that is generally sized to provide substantial frictional engagement with the tube 1216, for example, to generally clamp to the tube and substantially (if not entirely) close or seal the conduit thereof. Optionally, the clamp feature STO can comprise one or more rounded or radiused surfaces, for example, to generally confirm to the curvature of the tube 1216. In example embodiments, a cap, sleeve, sheath or other cover/protector can be provided for fitting on the tube for protection and sanitary purposes. Preferably, with the protector (e.g., sheath or other cover) fitted on the tube, the tube can still be clamped as desired. In some example forms, the sheath is sized to fit over the entirety of the tube and the ISO 80369-3 coupler. In other example forms, the sheath is sized to fit over the tube or at least a portion thereof. According to some example embodiments, the tube comprises a 4 Fr feeding tube and the clamp-like feature STO of the tab ST preferably is sized and shaped to clamp/seal the tube 1216 and conduit extending through the tube.

As depicted in FIGS. 49-50, the plunger P of the syringe S comprises a tube PE extending therefrom, which preferably extends through the tube 1216 that is extending from the coupler 1200. In example embodiments, the tube 1216 is preferably sized such that the inner diameter of the conduit extending therethrough is at least about the size of the outer diameter of the tube PE of the plunger. In some example embodiments, the plunger tube PE is preferably substantially solid without a conduit extending therethrough. Optionally, the plunger tube can comprise a conduit extending therethrough. Preferably, with the plunger P comprising a tube PE extending therefrom, the dosing accuracy is improved, for example, since the plunger tube PE occupies some (if not a substantial amount) of the volume defined within the tube 1216. In some example embodiments, an end of the plunger P where the tube PE connects is generally tapered to transition between the size of the tube PE and the plunger P. Optionally, the plunger P can have a generally standard plunging head with a generally centrally-positioned opening formed therein for receiving the tube PE. Optionally, other connecting members of various sizes, shapes, configurations, etc. can be provided as desired for coupling the plunger P with the tube PE.

Figure 54:
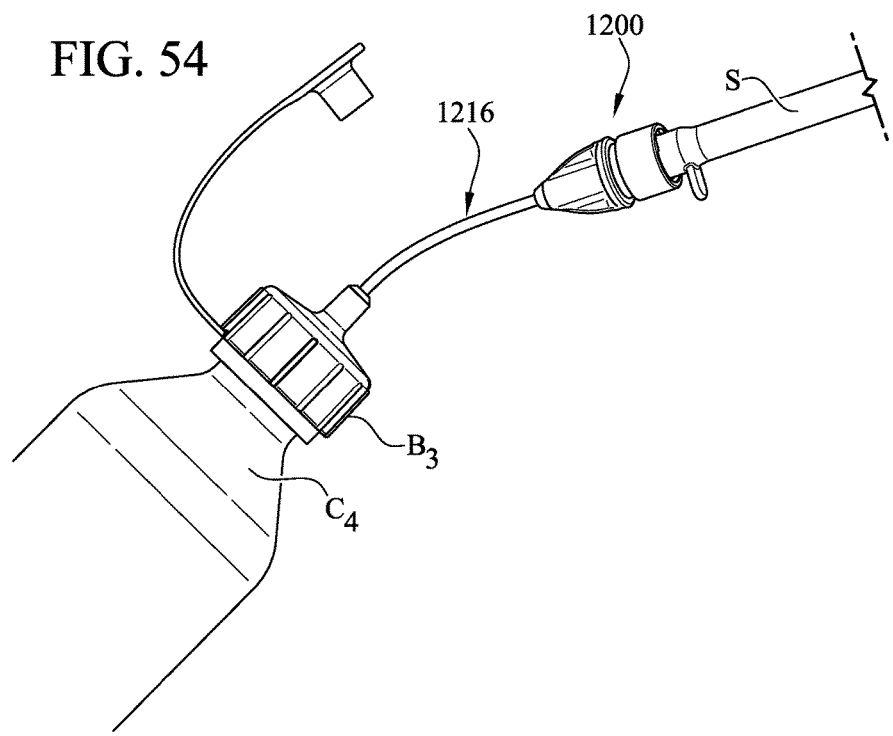
FIG. 54 shows an oral administration coupler and syringe assembly being used to draw fluids into the syringe body from a pharmacy bottle transfer lid and through a transfer port according to an example embodiment of the present invention.

FIGS. 51-54 show a plurality of embodiments of the oral administration coupler 1200 withdrawing fluids from an open container or for extending through a plurality of different pharmacy bottle adaptors. For example, FIG. 51 shows the oral administration coupler 1200 coupled with a syringe S and wherein the tube 1216 is inserted within an open container $C_1$ comprising a fluid to be delivered orally. FIG. 52 shows the tube 1216 fitted with a female enteral-only fitting of a pharmacy bottle adapter $B_1$ that is connected to a pharmacy bottle $C_2$. FIG. 53 shows the tube 1216 inserted through a lumen of a transfer port of an ENFit pharmacy bottle adapter that is coupled with an open end of a pharmacy bottle $C_3$. FIG. 54 shows the tube 1216 inserted through a lumen of a transfer port of an ENFit compatible (ISO 80369-3 formatted) transfer lid $B_3$, for example, which is preferably configured for engagement with an open end of a pharmacy bottle $C_4$. U.S. Non-provisional patent application Ser. Nos. 14/960,905 and 15/440,105 show transfer lids, caps, bottle adapters, etc. for use with pharmacy bottles or other containers, the entirety of which is incorporated herein by reference. According to one example embodiment, the tube 1216 is generally sized to allow for passing through the lumen of the bottle adapter.

Figure 55:
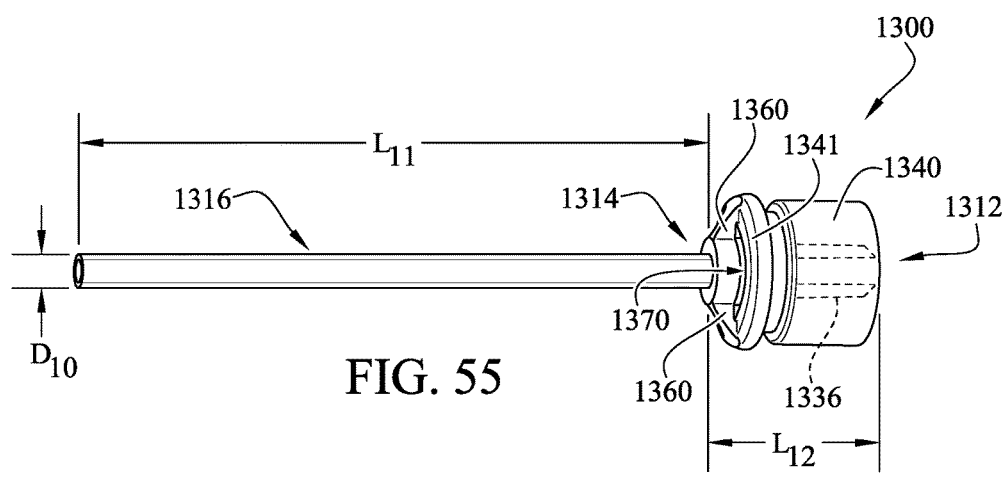
FIG. 55 shows a side view of an oral administration coupler according to another example embodiment of the present invention.
Figure 56:
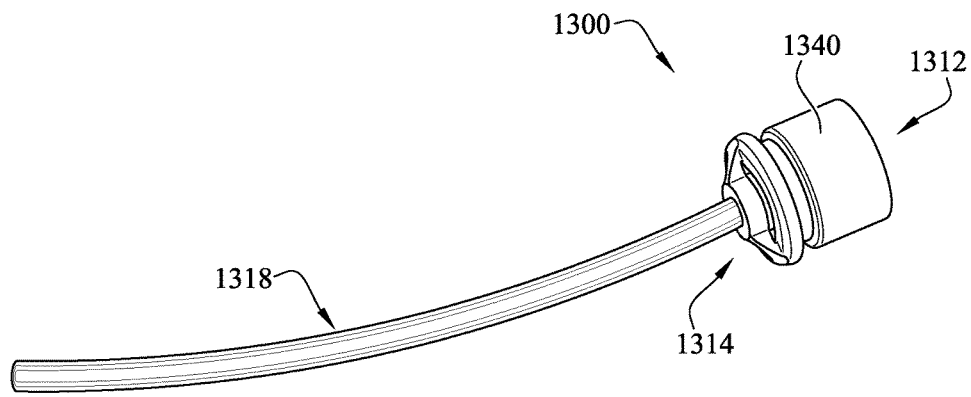
FIG. 56 shows a side perspective view of the oral administration coupler of FIG. 55, and showing a two-piece straw attached thereto and extending therefrom.
Figure 57:
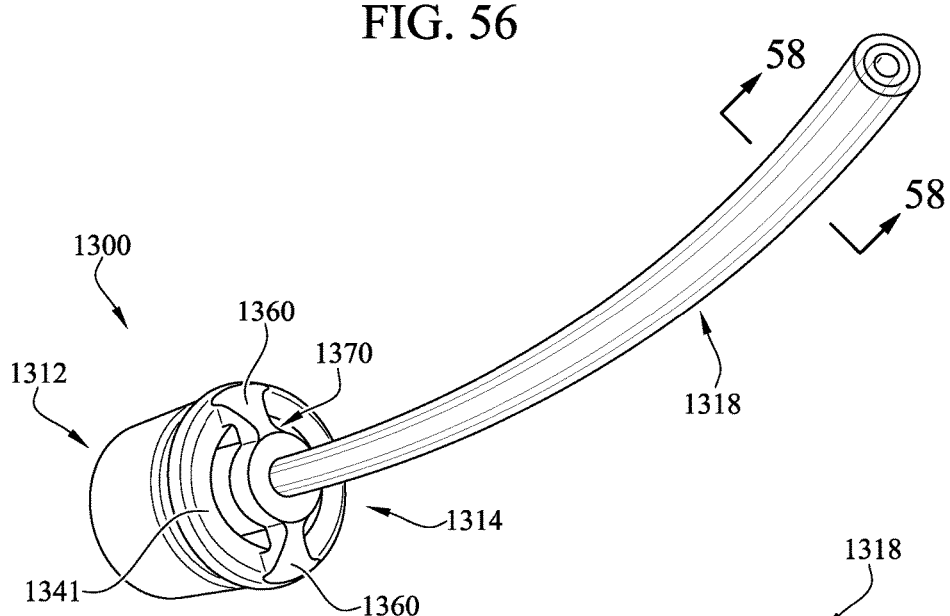
FIG. 57 shows a front perspective view of the oral administration coupler of FIG. 56.
Figure 58:
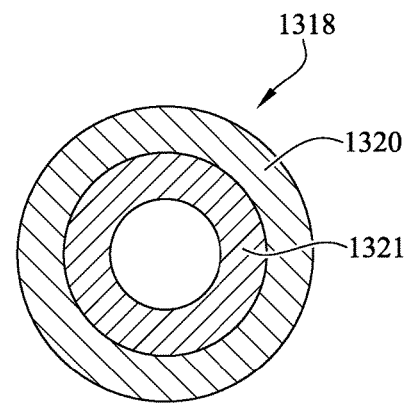
FIG. 58 shows a cross-sectional view of the tube of FIG. 56.

FIGS. 55-59 show additional example embodiments of oral administration couplers. For example, FIG. 55 shows an oral administration coupler 1300 that is generally similar to the oral administration coupler 1200 as described above. In example embodiments, the oral administration coupler 1300 comprises a hub or coupling comprising a syringe coupling end 1312 and an applicator coupling end 1314, and a generally elongate straw or flexible conduit or tube 1316 extending from the applicator coupling end 1314 such that an entire length ($L_{11}+L_{12}$) of the coupler 1300 (defined between the end of the tube 1316 and the generally opposite syringe coupling end 1312) is generally between about 30 millimeters to about 120 millimeters. According to one example embodiment, the length ($L_{11}+L_{12}$) is about 55 millimeters and the length $L_{11}$ of the tube 1316 is between about 30 millimeters to about 42 millimeters. In example embodiments, the syringe coupling end 1312 is generally configured to be substantially similar to the ENFit compatible couplings as described above (e.g., ENFit compatible coupling 34), for example, comprising a transfer port and an outer collar member for providing sealing engagement with the female coupling FC of the syringe S. In example embodiments, the outer collar member comprises threads defined on an internal portion thereof, and the transfer port 1336 generally axially extends relative to the collar and comprises a conduit extending therethrough.

In example embodiments, a length $L_{12}$ is defined between the syringe coupling end 1312 and the applicator coupling end 1314 of the hub. In example embodiments, the length $L_{12}$ is generally between about 10 millimeters to about 16 millimeters, for example between about 12 millimeters to about 15 millimeters according to one example embodiment. In example embodiments, at least one connecting portion 1360 extends generally proximal the applicator coupling end 1314 to an end surface 1341 of the outer collar member 1340 to fix the outer collar member 1340 relative to the transfer port 1336. As such, at least one vent opening 1370 is provided therebetween provides fluid drainage and airflow ventilation within an annular space defined between the outer collar member 1340 and the transfer port 1336. U.S. Non-provisional patent application Ser. No. 14/844,956 shows a vented connector for medical fluid vessels including at least one connecting portion, an outer collar member, transfer port, and at least one vent opening, the entirety of which is incorporated herein by reference. According to the depicted embodiment, the tube 1316 comprises a generally rigid and cylindrical polyurethane (PU) extrusion comprising a diameter $D_{10}$ of between about 1.5 millimeters to about 4 millimeters. Optionally, the material, flexibility, lengths $L_{11}$, $L_{12}$ and diameter $D_{10}$ can be chosen as desired.

According to one example embodiment, the oral administration coupler 1300 comprises a tube 1318 connected to and extending from the applicator coupling end 1314. The length of the coupler 1300 can be chosen as desired, for example, generally between about 20 millimeters to about 160 millimeters In example embodiments, the tube 1318 comprises an outer tube 1320 and an inner tube 1321 fitted within the lumen of the outer tube 1320, thereby resulting in reducing the diameter of the lumen. In example embodiments, the outer tube 1320 comprises an 8 Fr feeding tube and the inner tube comprises a 4 Fr feeding tube. Optionally, feeding tubes of other sizes or other extrusions formed from other materials can be configured for adapting to the configuration of the tube 1318. In other example embodiments, other couplers, for example, a coupler 1400 having a hub comprising a syringe coupling end 1412 and an applicator coupling end 1414 can be configured such that a tube 1416 can be secured with the applicator coupling end 1414 (see FIG. 59). In example embodiments, the coupler 1400 is generally similar to the coupler 300 as shown and described above. In example embodiments, the tube 1416 comprises an outer tube and an inner tube, for example, an 8 Fr outer tube and a 4 Fr inner tube. Optionally, other tubes of different size, material and configuration (e.g., flexibility, single, outer/inner, etc.) can be chosen as desired.

Figures 59, 60:
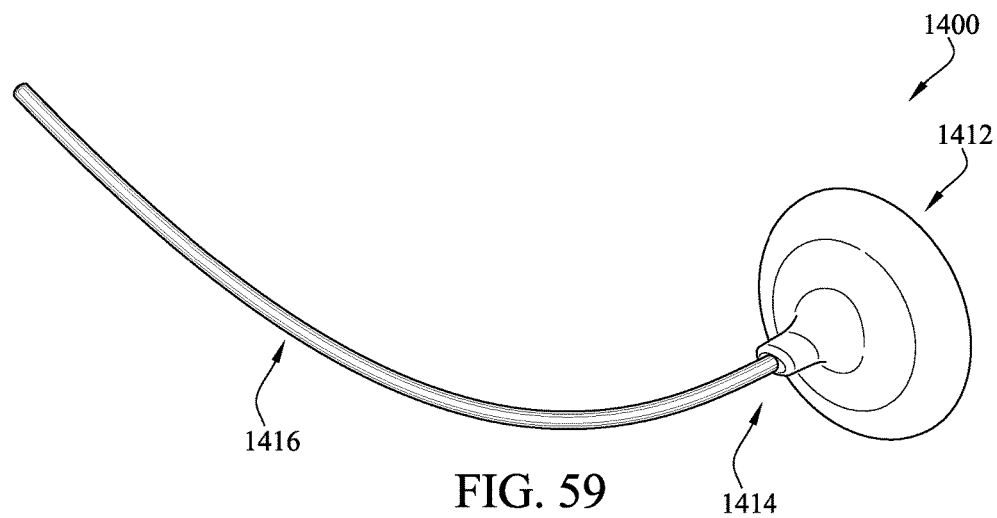
FIG. 59 shows an oral administration coupler according to another example embodiment of the present invention.
FIG. 60 shows a chart showing the priming volumes associated with feeding tubes of various lengths and internal diameters according to an example embodiment of the present invention.
Figure 64:
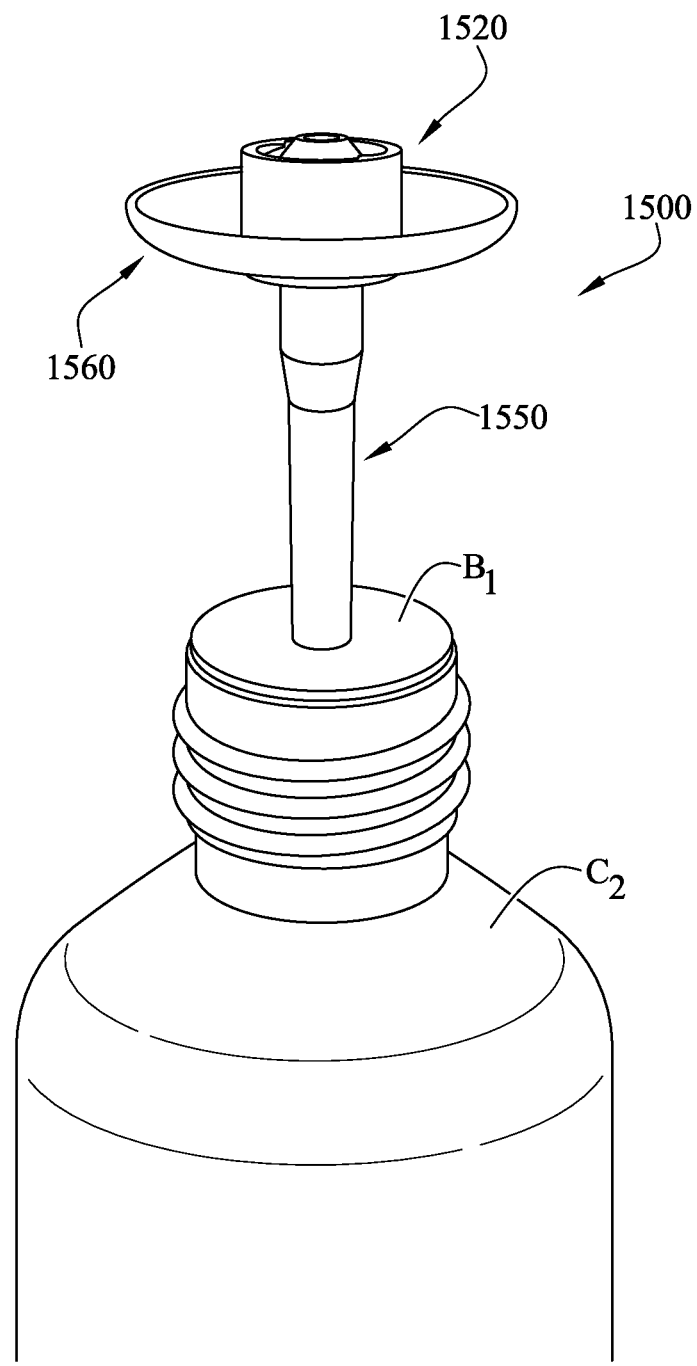
FIG. 64 shows the oral administration coupler of FIG. 61 coupled with a bottle adapter that is fitted with a pharmacy bottle.
Figure 65:
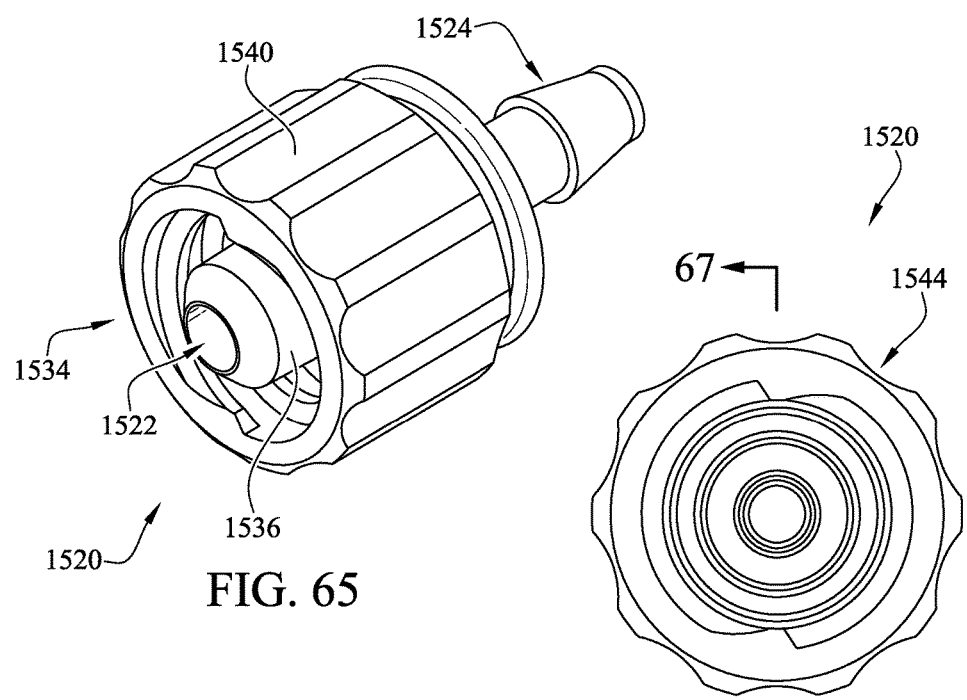
FIG. 65 shows a perspective view of a coupling of the oral administration coupler of FIG. 61.
Figure 66:
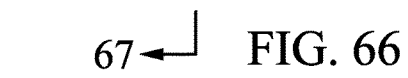
FIG. 66 shows a top view of the coupling of FIG. 65.
Figure 67:
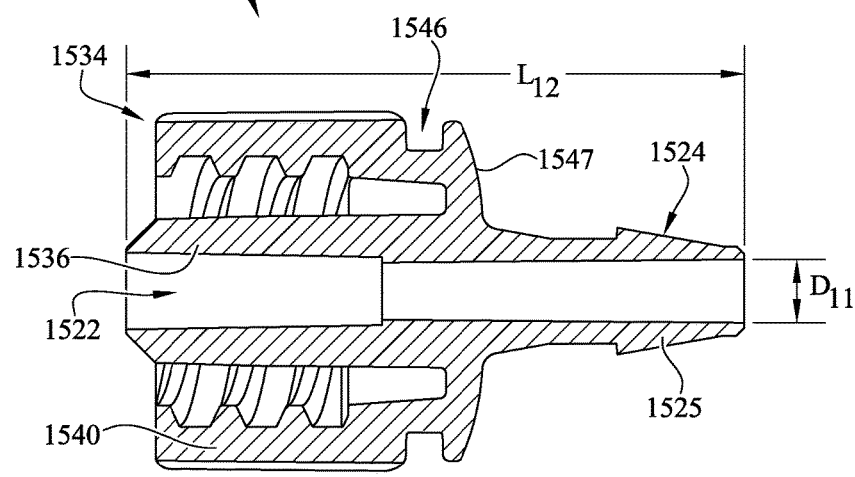
FIG. 67 shows a cross-sectional view of the coupling of FIG. 66 taken along line 67-67.

FIG. 60 shows a plurality of volume calculations according to an example embodiment of the present invention. For example, the volume of the lumen of the tube was calculated based upon the length and inner diameter of the tube. When the inner diameter of the tube is about 1.35 millimeters, a 30 millimeter tube comprises a volume of about 0.043 cubic milliliters, a 40 millimeter tube comprises a volume of about 0.057 cubic milliliters, a 60 millimeter tube comprises a volume of about 0.086 cubic milliliters, and a 100 millimeter tube comprises a volume of about 0.143 cubic milliliters. According to another example embodiment, when the inner diameter of the tube is about 0.60 millimeters, a 30 millimeter tube comprises a volume of about 0.008 cubic milliliters, a 40 millimeter tube comprises a volume of about 0.011 cubic milliliters, a 60 millimeter tube comprises a volume of about 0.017 cubic milliliters, and a 100 millimeter tube comprises a volume of about 0.028 cubic milliliters. In other example embodiments, for example, to at least ensure the tube lumen volume about 0.1 milliliter or less, a 30 millimeter tube could have an inner diameter up to about 1.03 millimeters, a 40 millimeter tube could have an inner diameter up to about 0.89 millimeters, a 60 millimeter tube could have an inner diameter up to about 0.73 millimeters, and a 100 millimeter tube could have an inner diameter up to about 0.56 millimeters. Optionally, tubes of other lengths, inner and outer diameters, materials, etc. can be incorporated for use with any of the couplers described herein.

FIGS. 61-80 show a plurality of oral administration couplers according to additional example embodiments of the present invention. FIGS. 61-67 show an oral administration coupling 1550 according to one example embodiment of the present invention. In example embodiments, the oral administration coupler 1500 comprises a syringe coupling portion 1520 (see FIGS. 65-67), a tube or straw portion 1550, and an outer collar or flange portion 1560. Optionally, a cover or capping portion 1570 can be provided for closure of a lumen 1552 of the straw 1550. In example embodiments, the syringe coupling portion 1520 comprises a lumen 1522 extending entirely therethrough between an ENFit compatible coupler (or ISO 80369-3 formatted coupling) 1534 and a straw connecting portion 1524. As similarly described above, the ENFit compatible coupler 1534 comprises a transfer port 1536 and an outer collar member 1540, and optional threads formed on an internal portion of the outer collar member 1540. The straw connecting portion 1524 comprises a barbed end 1525 that preferably provides for sealing engagement with an end of the straw 1554. In example embodiments, the coupling portion 1520 comprises a length $L_{12}$ of between about 22 millimeters to about 24 millimeters, for example about 23.32 millimeters according to one example embodiment. A diameter $D_{11}$ defines the size of the lumen 1522, for example, which is generally between 1.5 millimeters to about 5 millimeters, for example about 3.2 millimeters according to one example embodiment of the present invention. In some example embodiments, the outer collar member 1540 can comprises one or more surface features 1544, for example, to assist a user in gripping the collar 1540 for attachment of the coupling 1500 with the female coupling FC of the syringe S. In example forms, the surface features 1544 can be formed from one or more undulating patterns extending circumferentially along the outer periphery of the outer collar member 1540. Optionally, other recesses, protrusions, wings, knurls, holes, or other features can be formed with or removed from the outer collar member 1540 as desired, for example, to provide a gripping surface or feature for grasping during installation of the syringe.

In example forms, a radial channel 1546 is formed generally near a midpoint of the coupling portion 1520, for example, generally offset from an end surface 1547 of the coupling portion. As depicted in FIGS. 61-62, the flange portion 1560 comprises a central opening (unshown) for fitting in the radial channel 1546. In example embodiments, the central opening of the flange portion 1560 and the radial channel 1546 are preferably sized such that a secure connection is provided therebetween. As described above, the flange portion 1560 can comprise a smooth radiused transition or outer surface 1564. Optionally, the flange portion 1560 can be shaped and sized as desired, for example, and comprise one or more openings or vents extending therethrough. The straw 1550 comprises the lumen 1552 extending entirely therethrough and comprises a first end 1554 sealingly engaged with the straw connecting portion 1524 of the coupling portion and a second end 1556 forming an end for insertion within a human or animal patient's mouth for administering fluids orally. As described above, a cover or cap 1570 comprising a cylindrical collar 1572 extending therefrom can be removably engaged with the second end 1556 of the straw 1550.

Figure 68:
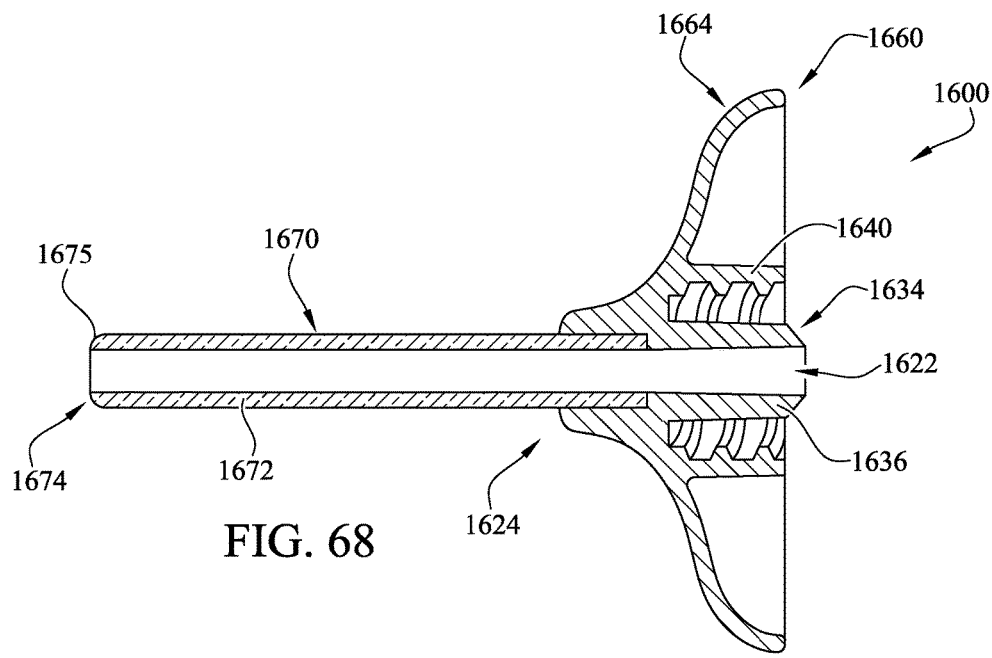
FIGS. 68-69 show an oral administration coupler according to another example embodiment of the present invention.
Figure 69:
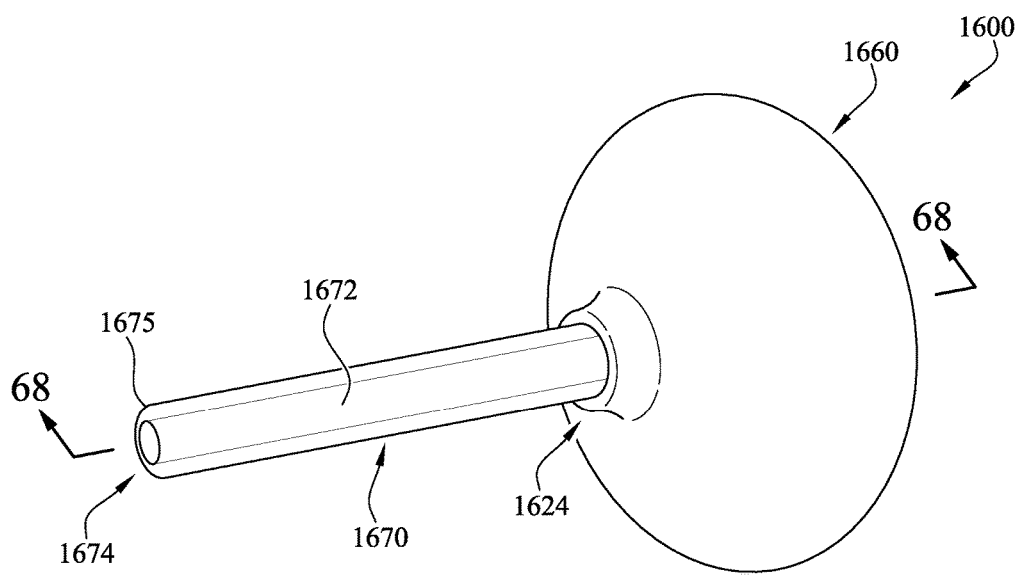

FIGS. 68-69 shows an oral administration coupler 1600 according to another example embodiment of the present invention. As depicted, the coupler 1600 comprises a lumen 1622 extending entirely through the coupler 1600 from a transfer port 1636 of an ENFit compatible coupling 1634 to an end 1674 of a straw 1670 extending from an applicator coupling end 1624. In example embodiments, the coupler 1600 comprises a flange portion 1660 substantially similar to the flanges as described above. In example embodiments, a smooth radiused transition or outer surface 1564 is provided along an outer periphery of the flange portion 1660. Optionally, one or more vents or openings can be formed in the flange 1660 as desired.

Figure 70:
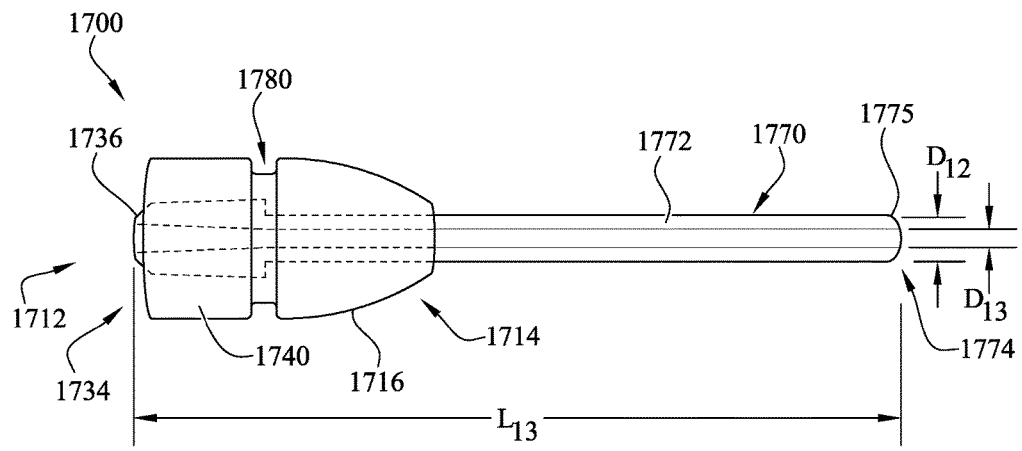
FIGS. 70-72 show an oral administration coupler according to another example embodiment of the present invention.
Figure 71:
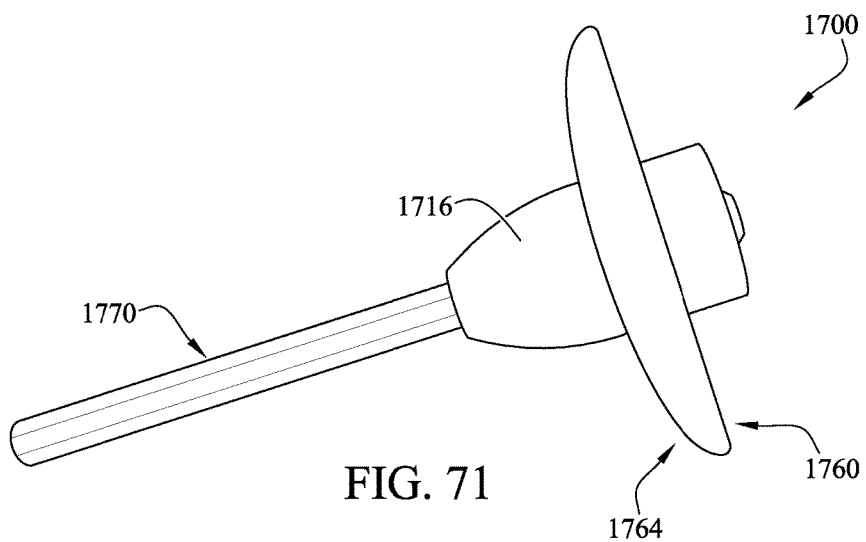
Figure 72:
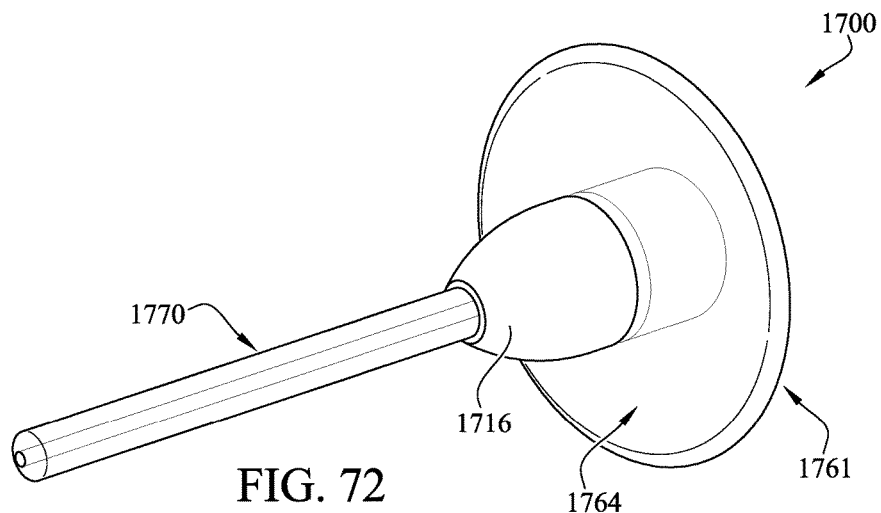

FIGS. 70-80 show a plurality of oral administration couplers 1700, 1800, 1900 and 2000 according to additional example embodiments of the present invention. FIGS. 70-72 show a coupler 1700 comprising a generally profiled applicator coupling end 1714, for example, generally having a taper or comprising a generally smooth and tapering transition 1716 along a generally curved path defined between the applicator coupling end 1714 and the ENFit compatible coupling end 1734. A straw 1770 can be generally frictionally fitted with the applicator coupling end 1714, or for example, an adhesive or coupling member can be provided for securing the straw to the applicator coupling end 1714. In example embodiments, the applicator coupling end 1714 comprises a female port or receiver (in communication with the lumen 1722) for receiving at least a portion of the straw 1770.

A smooth radiused or rounded transition or curved outer surface 1764 is provided on a flange portion 1760 according to an alternative example embodiment of the invention. Optionally, as depicted in FIG. 70, the flange 1760 need not be provided. According to some example embodiments, as described similarly above, the flange portion 1760 generally comprises a central opening that is fitted within a radial channel 1780 formed in the coupling between the ends 1714, 1712. For example, according to some example embodiments, a generally solid or opaque flange 1760 can be provided. As depicted in FIG. 72 the flange 1760 can be at least partially translucent or transparent. For example, according to some example embodiments, the flange 1761 is formed from a clear material (partially transparent or translucent) to allow for a line of sight into a patient's mouth during insertion of the end 1774 of the straw 1770. According to example embodiments, the end 1774 comprises a profiled or rounded tip surface 1775, and the smooth and tapering transition 1716 provide reduction to the risk of trauma during the insertion of the tube 1770 in the mouth of the patient. According to some example embodiments, the entirety of the coupling 1700 can be formed from a clear material.

Figure 73:
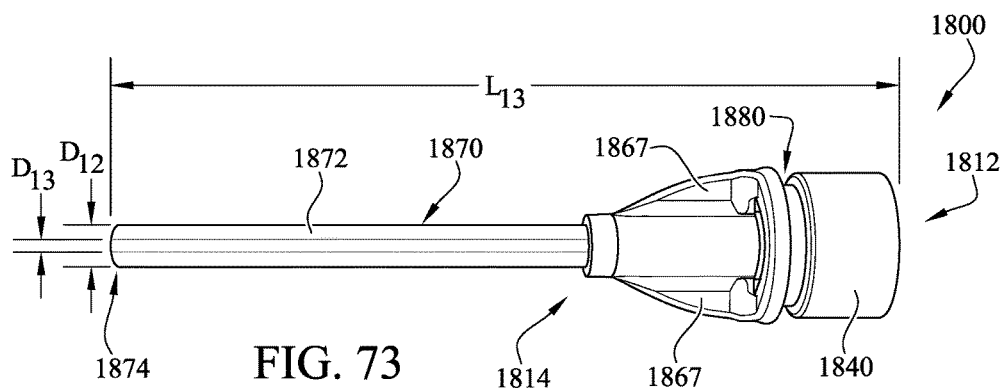
FIGS. 73-75 show an oral administration coupler according to another example embodiment of the present invention.
Figure 74:
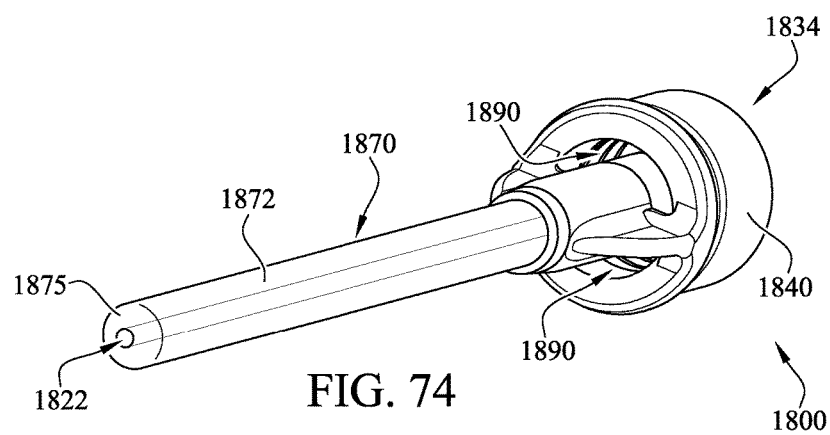
Figure 75:
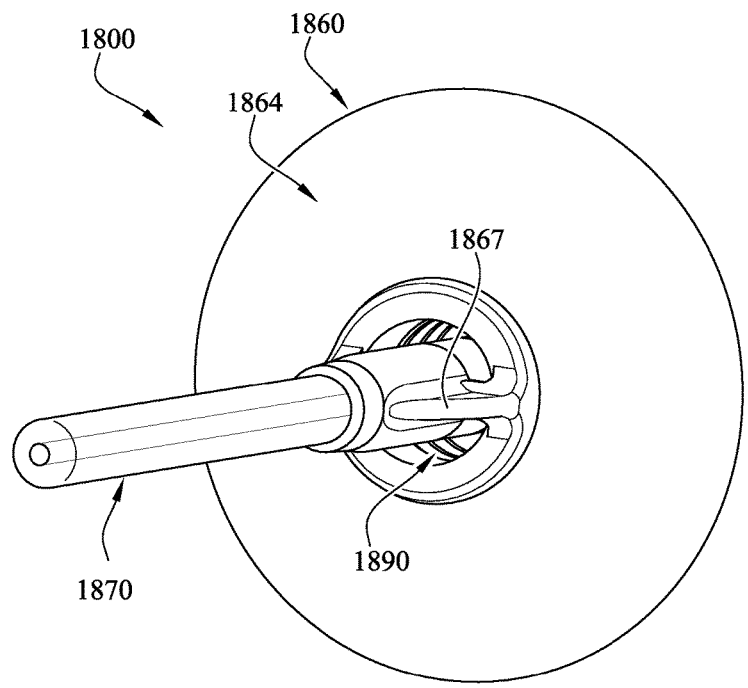
Figure 76:
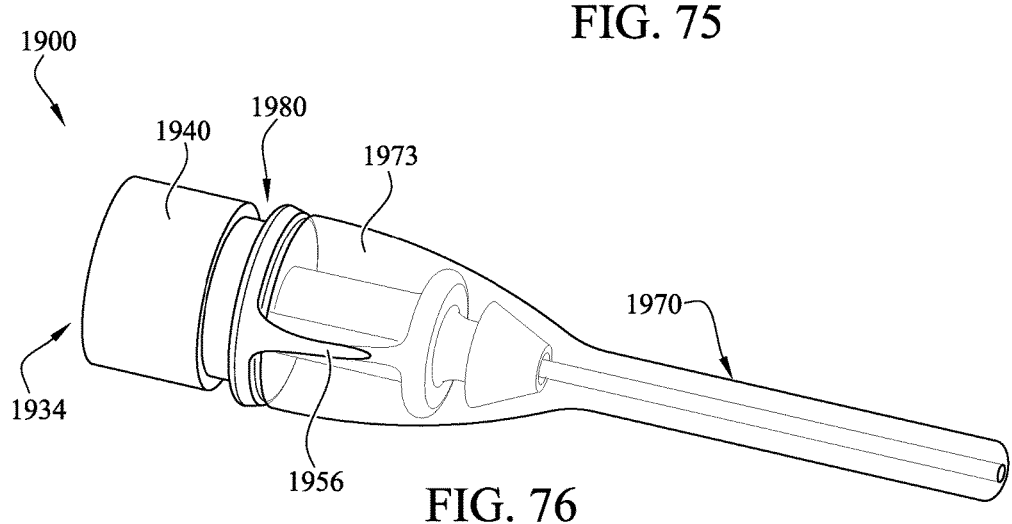
FIGS. 76-78 show an oral administration coupler according to another example embodiment of the present invention.
Figure 77:
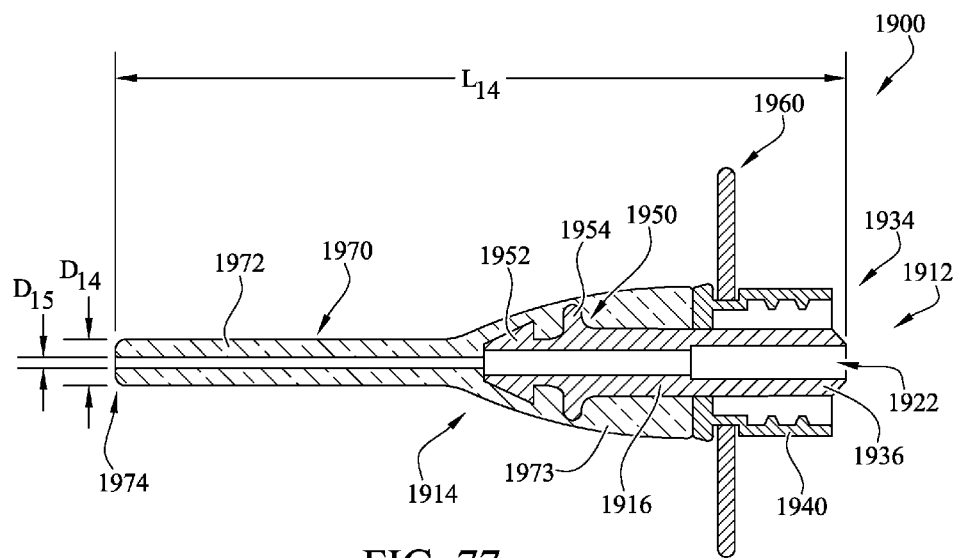
Figure 78:
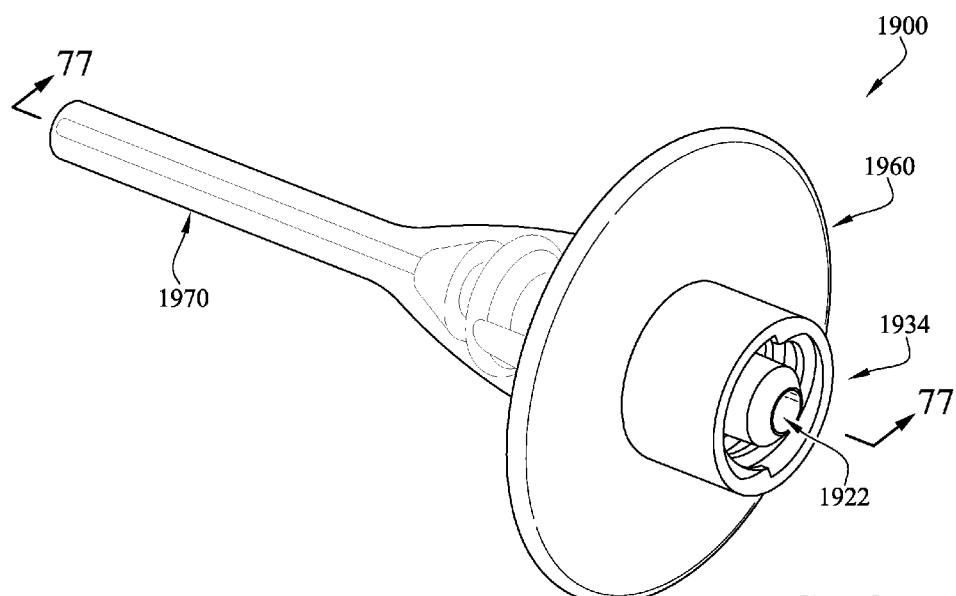

FIGS. 73-75 show an oral administration coupler 1800 according to another example embodiment of the present invention. In example embodiments, the coupler 1800 comprises a syringe coupling end 1812 and an applicator coupling end 1814, and a generally elongate straw or flexible conduit or tube 1870 extending from the applicator coupling end 1814 such that an entire length $L_{13}$ of the coupler 1800 (defined between the end of the tube 1874 and the generally opposite syringe coupling end 1812) is generally between about 40 millimeters to about 60 millimeters. As similarly described with respect to the coupler 1200, the coupler 1800 comprises an ENFit compatible coupling 1834 defining a transfer port, an outer cylindrical collar 1840, an applicator coupling end 1814, at least one connecting member 1867, a straw 1870 comprising a generally elongate cylindrical body 1872 and a rounded surface 1875 formed on an end portion 1874 thereof. In example embodiments, the straw 1870 generally comprises an outer diameter $D_{12}$ of between about 2 millimeters to about 6 millimeters, for example about 4 millimeters or about a 12 Fr polyvinylchloride (PVC) cylindrical extrusion 1872. In example embodiments, an inner diameter $D_{13}$ of the straw 1870 is between about 0.30 millimeters to about 2 millimeters, for example about 0.56 millimeters according to one example embodiment. Optionally, other materials of various sizes (e.g., diameters and length) can be chosen as desired. At least one vent 1890 can be provided as desired and a flange 1860 can be removably coupled with a radial channel 1880. U.S. Non-provisional patent application Ser. No. 14/844,956 shows a vented connector for medical fluid vessels including at least one connecting portion, an outer collar member, transfer port, and at least one vent opening, the entirety of which is incorporated herein by reference.

FIGS. 76-80 show an oral administration coupler 1900 according to another example embodiment of the present invention. As depicted, the coupler 1900 is generally formed by an over-molding process, for example, wherein a portion of the component is formed from a first material, and a second component is molded over the first component and formed from a second material. For example, in example embodiments, the first component or hub comprising the ENFit compatible coupling 1934 is formed from Acrylonitrile-Butadine-Styrene (ABS) and the second component comprising the straw 1970 is formed from silicone. In example embodiments, the hub comprises the ENFit compatible coupling 1934 at one end and a barb or anchor portion 1950 at the other generally opposite end. A lumen 1922 extends entirely through the hub between the ends. In example embodiments, the anchor portion or applicator coupling end 1950 comprises a barbed end 1952 and a collar 1954 offset therefrom for providing interengagement with the over-molded straw such that the two components remain engaged together.

Figure 79:
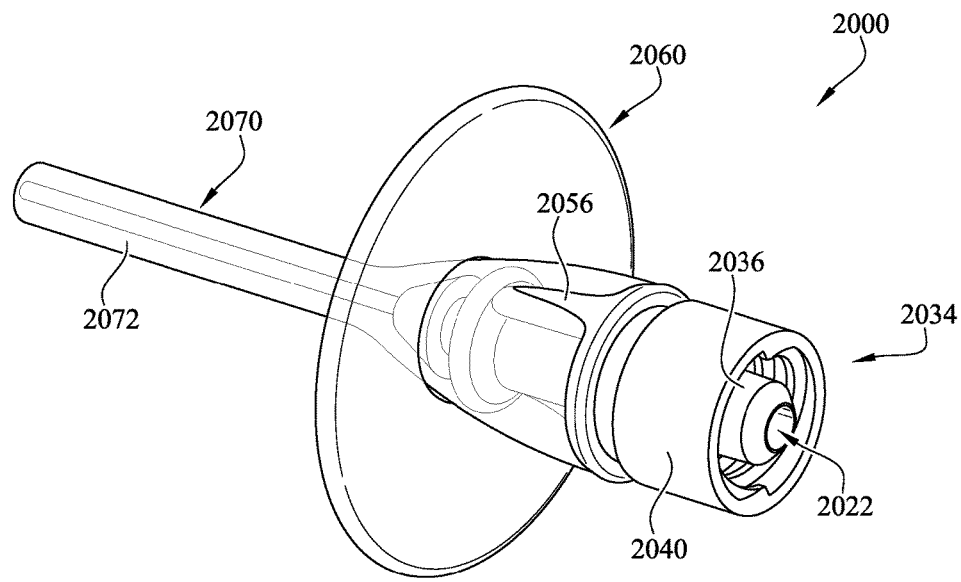
FIGS. 79-80 show an oral administration coupler according to another example embodiment of the present invention.
Figure 80:
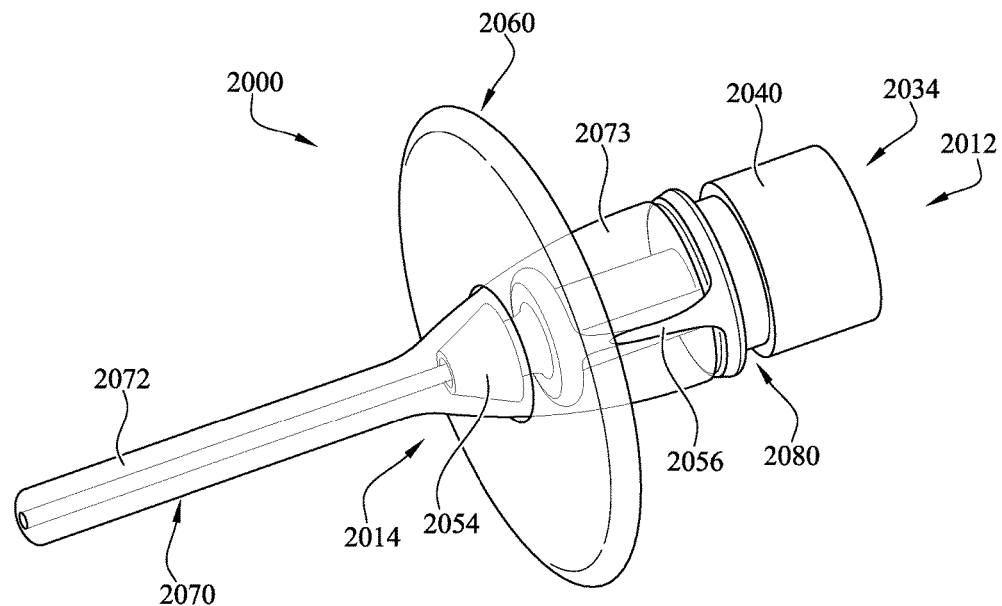

In example embodiments, the straw 1970 comprises a generally cylindrical body 1972 and an outer over-molded portion 1973 for transitioning to an outer collar portion 1940, and for example engaging with the barbed portion 1952 and offset collar 1954. Optionally a radial channel 1980 is formed on a portion of the hub near the midpoint thereof, for example, which can be configured to receive a flange 1960 or accept a tethered cap or other closure member for engaging the ENFit compatible coupling 1934. According to example embodiments, one or more connecting portions or wings 1956 can extend between the barbed end 1914 and the outer cylindrical collar 1940, and thus according to some example embodiments at least a portion of the wings 1956 generally remain exposed above the outer surface of the outer over-molded portion 1973. In example embodiments, a length $L_{14}$ is defined between the ends of the coupler 1900. In example embodiments, the length $L_{14}$ is between about 20 millimeters to about 160 millimeters. In example embodiments, the straw cylindrical body 1972 comprises an outer diameter $D_{14}$ and an inner diameter $D_{15}$. In example embodiments, the diameter $D_{14}$ is between about 2 millimeters to about 6 millimeters, for example about 4 millimeters or about a 12 Fr. In example embodiments, the inner diameter $D_{15}$ of the straw 1870 is between about 0.30 millimeters to about 2 millimeters, for example about 0.56 millimeters according to one example embodiment. FIGS. 79-80 show a substantially similar oral administration coupler 2000. According to one example embodiment, a flange 2060 is formed with the outer over-molded portion 2073 as an integral component, for example, rather than being a separate piece and engaging with the radial channel 2080. In example embodiments, the flange 2060 is preferably also formed from a silicone or generally at least partially translucent or transparent material such that a line of sight can be provided when inserting the straw 2070 in the mouth and administering the dose to the patient.

Figure 81:
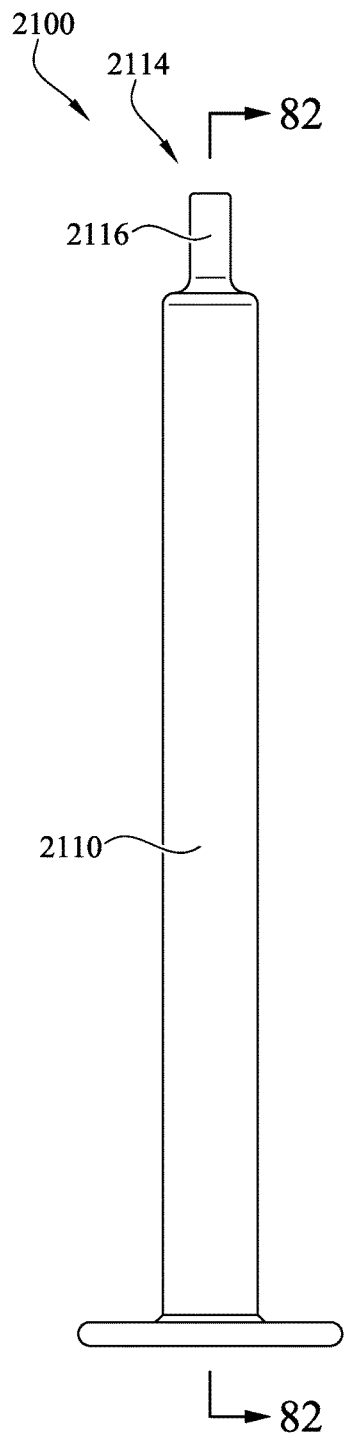
FIGS. 81-82 show a syringe-type oral delivery device according to an example embodiment of the present invention.
Figure 82:
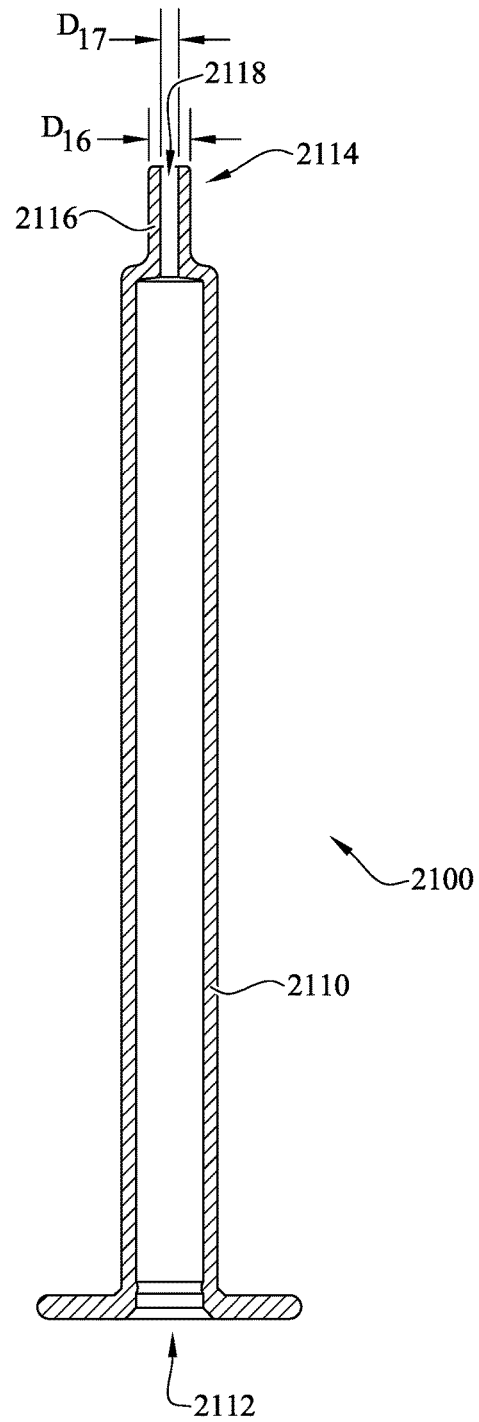
Figures 83, 84, 85:
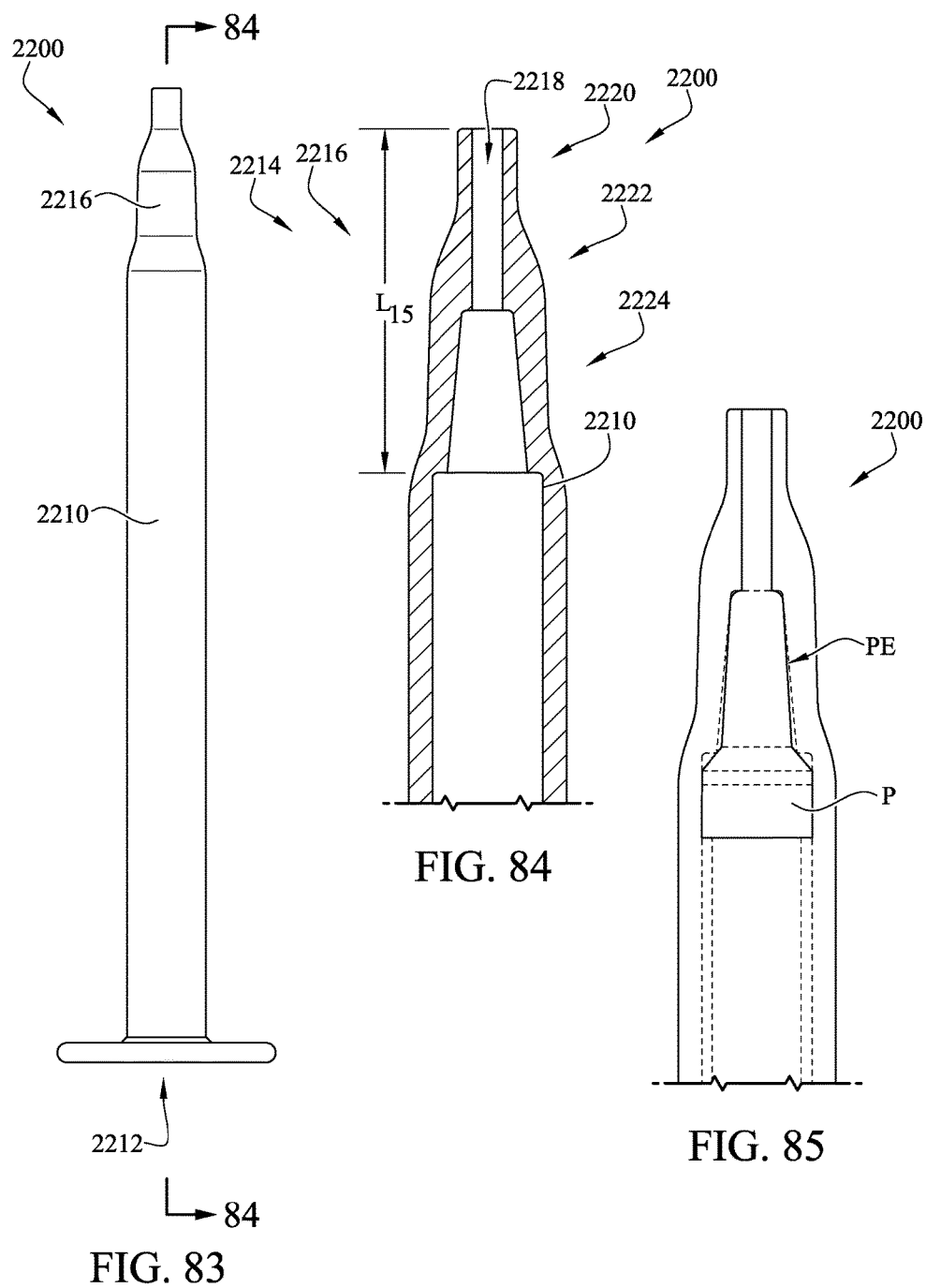
FIGS. 83-85 show a syringe-type oral delivery device according to another example embodiment of the present invention.

FIGS. 81-89 show a plurality of syringe-type oral administration delivery devices according to additional example embodiments of the present invention. For example, FIGS. 81-82 show a syringe delivery device 2100 according to one example embodiment of the present invention. As depicted, the syringe delivery device 2100 generally comprises a generally elongate barrel 2110 extending from a base end 2112 to an administration end 2114. In example embodiments, the administration end 2114 comprises a lumen extension tip, oral administration applicator or transfer port 2116 comprising a lumen 2118 extending therethrough. In example embodiments, the transfer port 2116 comprises an outer diameter $D_{16}$ and an inner diameter $D_{17}$. The outer diameter $D_{16}$ is generally between about 2 millimeters to about 3 millimeters, for example about 2.5 millimeters according to one example embodiment. The inner diameter $D_{17}$ is generally between about 0.5 millimeters to about 2.5 millimeters, for example about 1.40 millimeters according to one example embodiment. In example embodiments, rather than coupling an oral administration coupler to a syringe for orally administering fluids or medicine by an oral delivery applicator, tube, straw, etc., the transfer port 2116 of the syringe can be inserted directly in the patient's mouth and the fluids can be delivered. In example embodiments, the accuracy of the dose being delivered by the syringe 2100 is substantially accurate. According to one example embodiment, the syringe is generally capable of containing about 1 milliliters of fluid or medicine. In other example embodiments, the syringe is sized to contain up to about 60 milliliters of fluid or medicine. In some example embodiments, a plunger comprising a modified tip can be utilized, for example, which is generally sized and shaped to fit entirely within the lumen of the transfer port 2116 such that the contained volume is substantially zero, and thus, dosing inconsistencies and anomalies in accuracy during fluid delivery are substantially, if not entirely, eliminated. U.S. Non-provisional patent application Ser. No. 15/210,282 shows a syringe comprising a lumen extension tip or transfer port and having a plunger for substantially entirely fitting within the lumen of the transfer port, the entirety of which is incorporated herein by reference.

FIGS. 83-87 show a syringe-type delivery device 2200 according to another example embodiment of the present invention. In example embodiments, the device 2200 is generally similar to the device 2100 as described above and comprises a generally elongate barrel 2210 extending from a base end 2212 to an administration end 2214. According to example embodiments, an administration end 2214 comprises a transfer port 2216 extending a length $L_{15}$ of between about 5 millimeters to about 15 millimeters. In example embodiments, the administration end 2214 is generally similar to the applicator end of the coupler 1100. For example, the administration end 2214 comprises a stepped profile comprising a first coupling portion 2220, a second coupling portion 2222, and a third coupling portion 2224. In example embodiments, the stepped profile comprises generally smooth and radiused transitions between the coupling portions.

In example embodiments, the first coupling portion 2220 comprises a transfer port substantially sized and shaped similarly to the transfer port 2116 as described above. The second coupling portion is preferably sized and shaped for compatible interengagement with enteral-only (EO) formatted couplings, and the third coupling portion 2224 is preferably sized and shaped for compatible interengagement with ISO 80369-3 formatted couplings (e.g., dimensionally generally similar to ISO 80369-3 formatted male transfer port). Thereafter the third coupling portion 2224, an outer periphery portion of the transfer port 2216 generally tapers outwardly to the syringe body 2210. Thus, according to example embodiments, the transfer port 2216 preferably comprises a plurality of coupling portions for providing compatible coupling engagement with a plurality of enteral couplings or formats (e.g., enteral-only (EO) or ISO 80369-3 ENFit format). According to example embodiments, a plunger P comprising an end plunging element PE can be configured for use therewith. In example embodiments, the end plunging element PE comprises a stepped profile such that when the plunger P is fully inserted within the syringe barrel 2210 the contained volume therein is substantially zero. Thus, full insertion of the plunger P within the barrel 2210 is such that the plunging element PE substantially occupies the entirety of the lumen 2218 of the transfer port 2216.

Figures 86, 87:
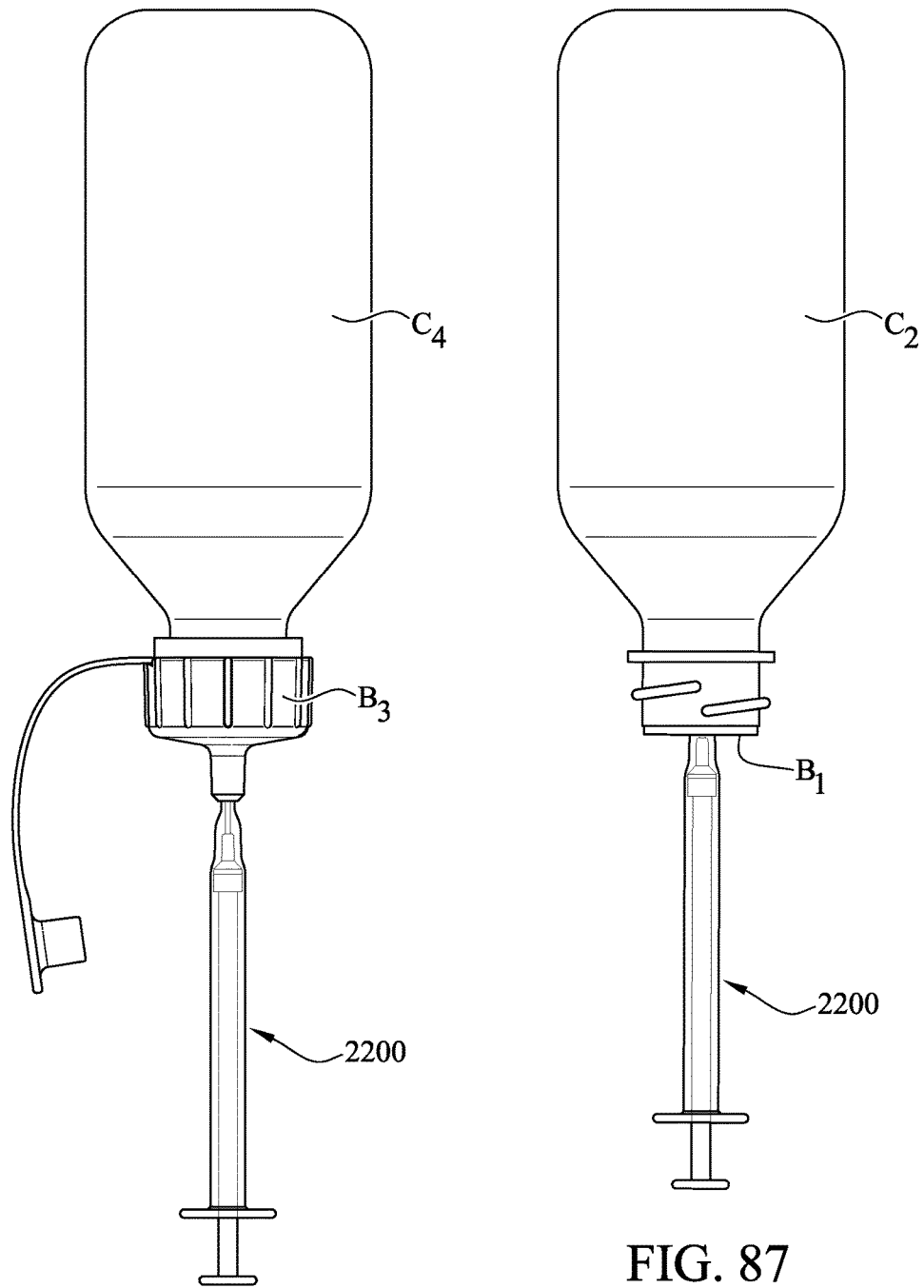
FIG. 86 shows the syringe-type oral delivery device of FIG. 83 coupled with a male port of a transfer lid according to an example embodiment of the present invention.
FIG. 87 shows the syringe-type oral delivery device of FIG. 83 coupled with a pharmacy bottle adapter according to an example embodiment of the present invention.

For example, as depicted in FIG. 86, the first coupling portion 2220 is engaged with a transfer lid $B_3$ that is connected to a pharmacy bottle $C_4$. As shown, the first coupling portion 2220 is generally inserted within a lumen defined within a male transfer port of the of the transfer lid $B_3$. According to another example embodiment as depicted in FIG. 87, the syringe device 2200 is coupled with a press-in bottle adapter $B_1$ that is coupled with a pharmacy bottle $C_2$. In example embodiments, the second coupling portion 2222 is engaged within a female port of the bottle adapter $B_1$. In example embodiments, the bottle adapter $B_1$ is generally formed from an enteral-only (EO) formatted coupling and the transfer lid $B_3$ comprises a compatible ISO 80369-3 ENFit formatted port. As such, the syringe delivery device 2200 comprises an applicator end 2214 that is preferably compatible for coupling engagement with both enteral-only (EO) and ISO 80369-3 ENFit formatted couplings to allow for withdrawing fluids from a container. Furthermore, the applicator end 2214 can further be used for direct insertion into a patient's mouth for the oral delivery of fluids. In example embodiments, the stepped profile with smooth transitions between the coupling portions preferably mitigates the likelihood of trauma during oral administration and delivery.

Figures 88, 89:
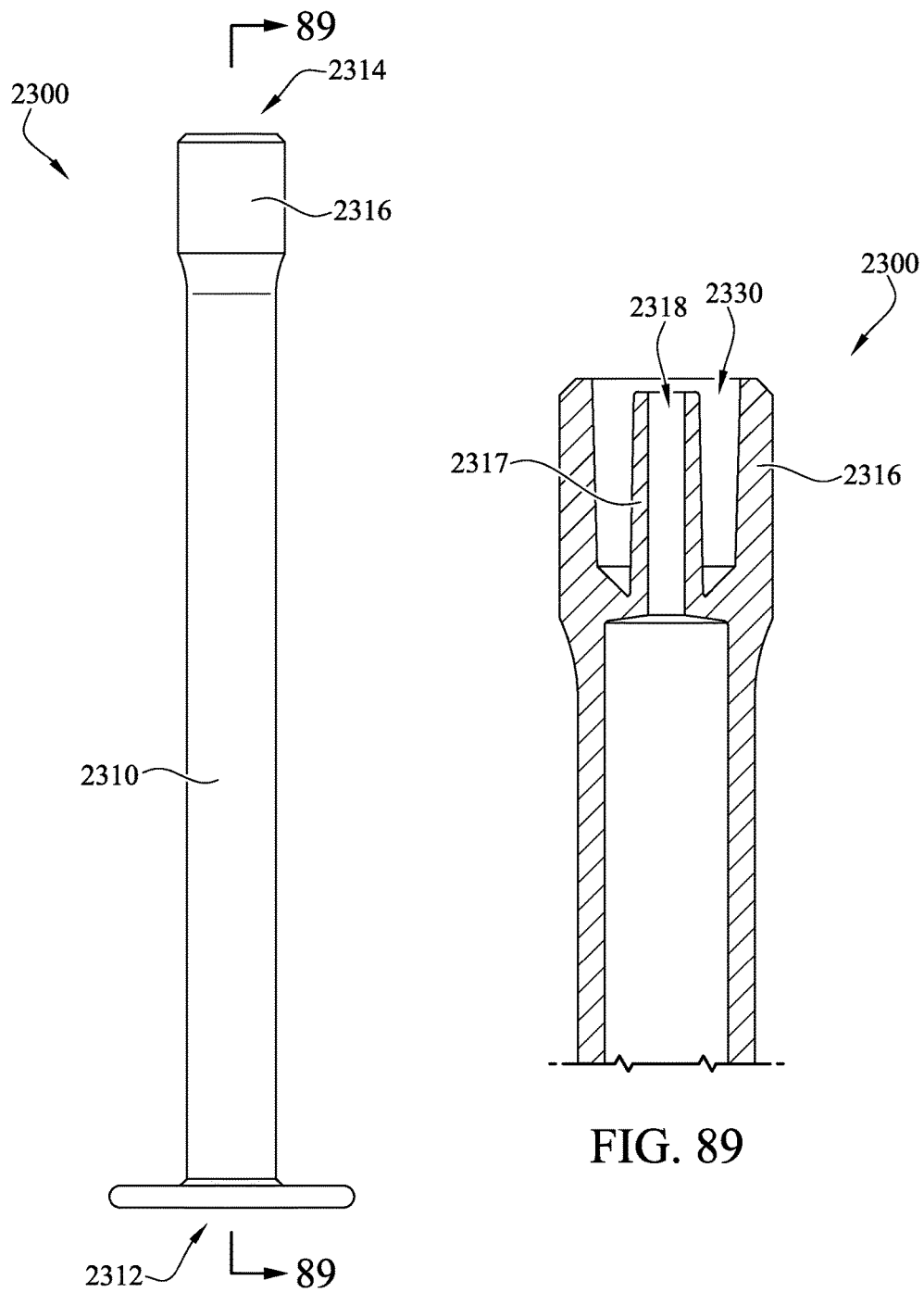
FIGS. 88-89 show a syringe-type oral delivery device according to another example embodiment of the present invention.

FIGS. 88-89 show a syringe delivery device 2300 according to another example embodiment of the present invention. As depicted, the device 2300 is generally similar to the syringe devices 2100, 2200 as described above, for example, comprising a generally elongate barrel 2310 comprising a base end 2312 and an administration end 2314. In example embodiments, the administration end 2314 comprises an outer collar portion 2316 and a centrally-positioned transfer port 2317, for example, wherein a generally cylindrical cavity 2330 is formed therebetween. A lumen 2318 extends through the transfer port 2317 such that fluids can be drawn in the syringe via retraction of the plunger, or wherein actuation of the plunger provides for the delivery of fluids through the lumen 2318 and from the transfer port 2317. Similarly, the administration end 2314 can be inserted directly into a patient's mouth for delivery of the fluids or medicine.

In example embodiments, the tubes, straws, applicators, etc. as described and shown in FIGS. 38-89 can be sized and shaped as desired, and can be formed from one or more materials, for example, which can be flexible, partially flexible, substantially flexible, partially rigid, substantially rigid, or otherwise provide sufficient flexibility and rigidity as desired. Preferably, the one or more materials forming the tubes, straws, applicators, etc. can be polyvinyl chloride (PVC), silicon, polyurethane (PU), polypropylene (PP), or other materials as desired. For example, according to some example embodiments, a feeding tube sized between about 4 Fr to about 12 Fr can be provided and formed from any available material. In some example embodiments, the feeding tube is formed from polyvinyl chloride (PVC). Optionally, as recited above, the tube, straw, applicator can be formed from one or more other available materials as desired. According to some example embodiments, the tube, straw, applicator, etc. can be substantially soft and comfortable, for example to mitigate any trauma during oral delivery. The length or extension of the entire coupler (with tube attached) can generally range between about 20 millimeters to about 160 millimeters. Furthermore, the inner diameter or internal conduit can be sized as desired, for example, to ensure dosing inaccuracies are mitigated. According to additional example embodiments of the present invention, the couplers as described in FIGS. 38-80 can be configured for providing for removable engagement with helical threads T of a threaded tip TT of a syringe (see FIGS. 31-34).

According to example embodiments of the present invention, the couplers of the present invention can preferably be provided with a cover, sheath or capping member, for example, to generally cover, seal or enclose the lumen or other portions of the coupler such that the entirety thereof (or at least a portion thereof) is generally protected from the elements. In some example embodiments, the cover or sheath is generally a bag-like liner or plastic sheet material or bag. In some example embodiments, a more rigid cap or cover can be fastened or secured to an end portion of the applicator. As described above, one or more portions of the syringe or other portions of the coupler can comprise a clamp or other capture portions for generally securing the applicator thereto when not in use.

According to example embodiments, the plurality of couplers as described herein are preferably sized, shaped and configured to not be a choking hazard. For example, according to example embodiments, the plurality of couplers shown and described herein are at least of a size and shape to comply with the ISO80369-3 choking hazard standard. According to some example embodiments as described above, one or more vents or openings can be formed in the flange to further mitigate any choking risks.

While the invention has been described with reference to preferred and example embodiments, it will be understood by those skilled in the art that a variety of modifications, additions and deletions are within the scope of the invention, as defined by the following claims.

What is claimed is:

1. An oral administration coupler for delivering fluids from a syringe to a child or infant, the syringe comprising a female connector, the oral administration coupler comprising:
   a coupling comprising an ENFit compatible coupling end and an applicator coupling end, and a conduit extending therebetween; and
   a straw comprising a first end coupled to the applicator coupling end and a second end generally oppositely extending therefrom,
   wherein the ENFit compatible coupling comprises an outer circumferential collar having threads defined on an internal portion thereof, and a transfer port generally axially extending relative to the collar and comprising the conduit extending therethrough, and wherein at least one vent is formed within a portion of the collar and generally defined between the collar and the transfer port.

2. The oral administration coupler of claim 1, wherein the ENFit compatible coupling is configured for removable engagement with the female connector of the syringe.

3. The oral administration coupler of claim 1, further comprising a flange extending outwardly from the collar and being positioned between the ends of the coupling.

4. The oral administration coupler of claim 3, wherein the flange is generally circular in shape, and wherein a smoothly radiused transitional surface is provided from the generally elongate member to an outer peripheral portion of the flange.

5. The oral administration coupler of claim 3, wherein the flange is generally non-circular in shape and comprises a plurality of openings.

6. The oral administration coupler of claim 1, wherein the female connector of the syringe further comprises a lumen extension tip axially extending therein and comprises a lumen therein and in communication with an internal chamber of the syringe, and wherein when the female connector is engaged with the ENFit compatible coupling end of the coupling, the lumen extension tip fully extends within a conduit of the transfer port.

7. The oral administration coupler of claim 6, wherein a volume defined within the conduit of the coupler is substantially reduced by the conduit of the transfer port being occupied by the lumen extension tip of the female connector.

8. The oral administration coupler of claim 7, wherein the volume defined within the conduit is generally no more than about 0.01 mL.

9. The oral administration coupler of claim 1, wherein a length of between about 20 millimeters to about 80 millimeters is defined between the ENFit compatible coupling end and the second end of the straw.

10. The oral administration coupler of claim 1, wherein the straw comprises polyvinyl chloride.

11. The oral administration coupler of claim 1, wherein the straw comprises polyurethane.

12. The oral administration coupler of claim 1, wherein the straw comprises silicone.

13. The oral administration coupler of claim 1, wherein the straw comprises an outer diameter of between about 2-6 millimeters and an inner diameter of between about 0.3-2 millimeters.

14. The oral administration coupler of claim 13, wherein the straw comprises an outer diameter of about 4 millimeters and an inner diameter of about 0.56 millimeters.

15. The oral administration coupler of claim 1, wherein the second end of the straw comprises a rounded surface to mitigate the risk of trauma during oral delivery.

16. The oral administration coupler of claim 1, wherein at least one connecting member couples the collar to the transfer port.

17. An oral administration coupler for back-of-mouth delivery comprising:
- a central fluid transfer member comprising a first end and a generally opposite second end, the first end comprising a syringe coupling and the second end comprising a tube extending therefrom in a direction generally opposite the first end, the syringe coupling comprising an outer circumferential collar having threads defined on an internal portion thereof, a transfer port generally axially extending relative to the collar of the syringe coupling, and at least one vent formed within a portion of the collar and generally defined between the collar and the transfer port; and
- a lumen defined within the central fluid transfer member and extending from the first end to the second end through the entirety of the transfer port and the tube, wherein the central fluid transfer member defines a length between the first and second ends sufficient to deliver fluid from the central fluid transfer member to a back of a child's mouth from a fluid delivery device at least partially external of the child's mouth.

18. The oral administration coupler of claim 17, wherein the coupling is configured for removable engagement with a syringe having a threaded tip.

19. The oral administration coupler of claim 17, wherein a length of between about 15 millimeters to about 60 millimeters is defined between the first and second ends of the central fluid transfer member.

20. The oral administration coupler of claim 17, wherein an end portion of the tube is substantially tapered or rounded such that trauma to a patient's mouth is mitigated.

21. The oral administration coupler of claim 17, wherein the syringe coupling of the first end is an ISO 80369-3 formatted coupling.

22. The oral administration coupler of claim 17, wherein the tube comprises polyvinyl chloride.

23. The oral administration coupler of claim 17, wherein the tube comprises polyurethane.

24. The oral administration coupler of claim 17, wherein the tube comprises silicone.

25. The oral administration coupler of claim 17, wherein the tube comprises between about a 4 Fr to about a 12 Fr feeding tube.

26. The oral administration coupler of claim 17, wherein the tube comprises an outer diameter of about 4 millimeters and an inner diameter of about 0.56 millimeters.

27. The oral administration coupler of claim 21, wherein the ISO 80369-3 formatted coupling is configured for coupling engagement with a female connector a syringe, wherein the syringe further comprises a lumen extension tip axially extending therein and comprises a lumen therein and in communication with an internal chamber of the syringe, and wherein when the female connector is engaged with the ISO 80369-3 formatted coupling, the lumen extension tip fully extends within a conduit of the transfer port.

28. An oral administration coupler for delivering fluids from a syringe to a child or infant, the syringe comprising a female connector, the oral administration coupler comprising a conduit extending from a first end to a second end, the first end comprising an elongate applicator for oral insertion to deliver fluids to the child or infant, and the second end comprising a coupling for removable engagement with the female connector of the syringe, the coupling comprising an outer circumferential collar having threads defined on an internal portion thereof and a transfer port generally axially extending relative to the collar and comprising the conduit extending therethrough, and wherein at least one vent is formed within a portion of the collar and generally defined between the collar and the transfer port.

29. The oral administration coupler of claim 28, further comprising a clamp for temporarily closing or sealing the elongate applicator.

30. The oral administration coupler of claim 28, further comprising a plunger movably mounted within a barrel of the syringe, the plunger comprising an elongate tube extending therefrom for insertion within the conduit of the oral administration coupler so as to reduce a volume defined by the conduit of the oral administration coupler such that dosing inaccuracies are improved.

31. The oral administration coupler of claim 28, wherein the elongate applicator comprises one or more markings or graduations for assisting in the measurement of a dosage quantity.

32. The oral administration coupler of claim 28, wherein the elongate applicator comprises an outer tube and an inner tube, wherein the outer tube comprises an inner diameter and an outer diameter and the inner tube comprises an inner diameter and an outer diameter, wherein the outer diameter of the inner tube is generally dimensionally similar to the inner diameter of the outer tube.

33. The oral administration coupler of claim 28, further comprising a radial channel formed along a portion of the outer circumferential collar, and a flange is connectable with the radial channel.

34. The oral administration coupler of claim 28, further comprising a cover or cap connectable to an end of the elongate applicator for providing closure to the conduit.

35. An oral administration coupler for delivering fluids from a syringe to a child or infant, the syringe comprising a female connector, the oral administration coupler comprising:
- a coupling comprising a syringe coupling end and an applicator coupling end, and a conduit extending therebetween; and
- a straw comprising a first end coupled to the applicator coupling end and a second end generally oppositely extending therefrom,
- wherein the syringe coupling end comprises an outer circumferential collar having threads defined on an internal portion thereof, and a transfer port generally axially extending relative to the collar and comprising the conduit extending therethrough, and wherein at least one vent is formed within a portion of the collar and generally defined between the collar and the transfer port.

* * * * *